(12) United States Patent
Angibaud et al.

(10) Patent No.: US 12,239,384 B2
(45) Date of Patent: Mar. 4, 2025

(54) COMPUTER-BASED PLATFORM FOR IMPLEMENTING AN INTRA-OPERATIVE SURGICAL PLAN DURING A TOTAL JOINT ARTHROPLASTY

(71) Applicant: EXACTECH, INC., Gainesville, FL (US)

(72) Inventors: Laurent Angibaud, Gainesville, FL (US); Cyril Hamad, Meylan (FR)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 18/054,653

(22) Filed: Nov. 11, 2022

(65) Prior Publication Data

US 2023/0149090 A1    May 18, 2023

Related U.S. Application Data

(60) Provisional application No. 63/346,095, filed on May 26, 2022, provisional application No. 63/300,190, (Continued)

(51) Int. Cl.
*A61B 34/10* (2016.01)
*A61B 34/00* (2016.01)

(52) U.S. Cl.
CPC .............. *A61B 34/10* (2016.02); *A61B 34/25* (2016.02); *A61B 2034/102* (2016.02); (Continued)

(58) Field of Classification Search
CPC ............... A61B 34/10; A61B 34/25; A61B 2034/101–108; A61B 2034/252; A61B 2034/254
See application file for complete search history.

(56) References Cited

U.S. PATENT DOCUMENTS

| 8,337,503 B2 * | 12/2012 | Lian ................... | A61B 17/15 606/87 |
| 8,337,508 B2 * | 12/2012 | Lavallee .............. | A61B 34/20 606/105 |

(Continued)

OTHER PUBLICATIONS

Kramer, et al., Evaluation of cartilage degeneration in a rat model of rotator cuff tear arthropathy, 2013, Journal of Shoulder Elbow Surgery, 22, p. 1702-1709 (Year: 2013).*

(Continued)

*Primary Examiner* — Daniel L Cerioni
*Assistant Examiner* — Raymond P Dulman
(74) *Attorney, Agent, or Firm* — GREENBERG TRAURIG, LLP

(57) ABSTRACT

A method includes receiving by a controller, a surgeon-specific surgery profile for an implantation of an implant into a joint, implant profiles, a patient-specific post-surgery desired functional profile of the joint after the implantation, and bone registration data for a first bone member and a second bone member of a patient are inputted into a surgical plan model to generate a surgical plan. The surgical plan model is designed to achieve the patient-specific post-surgery desired functional profile based at least in part on a plurality of dependencies between a plurality of surgical parameters, the implant profiles, at least one functional parameter representative of the expected functional performance of the joint, and movement-related data of the joint. The surgical plan is outputted on a graphical user interface (GUI) on a surgery assistant device to facilitate the implantation.

13 Claims, 66 Drawing Sheets

Related U.S. Application Data filed on Jan. 17, 2022, provisional application No. 63/278,683, filed on Nov. 12, 2021.

(52) U.S. Cl.
CPC ... *A61B 2034/105* (2016.02); *A61B 2034/107* (2016.02); *A61B 2034/252* (2016.02); *A61B 2034/256* (2016.02); *A61B 2034/258* (2016.02)

(56) References Cited

U.S. PATENT DOCUMENTS

| | | | |
|---|---|---|---|
| 9,913,692 B2 | 3/2018 | Arata et al. | |
| 9,916,421 B2 | 3/2018 | Vorhis et al. | |
| 10,064,685 B2 | 9/2018 | Bellettre et al. | |
| 11,071,592 B2 | 7/2021 | McGuan et al. | |
| 2004/0030245 A1 | 12/2004 | Nobel et al. | |
| 2009/0089081 A1 | 4/2009 | Haddad | |
| 2010/0042105 A1* | 2/2010 | Park | A61B 17/1703 606/87 |
| 2014/0180295 A1* | 6/2014 | Buza | A61B 17/15 29/592 |
| 2016/0278754 A1* | 9/2016 | Todorov | A61F 2/389 |
| 2019/0254751 A1 | 8/2019 | Dossett et al. | |
| 2020/0008876 A1* | 1/2020 | Nikou | A61B 34/20 |
| 2021/0128244 A1* | 5/2021 | Couture | G16H 40/63 |
| 2021/0322100 A1 | 10/2021 | Roche et al. | |

OTHER PUBLICATIONS

International Search Report and Written Opinion from International Application No. PCT/US/2022/079704 dated Feb. 22, 2023.

* cited by examiner

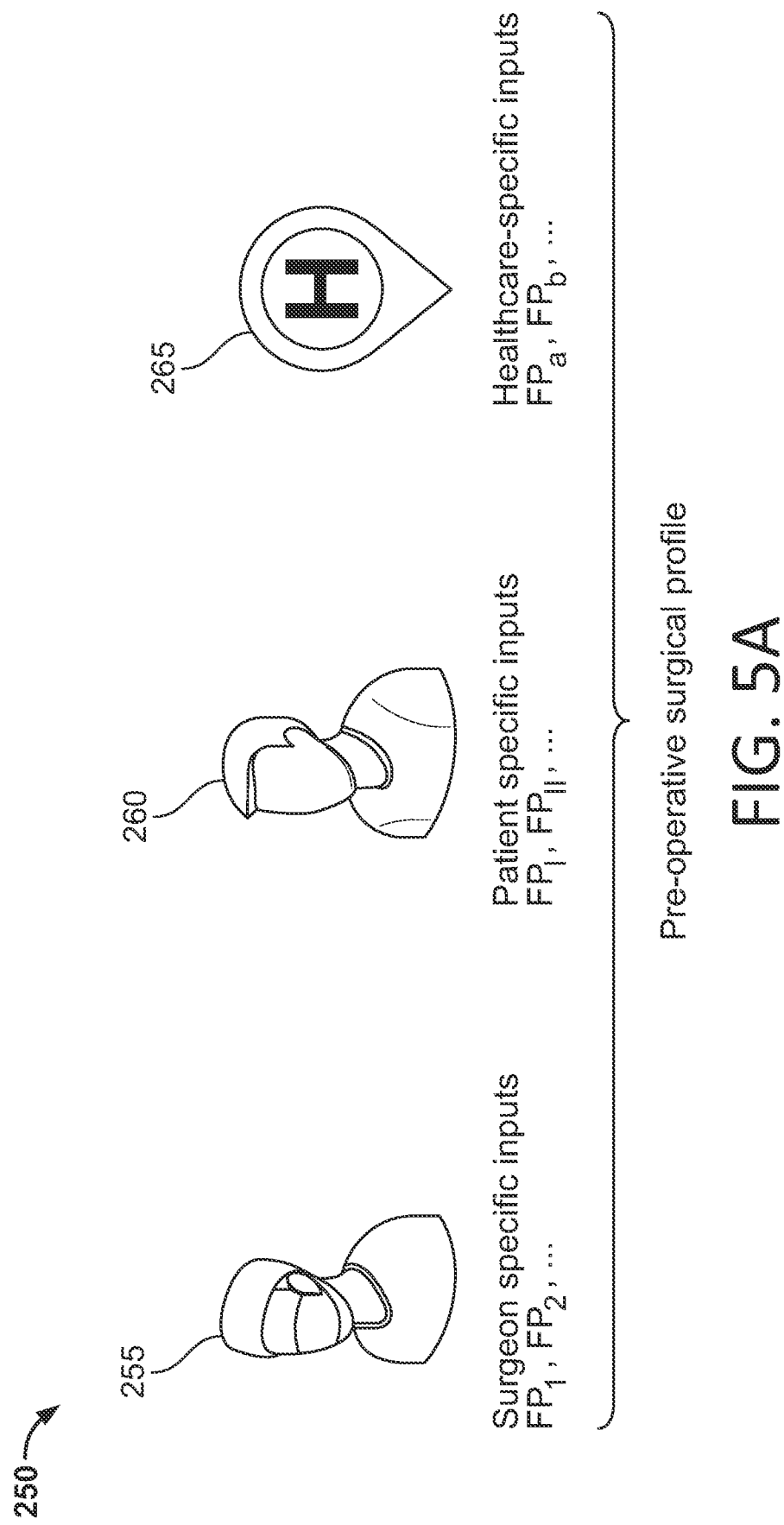

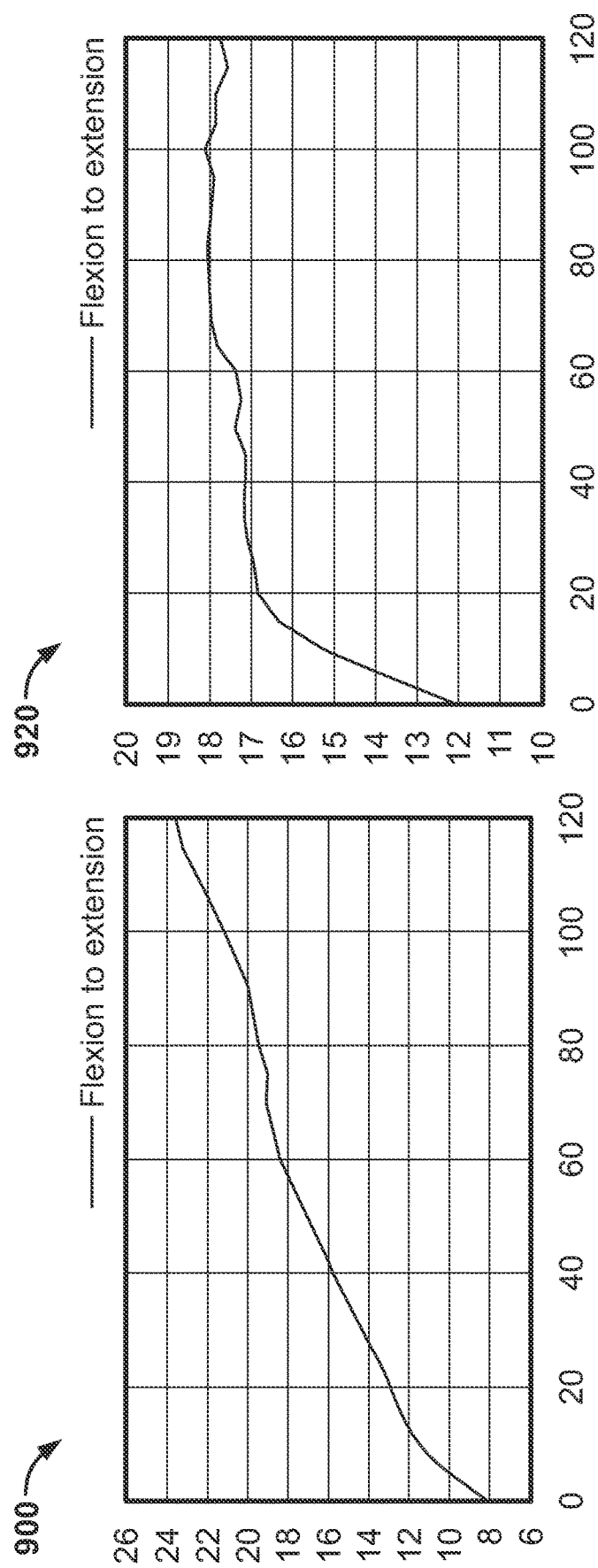

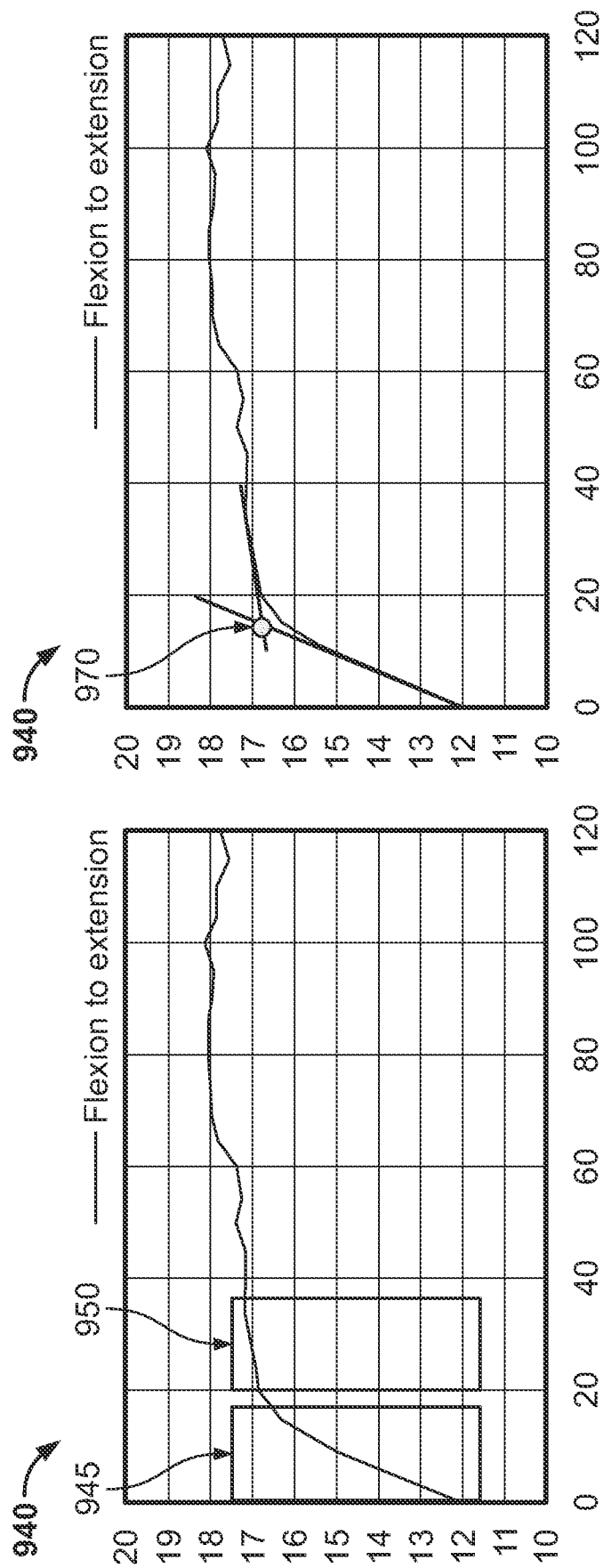

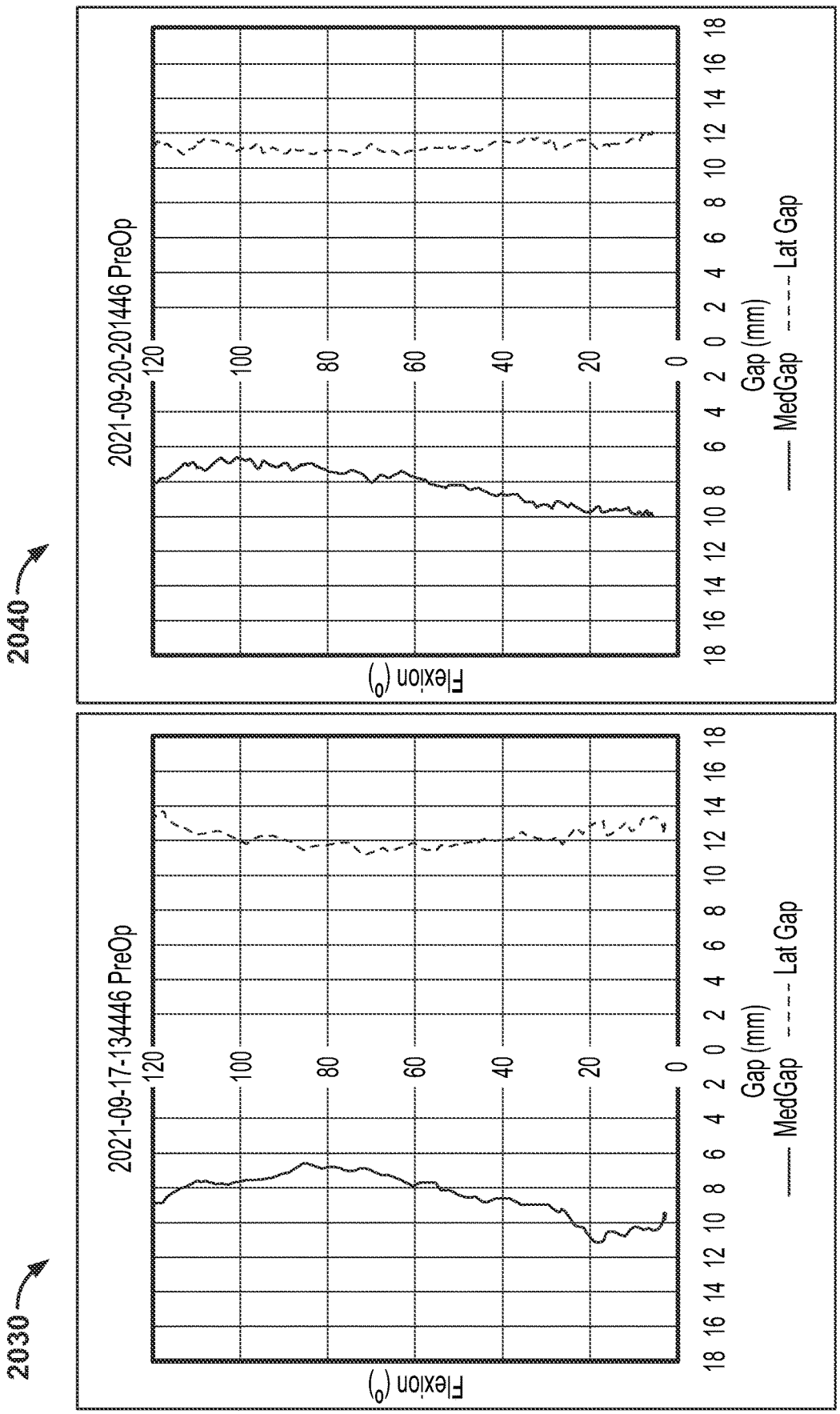

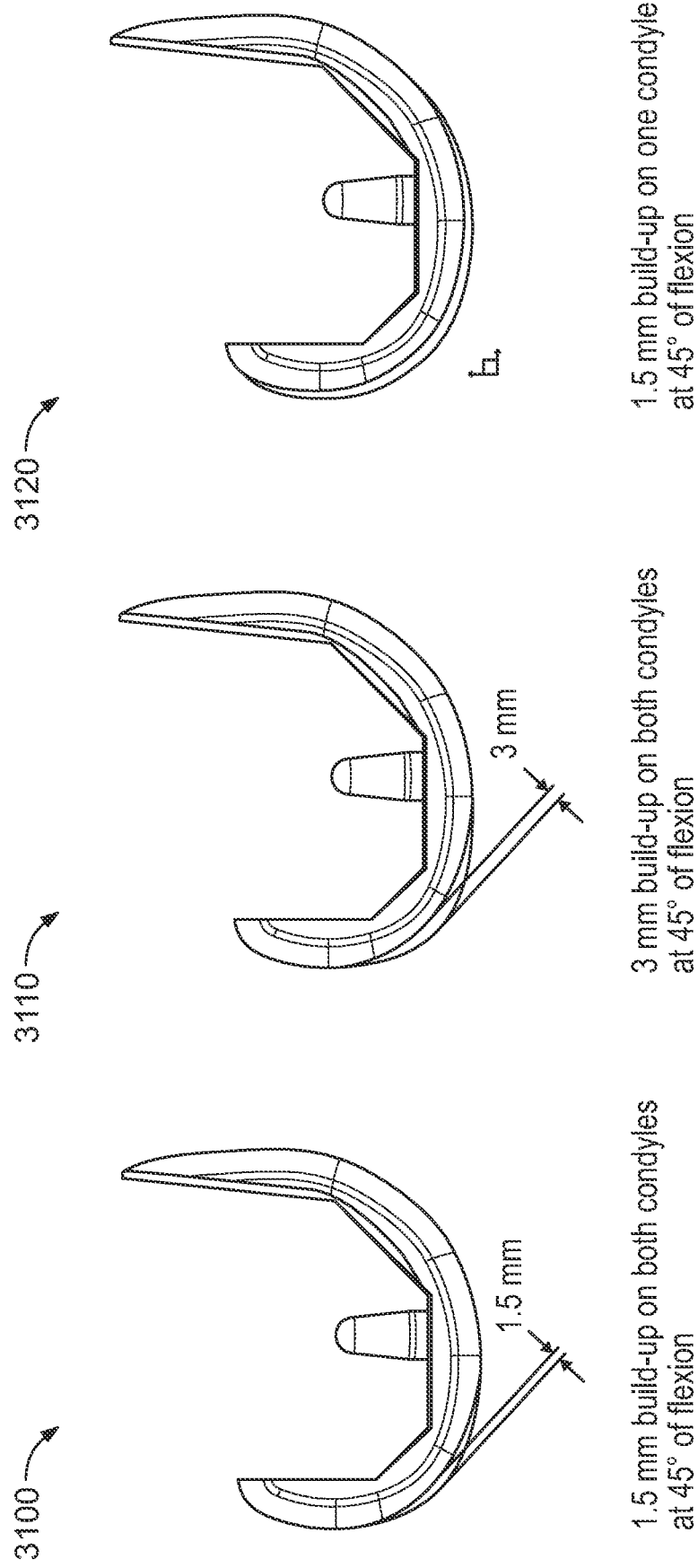

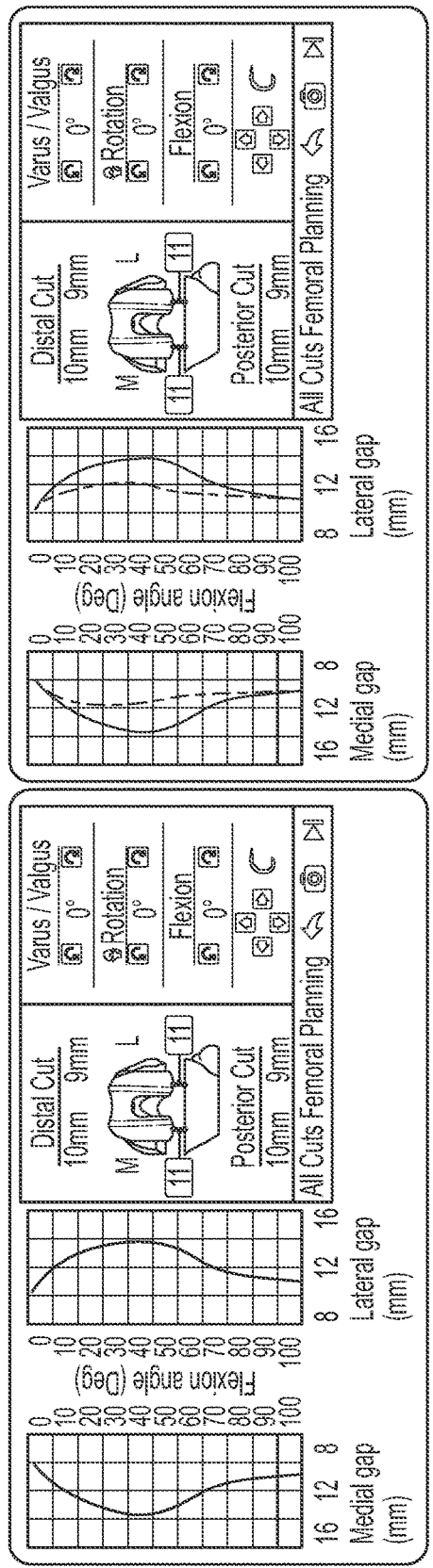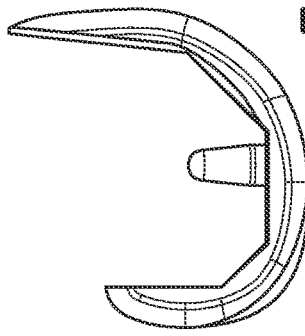
FIG. 36A
FIG. 36B
FIG. 36C

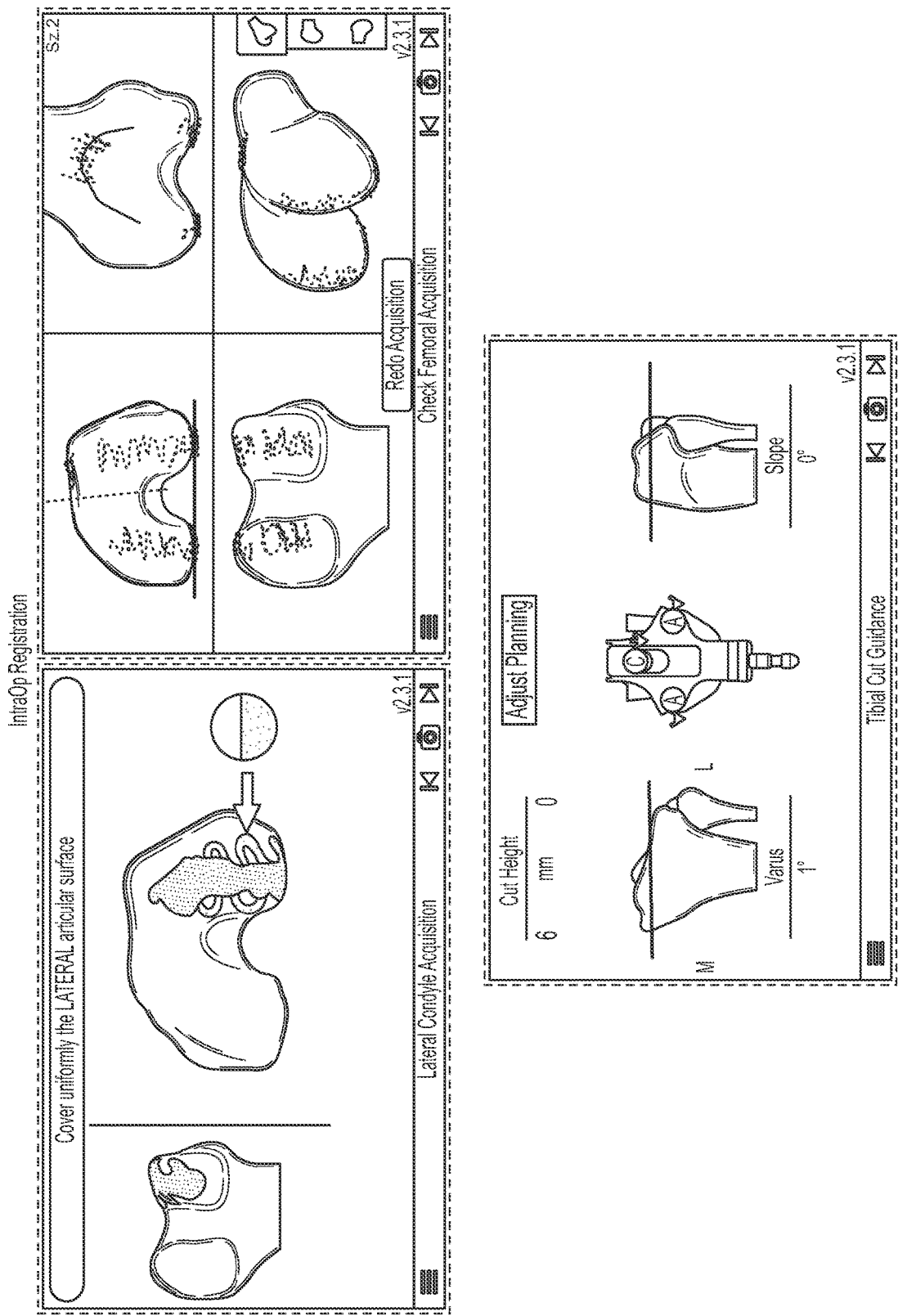
FIG. 37 (Cont. 3)

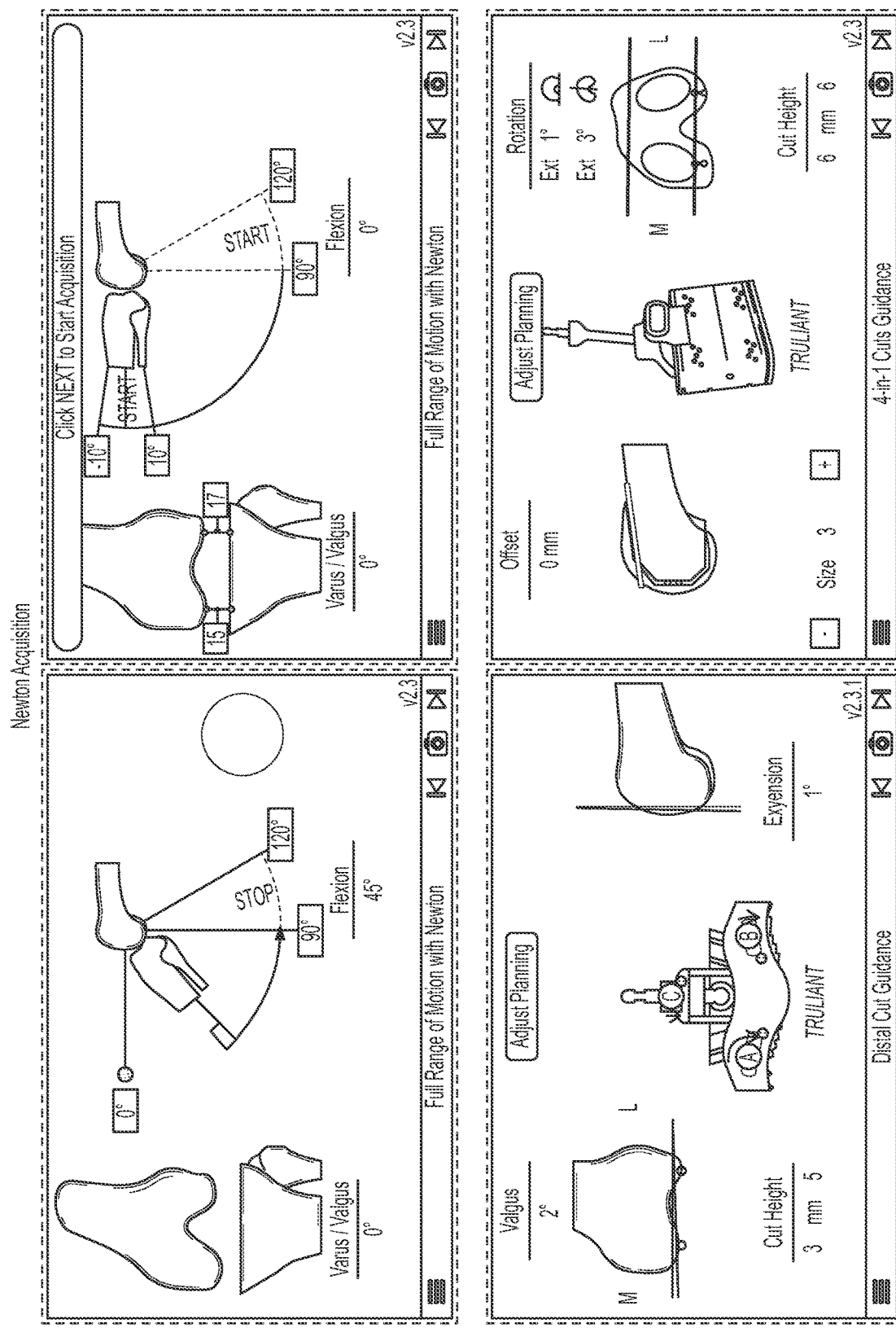
FIG. 37 (Cont. 4)

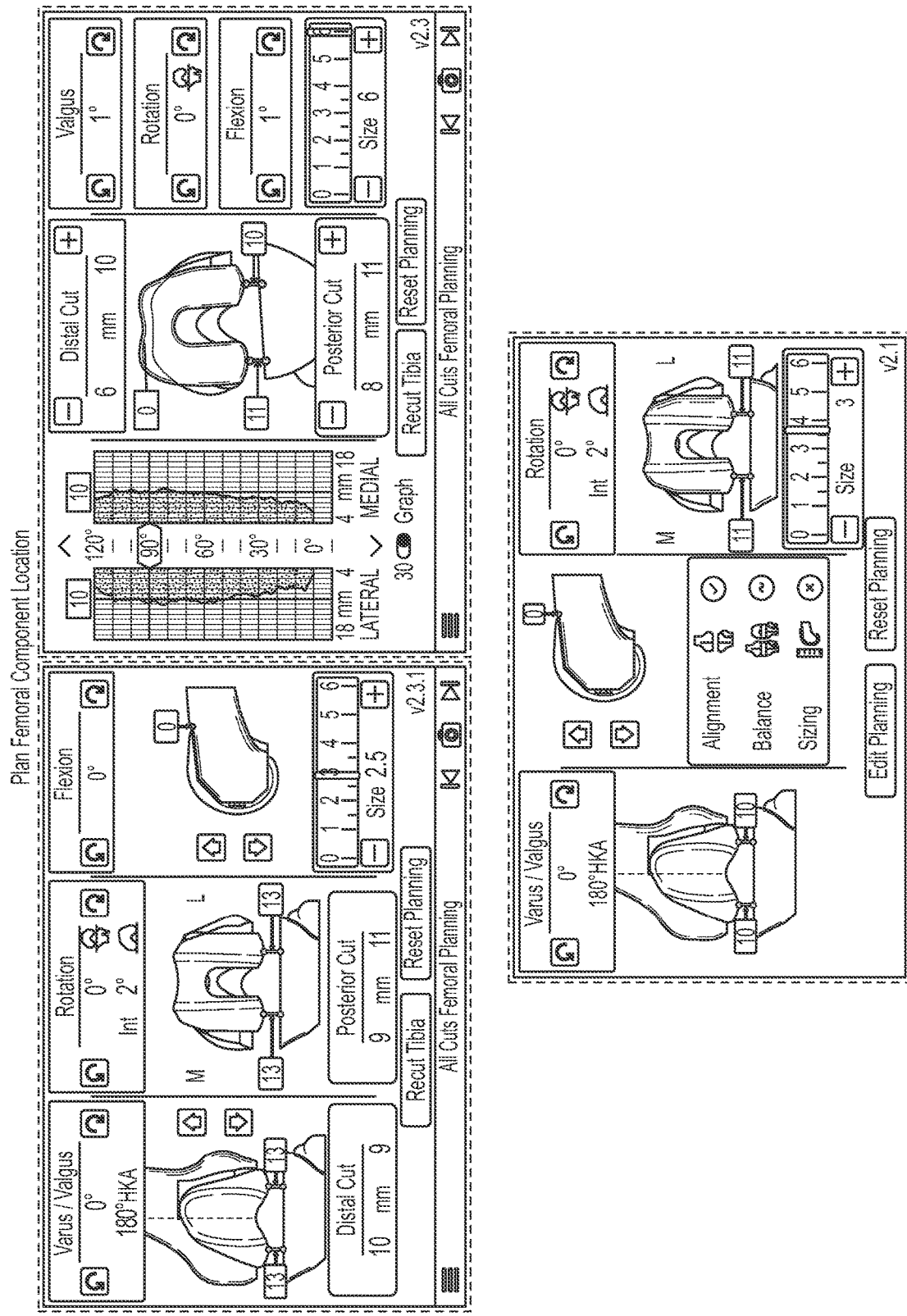
FIG. 37 (Cont. 5)

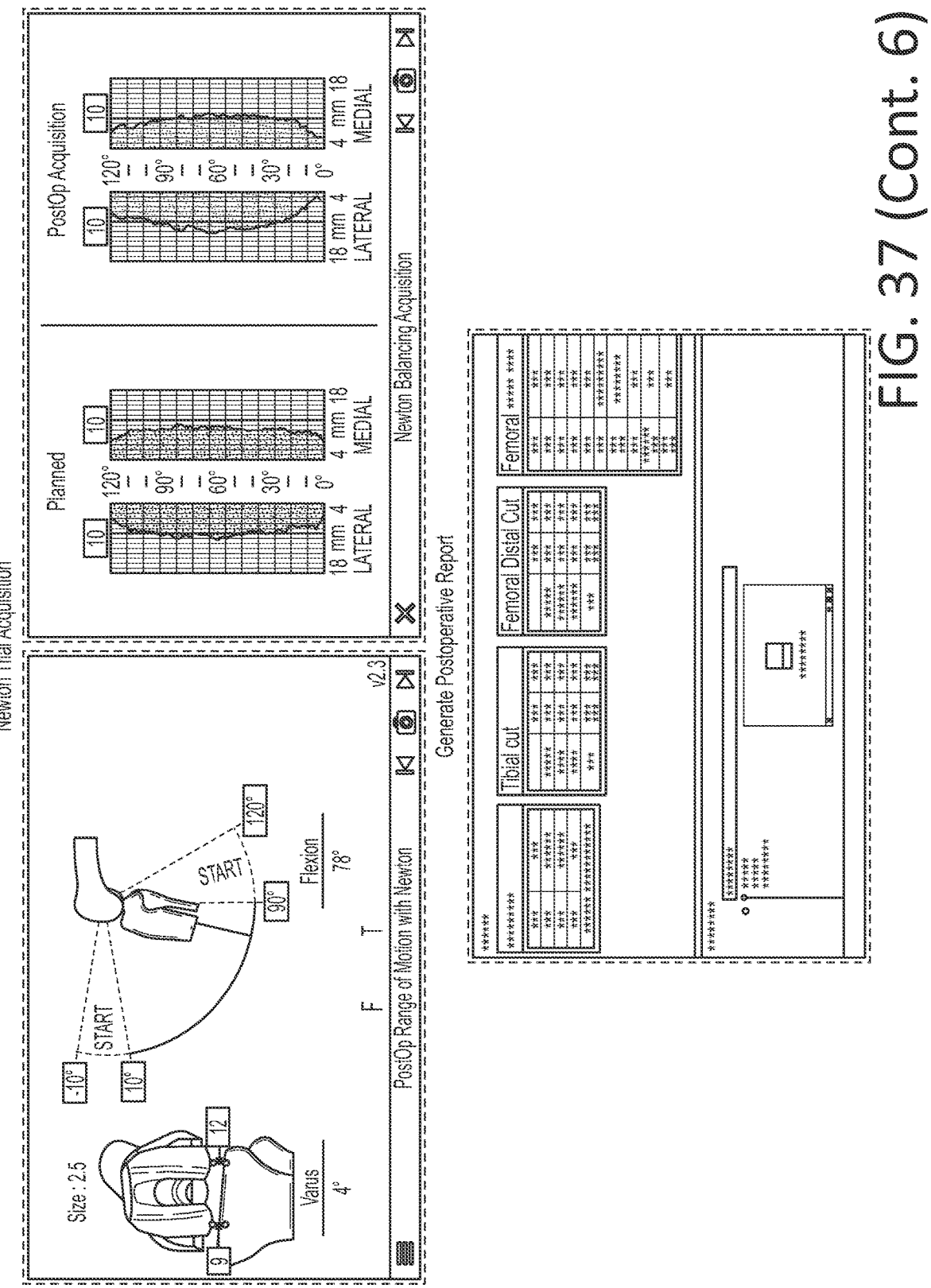
FIG. 37 (Cont. 6)

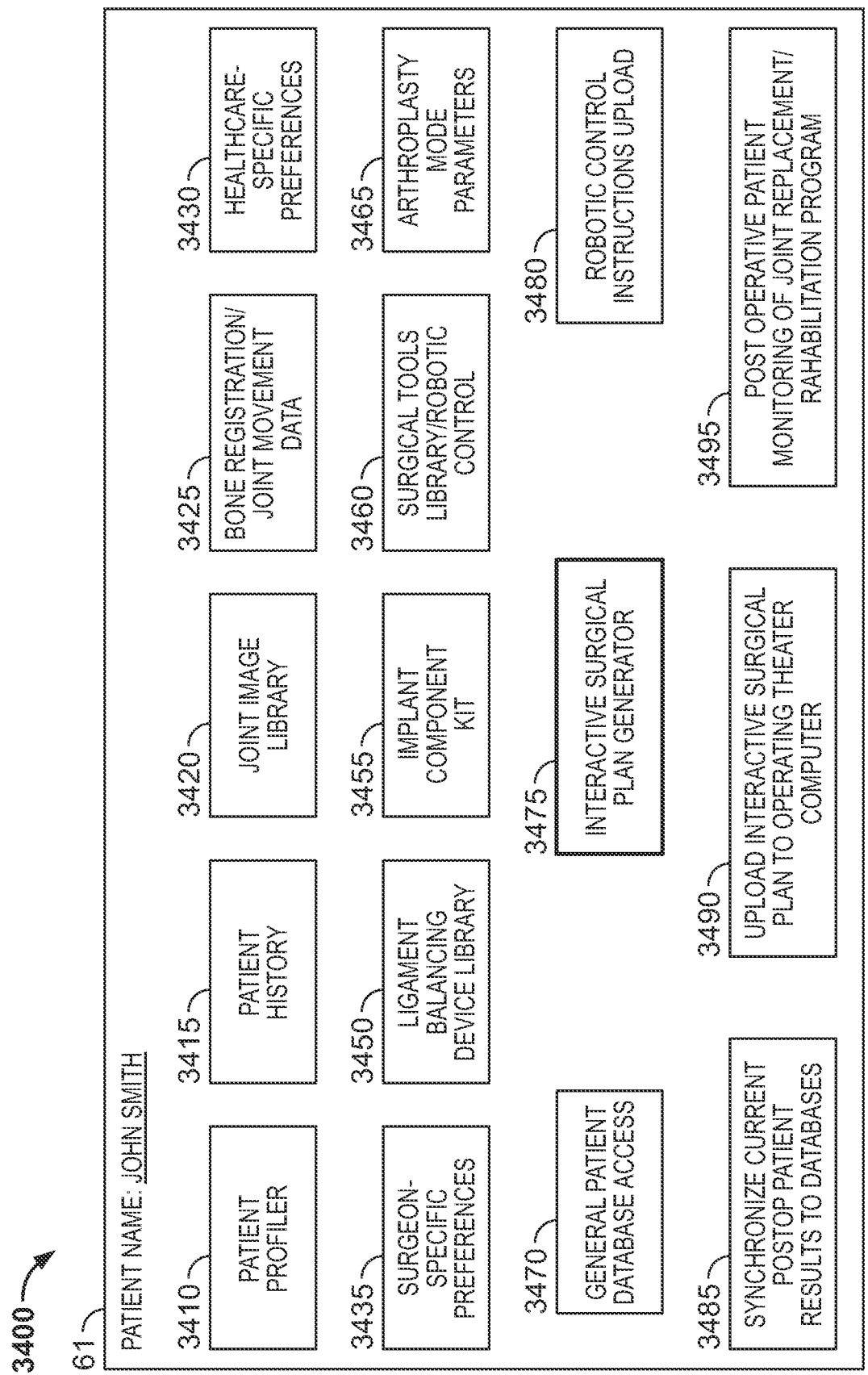

|  | Random Forest (%) | Ordinal Logistic Regression (%) |
|---|---|---|
| Surgeon 1: N=13 | | |
| Exact prediction | 39% | 31% |
| \|Predicted - Actual thickness\| ≤ 1mm | 85% | 77% |
| \|Predicted - Actual thickness\| ≤ 2mm | 100% | 92% |
| Surgeon 2: N=11 | | |
| Exact prediction | 45% | 54% |
| \|Predicted - Actual thickness\| ≤ 1mm | 82% | 82% |
| \|Predicted - Actual thickness\| ≤ 2mm | 100% | 100% |

COMPUTER-BASED PLATFORM FOR IMPLEMENTING AN INTRA-OPERATIVE SURGICAL PLAN DURING A TOTAL JOINT ARTHROPLASTY

FIELD OF TECHNOLOGY

The present disclosure generally relates to orthopedic surgery, and more particular to an improved computer-based platform for implementing an intra-operative surgical plan during a total joint arthroplasty.

BACKGROUND OF TECHNOLOGY

Total joint replacements are one of the most successful procedures in the medical field. The most common total joint replacement procedures in the U.S. are total knee replacements (approximately 790,000 a year) and total hip replacements (approximately 450,000 a year). Although joint replacement surgeries are associated with remarkable outcomes, it has been reported that a significant portion of patients (up to 20%) are not satisfied with their clinical outcomes. While this situation may be due to many factors, such as patient expectations, it has been reported that surgical technique used by the surgical staff may play an important role in determining successful clinical outcomes. Similarly, despite the high survivorship of total joint replacements (e.g., more than 95% at 10 years), early revisions for joint instability or joint stiffness, for example, seems to be a primary factor due to intra-operative technical errors or inability to properly define the personalized cut parameters during the set-up of patient-based surgical planning. Thus, there is a need in the art for surgical approaches in reducing intra-operative technical errors and for personalizing the definition of a surgical plan.

SUMMARY OF DESCRIBED SUBJECT MATTER

In some embodiments, the present disclosure provides an exemplary technically improved computer-based method that includes at least the following steps of:
receiving, by at least one controller, a surgeon-specific surgery profile;
  where the surgeon-specific surgery profile may include a first range of surgeon-specific surgery guidance values for each of a plurality of surgical parameters for an implantation into a joint of at least one part of an implant chosen from a plurality of implants;
receiving, by the at least one controller, a patient-specific post-surgery desired functional profile of the joint after the implantation;
  where the patient-specific post-surgery desired functional profile may include at least one functional parameter value for at least one functional parameter representative of an expected functional performance of the joint after the implantation;
receiving, by the at least one controller, bone registration data for a first bone member of a patient and a second bone member of the patient;
modeling, by the at least one controller, within a non-transient computer memory, based on the bone registration data, a first bone member representation of the first bone member and a second bone member representation of the second bone member within at least one coordinate system;
receiving, by the at least one controller, during a surgical procedure, movement-related data after the first bone member of the joint, the second bone member of the joint, or both, have been put through at least one movement when a distraction force is applied, between the first bone member and the second bone member, throughout a continuous range of motions;
  where the movement-related data may represent a plurality of spatial poses of at least one first feature associated with the first bone member, at least one second feature associated with the second bone member, at least one third feature associated with the joint, or any combination thereof;
inputting, by the at least one controller, a plurality of inputs into a surgical plan model to generate a patient-specific surgeon-specific surgical plan;
  where the patient-specific surgeon-specific surgical plan may include an estimated patient-specific surgeon-specific value for each of the plurality of surgical parameters;
  where the plurality of inputs may include:
    an implant profile of the implant chosen from the plurality of implants,
    the first range of surgeon-specific surgery guidance values for each of the plurality of surgical parameters,
    the at least one functional parameter value for the at least one functional parameter representative of the expected functional performance of the joint after the implantation,
    the first and the second bone member representations, and
    the movement-related data;
  where the surgical plan model may be designed to achieve the patient-specific post-surgery desired functional profile based at least in part on a plurality of dependencies between:
    the plurality of surgical parameters,
    the plurality of implant profiles,
    the at least one functional parameter representative of the expected functional performance of the joint, and
    the movement-related data; and
outputting, by the at least one controller, the patient-specific surgeon-specific surgical plan on a graphical user interface (GUI) on a surgery assistant device to facilitate the implantation.

In some embodiments, the present disclosure provides an exemplary technically improved computer-based system that includes at least the following components of a memory and at least one controller. The at least one controller may be configured to execute software code stored in the memory that configures the at least one controller to:
receive a surgeon-specific surgery profile;
  where the surgeon-specific surgery profile may include a first range of surgeon-specific surgery guidance values for each of a plurality of surgical parameters for an implantation into a joint of at least one part of an implant chosen from a plurality of implants;
receive a patient-specific post-surgery desired functional profile of the joint after the implantation;
  where the patient-specific post-surgery desired functional profile may include at least one functional parameter value for at least one functional parameter representative of an expected functional performance of the joint after the implantation;
receive bone registration data for a first bone member of a patient and a second bone member of the patient;

model within a non-transient computer memory, based on the bone registration data, a first bone member representation of the first bone member and a second bone member representation of the second bone member within at least one coordinate system;

receive, during a surgical procedure, movement-related data after the first bone member of the joint, the second bone member of the joint, or both, have been put through at least one movement when a distraction force is applied, between the first bone member and the second bone member, throughout a continuous range of motions;

where the movement-related data may represent a plurality of spatial poses of at least one first feature associated with the first bone member, at least one second feature associated with the second bone member, at least one third feature associated with the joint, or any combination thereof;

input a plurality of inputs into a surgical plan model to generate a patient-specific surgeon-specific surgical plan;

where the patient-specific surgeon-specific surgical plan may include an estimated patient-specific surgeon-specific value for each of the plurality of surgical parameters;

where the plurality of inputs may include:
an implant profile of the implant chosen from the plurality of implants,
the first range of surgeon-specific surgery guidance values for each of the plurality of surgical parameters,
the at least one functional parameter value for the at least one functional parameter representative of the expected functional performance of the joint after the implantation,
the first and the second bone member representations, and
the movement-related data;

where the surgical plan model may be designed to achieve the patient-specific post-surgery desired functional profile based at least in part on a plurality of dependencies between:
the plurality of surgical parameters,
the plurality of implant profiles,
the at least one functional parameter representative of the expected functional performance of the joint, and
the movement-related data; and output the patient-specific surgeon-specific surgical plan on a graphical user interface (GUI) on a surgery assistant device to facilitate the implantation.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

FIG. 5A illustrates different inputs for a pre-operative surgical profile in accordance with one or more embodiments of the present disclosure;

FIGS. 11A and 11B illustrate laxity curves for two patients in accordance with one or more embodiments of the present disclosure;

FIGS. 12A-12C illustrate a flow for modeling joint laxity curves in accordance with one or more embodiments of the present disclosure;

FIGS. 25A-25E show pre-operative laxity curves in accordance with one or more embodiments of the present disclosure;

FIGS. 35A-35C illustrate components of an implant component kit in accordance with one or more embodiments of the present disclosure;

FIGS. 36A-36C show an impact on the surgical plan with and without using the implant kit in accordance with one or more embodiments of the present disclosure;

FIG. 37 illustrates a first exemplary top-level view of an implant planning software tool in accordance with one or more embodiments of the present disclosure;

FIG. 38 illustrates a second exemplary top-level view of an implant planning software tool in accordance with one or more embodiments of the present disclosure;

FIG. 41 shows a table illustrating a summary of predictive model accuracy on testing datasets for the two surgeons in accordance with one or more embodiments of the present disclosure;

DETAILED DESCRIPTION

Figure 1:
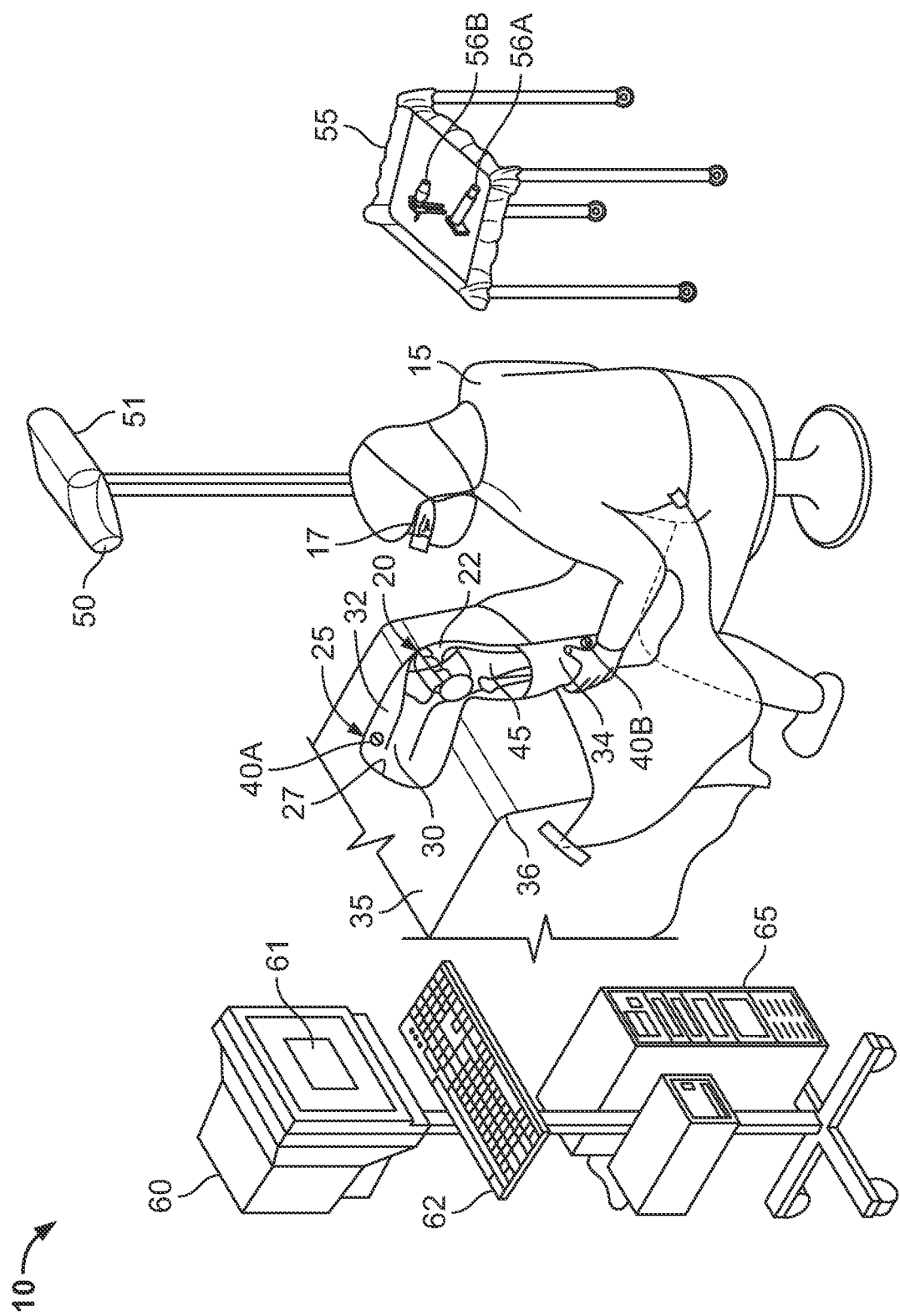
FIG. 1 schematically illustrates an operating room using an improved computer-based platform for implant planning during a total joint arthroplasty in accordance with one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

Embodiments of the present disclosure herein describe an improved computer-based platform for implant planning for total joint arthroplasty. The computer-assisted surgery (CAS) platform reduces intra-operative technical errors during total joint arthroplasty procedures and accounts for the proper management of the soft-tissue surrounding the joint as an important factor to improve patient satisfaction as well as clinical outcomes. Ligament balancing techniques as well as the surgeon training and skill may be critical factors for improving total knee arthroplasty (TKA) outcomes, for example. Moreover, CAS technologies may be used to provide guidance to the surgeon both before and during the total arthroplasty procedure.

In some embodiments, the CAS technologies may be image-based and may rely on pre-operative computed tomography (CT) scans and/or pre-operative magnetic resonance imaging (MRI) scans of the joint, after which a processor may implement segmentation of the joint images to allow for the reconstruction of a 3D representation of the considered joint. Then, the CAS software application as described herein may provide pre-operative planning. The surgeon may establish a first surgical plan by selecting the proper size and type of implant, and then planning the position and orientation of the selected implants relative to the reconstructed 3D model. It should be understood to one skilled in the art that the CAS technologies shown herein may be applied to any total joint arthroplasty procedure for any joint in a living body and not limited to a total knee arthroplasty procedure as per the exemplary embodiments shown herein.

FIG. 1 schematically illustrates an operating room 10 using an improved computer-based platform for implant planning during a total joint arthroplasty in accordance with one or more embodiments of the present disclosure. The embodiments shown in FIG. 1 refer to a total knee arthroplasty procedure. FIG. 1 shows a surgeon 15 operating on a leg 25 of a patient positioned on an operating table 35. The leg 25 of the patient may be placed through a surgical drape opening 27 for access to the leg 25 by the surgeon 15. In this exemplary embodiment, the surgeon 15 may perform a total knee arthroplasty procedure on the patient via an incision 22 made by the surgeon 15 to expose a knee joint 20 of the patient. The leg 25 as shown in FIG. 1 may include an upper portion 32 (e.g., a first member—thigh) with a femur 30 (e.g., first bone member), a lower portion 34 (e.g., a second member—calf) with a tibia 45 (e.g., second bone member), and the knee joint 20.

In some embodiments, at least one first tracking device 40A may be coupled to the upper portion 32 of the leg 25 (e.g., a first bone member) and at least one second tracking device 40B (e.g., a second bone member) may be coupled to the lower portion 34 of the leg 25. In other embodiments, the at least one first tracker 40A and the at least one second tracker 40B may be rigidly mounted to the bone members (e.g., respectively to the femur 30 and to the tibia 45 for the embodiments of FIG. 1).

In some embodiments, the operating room 10 may include at least one imaging camera 50 shown schematically in FIG. 1 mounted on an image camera assembly 51. Note that any suitable number of cameras of any suitable type may be mounted on the image camera assembly 51 that may be used to track 3D objects. The at least one imaging camera 50 may be used to acquire a position and/or orientation of the bone members in a three-dimensional (3D) environment.

In some embodiments, the operating room 10 may include at least one surgical tool 56A and/or at least one surgical probe 56B placed on a cart 55 easily accessible by the surgeon 15 during the total joint arthroplasty procedure.

In some embodiments, the operating room 10 may include a controller 65, a keyboard 62 and a display 60 displaying a graphic user interface (GUI) 61.

Note that the display 60 displaying the GUI 61 may also be referred to herein as a surgery assistant device.

In some embodiments, the display 60 may be a screen/monitor directly accessible to the surgeon 15 and/or by a wearable display 17 (e.g., heads up display, smart glasses) directly worn by the surgeon 15 during the surgical procedure so as to provide a computer-controlled augmented reality view for the surgeon 15. The controller 65 may be communicatively coupled to any of the surgical tools used by the surgeon 15 to perform the total joint arthroplasty.

In some embodiments, the controller 65 may display on the GUI 61 of the display 60, a surgical plan to assist the surgeon 15 to perform the placement of the joint implant into the joint of the patient undergoing the total joint arthroplasty. The keyboard 62 may be used by the surgeon 15 or any other medical personnel assisting the surgeon 15 to input patient-specific data into the controller 65 via the keyboard 62 either before and/or during the total joint arthroplasty procedure such that the algorithms executed by the controller 65 may generate and/or update the surgical plan in real time so as to assist the surgeon 15 before and/or during the total joint arthroplasty procedure.

In some embodiments, the controller 65 (e.g., the I/O devices 92) may be configured to receive voice control commands and/or the display unit 60 may have touchscreen capabilities as an alternative to using the keyboard 62, where the surgeon 15 may use a pointer device, (e.g., an input device 92), for example, to activate graphical user interface elements on the GUI 61 that are programmed to allow the surgeon 15 to adjust surgical parameters via the display unit 60 during the surgical procedure, as will be shown hereinbelow.

In some embodiments not shown in FIG. 1, the controller 65 may be configured to control a surgical robotic assembly that may be used to perform the total joint arthroplasty robotically.

Figure 2:
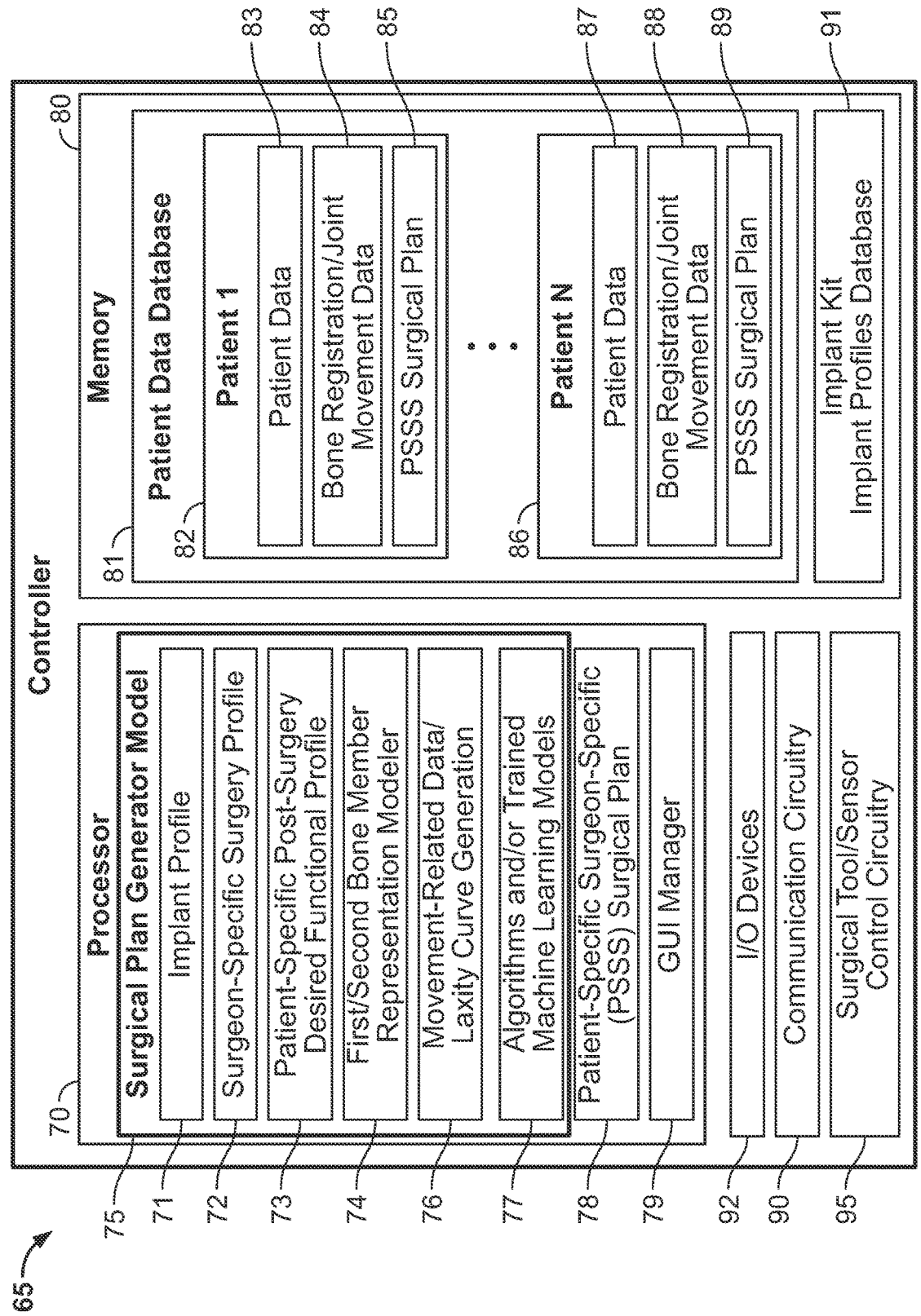
FIG. 2 is a block diagram of a controller of an improved computer-based platform for implant planning during a total joint arthroplasty in accordance with one or more embodiments of the present disclosure.

FIG. 2 is a block diagram of the controller 65 of an improved computer-based platform for implant planning during a total joint arthroplasty in accordance with one or more embodiments of the present disclosure. The controller 65 of a CAS system represented in FIG. 1 may include a processor 70, a memory 80, input and output devices 92 such as the display 60 and the keyboard 62, a communication circuitry 90, and a surgical tool and sensor control circuitry 95. The communication circuitry 90 may enable the controller 65 to communicate with other computing devices over any suitable wired and/or wireless communication network. The communication circuitry 90 may be enabled by the controller 65 to communicate with the at least one surgical tool 56A and/or with the at least one surgical probe 56B, and/or the at least one imaging camera 50 and/or with the at least one first tracker 40A and/or the at least one second tracker 40B.

In some embodiments, the surgical tool and sensor control circuitry 95 may be configured to process sensor signals from the at least one surgical tool 56A and the at least one surgical probe 56B, and/or the at least one imaging camera 50 and/or with the at least one first tracker 40A and/or the at least one second tracker 40B, and/or for any other suitable surgical devices and/or sensors needed to perform the total joint arthroscopy procedure. In other embodiments, the surgical tool and sensor control circuitry 95 may be configured to receive commands from the processor 70. The commands may be used to control the at least one surgical tool 56A and the at least one surgical probe 56B during surgery, and/or to control a robotic surgical apparatus for performing the surgical total joint arthroscopy procedure in the operating room 10.

In some embodiments, the processor 70 may be configured to execute a surgical plan generator model 75 that may include a software module 77 of algorithms, trained machine learning model (MLM), or both. The algorithms may be used for generating and/or updating the surgical plan in real time so as to assist the surgeon 15 before and/or during the total joint arthroplasty procedure. The surgical plan generator model 75 may use as inputs to the algorithm/MLM software module 77: an implant profile 71, a surgeon-specific surgery profile 72, and a patient-specific post-surgery desired functional profile 73. The surgical plan generator model 75 may use a first and second bone member representation modeler 74, and a Movement-Related Data/Laxity curve generation software module 76. The processor executing the surgical plan generator model 75 may output a Patient-Specific Surgeon-Specific (PSSS) Surgical plan 78. A GUI manager software module 79 may be configured to transmit instructions to the display 60 so as to display the PSSS Surgical Plan 78 on the GUI 61 for the surgeon 15 to view before and/or during the arthroplasty surgical procedure. All or any of the above software routines may be stored in the memory 80.

In some embodiments, any of the datasets described hereinbelow may be used to build training datasets with specific input data vectors and specific output data vectors that may be used to train machine learning models 77. Thus, the trained machine learning model 77 may be used to specifically map the input data vector to the output data vectors.

In some embodiments, the memory 80 may be configured to store a patient data database 81 storing the data from N patients, where N is an integer. The patient data database 81 may include a patient record 82 of patient 1 that includes for patient 1, patient data 83, bone registration/joint movement data 84, and a PSSS surgical plan 85. The patient data database 81 may include a patient record 86 of the Nth patient N that includes for patient N, patient data 87, bone registration/joint movement data 88, and a PSSS surgical plan 89. The memory 80 may be configured to store data for an implant kit in an implant profiles database 91, and a post-operative patients outcome database 93. The implant profiles database 91 may store a plurality of implant profiles. The post-operative patients outcome database 93 may store a plurality of patient outcome data for patients having had a plurality of arthroplasty surgical procedures.

Figure 3:
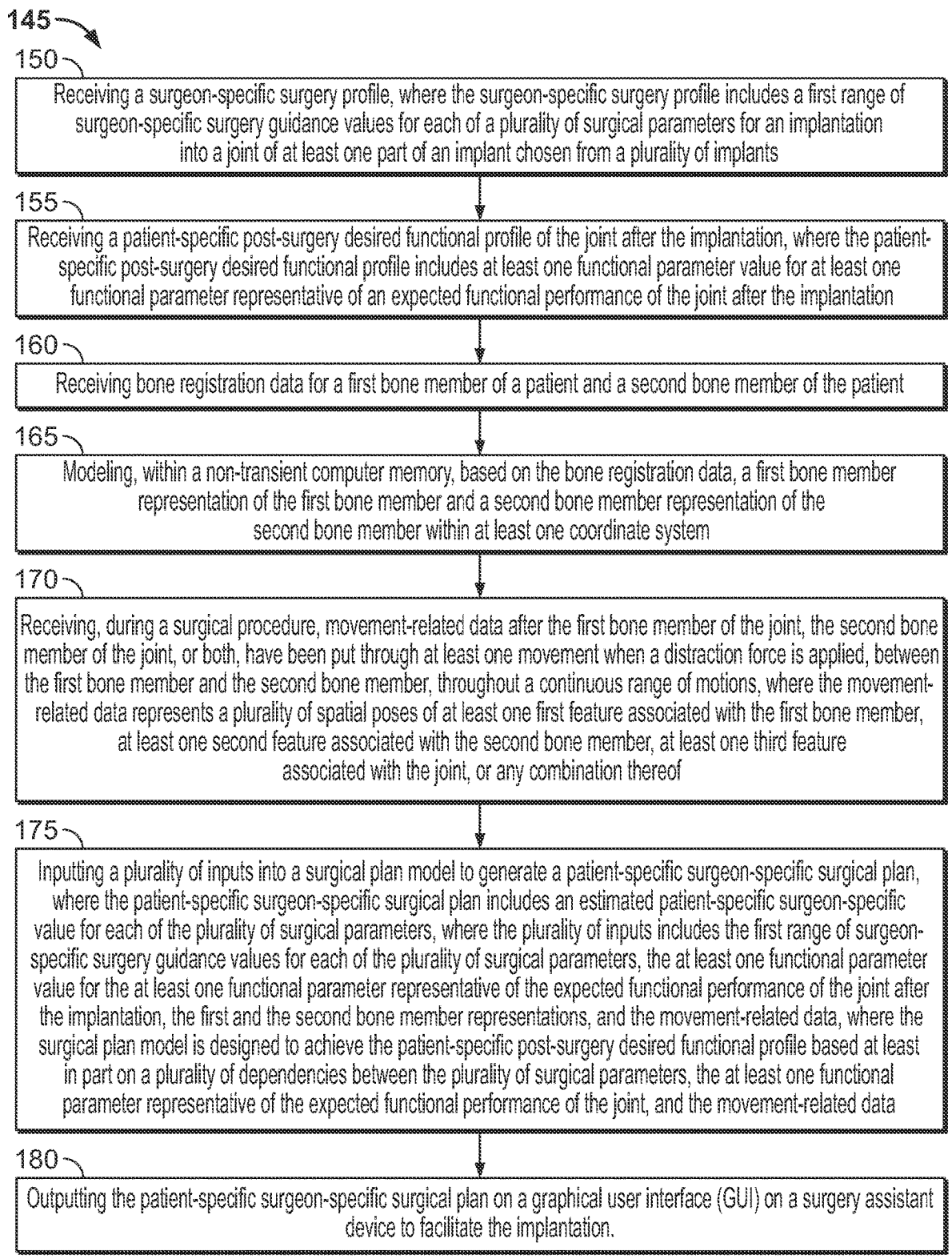
FIG. 3 is a flowchart of a method for using an improved computer-based platform for implant planning during a total joint arthroplasty in accordance with one or more embodiments of the present disclosure.

FIG. 3 is a flowchart of a method 145 for using an improved computer-based platform for implant planning during a total joint arthroplasty in accordance with one or more embodiments of the present disclosure. The method 145 may be performed by the controller 65.

The method 145 may include receiving 150 a surgeon-specific surgery profile, where the surgeon-specific surgery profile includes a first range of surgeon-specific surgery guidance values for each of a plurality of surgical parameters for an implantation into a joint of at least one part of an implant chosen from a plurality of implants.

The method 145 may include receiving 155 a patient-specific post-surgery desired functional profile of the joint after the implantation, where the patient-specific post-surgery desired functional profile includes at least one functional parameter value for at least one functional parameter representative of an expected functional performance of the joint after the implantation.

The method 145 may include receiving 160 bone registration data for a first bone member of a patient and a second bone member of the patient.

The method 145 may include modeling 165, within a non-transient computer memory, based on the bone registration data, a first bone member representation of the first bone member and a second bone member representation of the second bone member within at least one coordinate system.

The method 145 may include receiving 170 during the surgical procedure, movement-related data after the first bone member of the joint, the second bone member of the joint, or both, have been put through at least one movement when a distraction force is applied, between the first bone member and the second bone member, throughout a continuous range of motions, where the movement-related data represents a plurality of spatial poses of at least one first feature associated with the first bone member, at least one second feature of the second bone member, at least one third feature associated with the joint, or any combination thereof.

Figure 10:
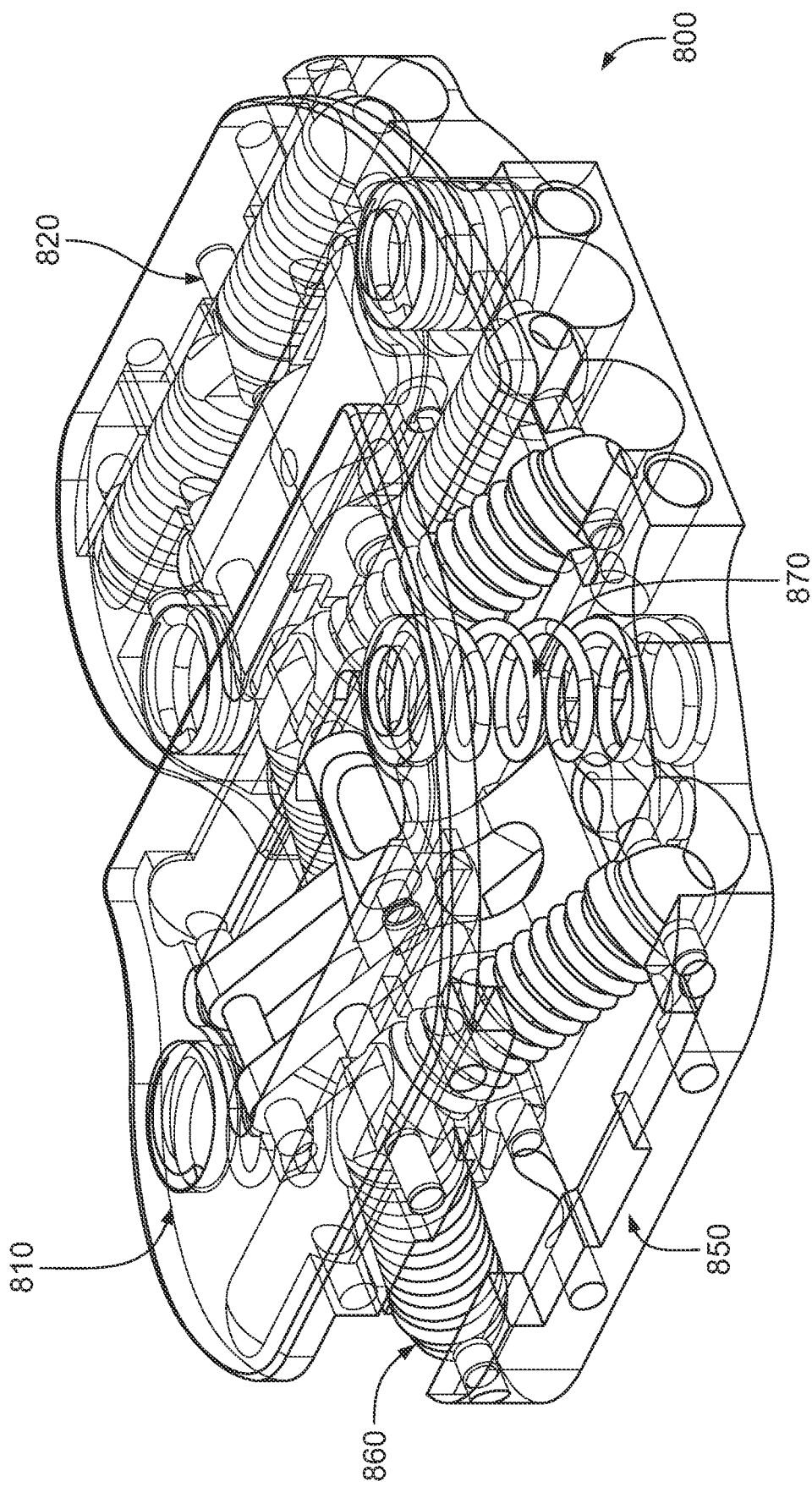
FIG. 10 shows an exemplary embodiment of a ligament balancing device in accordance with one or more embodiments of the present disclosure.

Note that any suitable tensor and/or distractor device may be used to apply a controlled, distraction force to the joint either intra-operatively or pre-surgical so as to measure the movement-related data after the first bone member of the joint, the second bone member of the joint, or both, have been put through at least one movement when the distraction force is applied between the first bone member and the second bone member throughout a continuous range of motions either non-invasively, pre-surgery or intra-operatively as the ligament balancing device 800 of FIG. 10. The movement-related data may be acquired non-invasively before the surgeon makes the incision 22 while the knee joint 20 is loaded with an external distractor device (not shown).

In some embodiments, a controlled, distraction force may be applied to the joint, independent of the measured gaps, where the controlled force may be quasi-constant or follow a distraction force application regime as described below.

In some embodiments, the distraction force may be a quasi-constant distraction force (e.g., 90 N force applied for each compartment of the knee joint). In other embodiments, the distraction force may be applied asymmetrically to the joint, for example, the applied distraction forces may be compartment-specific (e.g., 90N for the medial compartment, 70N for the lateral compartment). In yet other embodiments, the distraction force may be a controlled distraction force applied to the joint as a function of flexion angle (e.g., from 70N at 0 deg of flexion to 90N at 20 deg of flexion and then to 60N at 90 deg of flexion).

In some embodiments, the distraction force may use a control loop that may be passive and/or independent. In other embodiments, the control loop may be active and linked with the controller 65 so as to dynamically change over the series of movement.

In some embodiments, a preliminary cut may be performed by the surgeon 15 and a distractor (e.g., the ligament balancing device 800) may be placed into the joint. The distraction force may be applied by the movement of the leg from extension to flexion, or from flexion to extension, for example, in a neutral alignment. The neutral alignment may refer to the case where the distraction force applies no shear loading to the joint. In other embodiments, the leg may be moved from extension to flexion, or from flexion to extension, for example, where the distraction force is configured to apply a stress valgus force to acquire the medial gap. The leg may then be moved from extension to flexion or flexion to extension by applying a stress varus force to acquire the lateral gap, where both (medial and lateral) acquisitions may be combined to obtain the joint laxities.

In some embodiments, the distraction force may be tailored based on the specificities of the patient such as the patient's expectations in terms of post-operative activities.

The method 145 may include inputting 175 a plurality of inputs into a surgical plan model to generate a patient-specific surgeon-specific surgical plan, where the patient-specific surgeon-specific surgical plan includes an estimated patient-specific surgeon-specific value for each of the plurality of surgical parameters, where the plurality of inputs includes the first range of surgeon-specific surgery guidance values for each of the plurality of surgical parameters, the at least one functional parameter value for the at least one functional parameter representative of the expected functional performance of the joint after the implantation, the first and the second bone member representations, and the movement-related data, where the surgical plan model is designed to achieve the patient-specific post-surgery desired functional profile based at least in part on a plurality of dependencies between the plurality of surgical parameters, the at least one functional parameter representative of the expected functional performance of the joint, and the movement-related data.

The method 145 may include outputting 180 the patient-specific surgeon-specific surgical plan on a graphical user interface (GUI) on a surgery assistant device to facilitate the implantation.

In some embodiments, at the time of surgery, these CAS technologies (e.g., surgical navigation and/or robotic) may include equipment in the surgical operating room 10 such as: (1) a computer controller 65 with display functionality provided by a display 60, (2) the at least one camera 50 for defining the three-dimensional (3D) position and/or orientation within 6 degrees of freedom of trackers (40A and/or 40B) rigidly attached to patient bone members (such as the femur 30 and tibia 45), and (3) a system specific probe (e.g., the at least one surgical probe 56B) for acquiring anatomical landmarks during the registration phase. After exposure, the processor 70 may acquire the key anatomical landmarks using the probe in order to establish the relationship between the patient's anatomy and the reconstructed 3D model.

In some embodiments, these CAS technologies may be used in conjunction with other surgical instruments for facilitating the evaluation and the preparation of the bones. Once the verification of the registration is completed, the surgeon 15 may assess the soft-tissue envelope. Based on this additional intra-operative input in most cases, the surgeon 15 may choose to modify the pre-operatively established first surgical plan by inputting the soft-tissue assessment into the algorithm via the keyboard 62 or other suitable mechanism(s), which may model the impact of the soft-tissue assessment, for example, and may update the surgical plan via the surgical plan generator 75. The updated surgical plan may be displayed to the surgeon 15 on the GUI 61. Thus, the surgical instruments (e.g., cutting blocks) may be oriented and positioned to complete the preparation of the bones according to the modified surgical plan.

In some embodiments, some of these CAS technologies may be imageless and rely on intra-operative acquisitions to establish the surgical plan based on bony as well as soft-tissue references.

In some embodiments, some of the surgical instruments may include a joint tensor intended to improve the consistency in the way the joint is distracted during the assessment of the soft-tissue. Most of these devices may feature an actuator (which may be mechanical, electrical, fluid-based or any combination thereof), which may apply a distraction force between the two bones of the joint as an input while the CAS technology may track the spatial position and orientation of the two bones as an output. Then, this movement-related data may be used for the set-up of the surgical plan (for imageless technology) or modification of the surgical plan (for image-based technology). In general, joint distractors may be used at specific steps during the surgery and may require the surgeon to modify the flow of the surgeon's preferred operative technique to include this step. Finally, while the integration of joint distractors into the CAS technology allows the acquisition of relevant information related to the joint laxities, the processing of this additional data combined with usual information in terms of joint alignment and implant sizing based on bone coverage tend to add substantial cognitive burden to the surgeon during the surgery in order to define the proper surgical plan based on these numerous parametric considerations.

For example, when a total knee joint is considered, a motorized joint distractor may be configured to apply varying forces between the femoral paddle (intended to engage with the distal native femur) and the tibial paddle (intended to engage with the proximal tibial cut) depending on the flexion angle between the tibia and the femur. The surgeon may need to process a lot of surgical parameter information such as, for example, distal medial, distal lateral, posterior medial, posterior lateral femoral bone resections, the space between anterior flange of the femoral component and anterior cortex, the angle between posterior condyles of the femoral component and a reference of the native femur, the angle between the perpendicular to the distal surface of the femoral component and the mechanical axis in the sagittal plane, the angle between the perpendicular to the distal surface of the femoral component and the mechanical axis in the coronal plane, the size of the femoral component, the hip-knee-ankle angle at every 20 degrees of flexion, the space between the femoral component and the proximal tibial cut in extension and in flexion (for every 20 degrees of flexion), and/or the angle between the femur and the tibia in the sagittal plane. In this case, for example, the surgeon may need to consider at least 16 distinct parameters as listed hereinabove to establish the surgical planning for the preparation of the femoral component whereas some of these parameters may be independent and some may be interdependent. In addition, such crowded representations may not make the distinction between the impact of the different parameters on the expected functionality of the knee.

While the set-up of the surgical planning is easily manageable by the surgeon when it relates to the sizing of the components, and the alignment of the components in extension and in flexion, the set-up becomes an arduous cognitive task when the management of the laxities through the arc of motion is added to the scope of the data to be processed.

Therefore, a dilemma may exist between the number of inputs to be considered for the definition of the surgical plan and the ease of intra-operatively setting-up the surgical plan. On one hand, if a limited number of parameters (e.g., implant sizing and alignment) is considered, then the set-up of the surgical plan is easily manageable, but key parameters (e.g., soft-tissue balance) may be missing from this set-up, which may negatively impact the post-operative performance of the considered joint. On the other hand, if more parameters are considered (e.g., implant sizing, alignment, soft-tissue balance), then the set-up of the surgical plan represents a substantial cognitive burden for the surgeon during the surgical procedure. Therefore, there is a need for solutions, versatile enough, to be integrated with the surgeon's preferred surgical workflow and encompassing one or more mechanisms to facilitate the definition of the surgical planning based on component sizing, alignment, as well as soft-tissue considerations.

The embodiments disclosed herein relate to the possibility of conciliating the above-mentioned dilemma by offering an algorithm-based guidance for the definition of an optimal surgical plan leveraging all relevant total joint arthroplasty surgical parameters in terms of sizing, alignment, and soft-tissue. The approach may be based on the set-up of selected pre-operative and intra-operative inputs to guide the subsequent computation of the optimal surgical plan at the time of the surgery as well as one or more mechanisms to graphically communicate the surgical plan to the surgeon via a graphical user interface.

In some embodiments, the pre-operative inputs may be surgeon-specific. For example, a first set of pre-operative inputs may relate to the surgeon's definition of the expected objectives for the considered joint according to different surgical functional parameters (FPi; where i represents the number of considered surgical parameters). This definition may be understood as the expected signature of the joint replacement. In some cases where all of the functional parameters may not be fulfilled simultaneously, the surgeon may need to establish a hierarchy of importance between the functional parameters or groups of functional parameters organized by type of function. Such a hierarchy may be used to assign weights to each of the different surgical functional parameters FPi or a group of FPi, which may be leveraged to guide the algorithm. Note that the weight may be established under different types of format (e.g., priority levels between the FPi, and/or a percentage of importance for each FPi).

In some embodiments, as an attempt to illustrate the intent of this first set of pre-operative inputs, considering the case of a total knee arthroplasty, where the surgeon may be asked to define the following expected groups of functional objectives:

(1) Soft-tissue group: (i) Targeted difference (i.e., laxity) between medial and lateral gaps in extension, (ii) Targeted difference (i.e., laxity) between medial and lateral gaps in flexion, (iii) Targeted difference (i.e., laxity) between flexion and extension gaps, where the difference may be expressed in mm (e.g., less than 1 mm) or in percentage (e.g., less than 10%) or other suitable mechanism(s), and where the difference may be defined by a relative tightness or looseness of one joint gap compared to another (e.g., targeted extension gap of the lateral compartment being 1 mm more than the medial compartment; while targeted flexion gaps of both the lateral and medial compartments being 2 mm more than the targeted extension gap of the medial compartment. Alternatively, instead of laxity (i.e., relative tightness or looseness), the soft-tissue group may be expressed in absolute values of the gaps defined as the distance between a first bone and a second bone at different flexion angles.

Note that the although the term flexion may refer to 90 degrees of flexion, this is not by way of limitation. The term flexion may be used herein as any angle between extension and 90 degrees of flexion.

(2) Alignment group: (i) Tolerable hip-knee-ankle angle in extension, (ii) Tolerable difference of the hip-knee-ankle angle through the arc of motion, where the difference may be expressed in degrees.

(3) Sizing group: Tolerable difference between implant size and native bone size, where the difference may be expressed in implant size unit.

In some embodiments, the surgeon may be prompted to define a hierarchy between these three functionalities.

In some embodiments, the surgeon may establish several profiles of functional parameters depending on patient-related inputs (e.g., pathology, activity level, . . . ). For example, a second set of pre-operative inputs may relate to the surgeon's definition of the perceived safe range for each of the key surgical variables (SVi; where i represents the number (index) of considered surgical variables) defining the implantation of the implant(s) relative to the bone(s).

These ranges may be interpreted as tolerance bands, where the surgical variables may be allowed to float in order to achieve the functional objectives associated with each of the functional parameters associated with the first set of pre-operative inputs at the time of the processing of the intra-operative surgical plan.

Depending on the nature of the surgical variable, the range may be expressed with different types of format (e.g., in degree for an angle, in millimeter for a gap). Also, for a given surgical variable, the range of the tolerance band may be limited by the manufacturer in order to avoid a situation where the implant's performance may be at risk, such as a risk of gross misalignment, for example. In addition, some of these surgical variables may be considered in combination, such as where a first surgical variable associated with a first implant relative to a first bone should be included in a first tolerance band, a second surgical variable associated with a second implant relative to a second bone should be included in a second tolerance band, and the combination of the first and the second surgical variables should be included in a third tolerance band.

Note that the terms surgical variable and surgical parameter may be used interchangeably herein.

This second set of pre-operative inputs may be particularly advantageous when considered in combination with the first set of pre-operative inputs, as it would allow the intra-operative algorithm to establish a best-fit based on the expected functional objectives, where the tolerance bands associated with the key surgical variables may be leveraged to obtain an optimal compromise.

In some embodiments, regarding this second set of pre-operative inputs, consider a total knee arthroplasty where the intra-operative surgical planning relates to the position and orientation of the femoral component after the completion of the proximal tibial cut and the subsequent acquisition of the joint laxities, the surgeon may be then queried via the computing device (e.g., controller 65) to provide the tolerance bands for the following surgical variables via the keyboard 62 or a touchscreen display 60 that displays the GUI 61, for example.

Figure 4A:
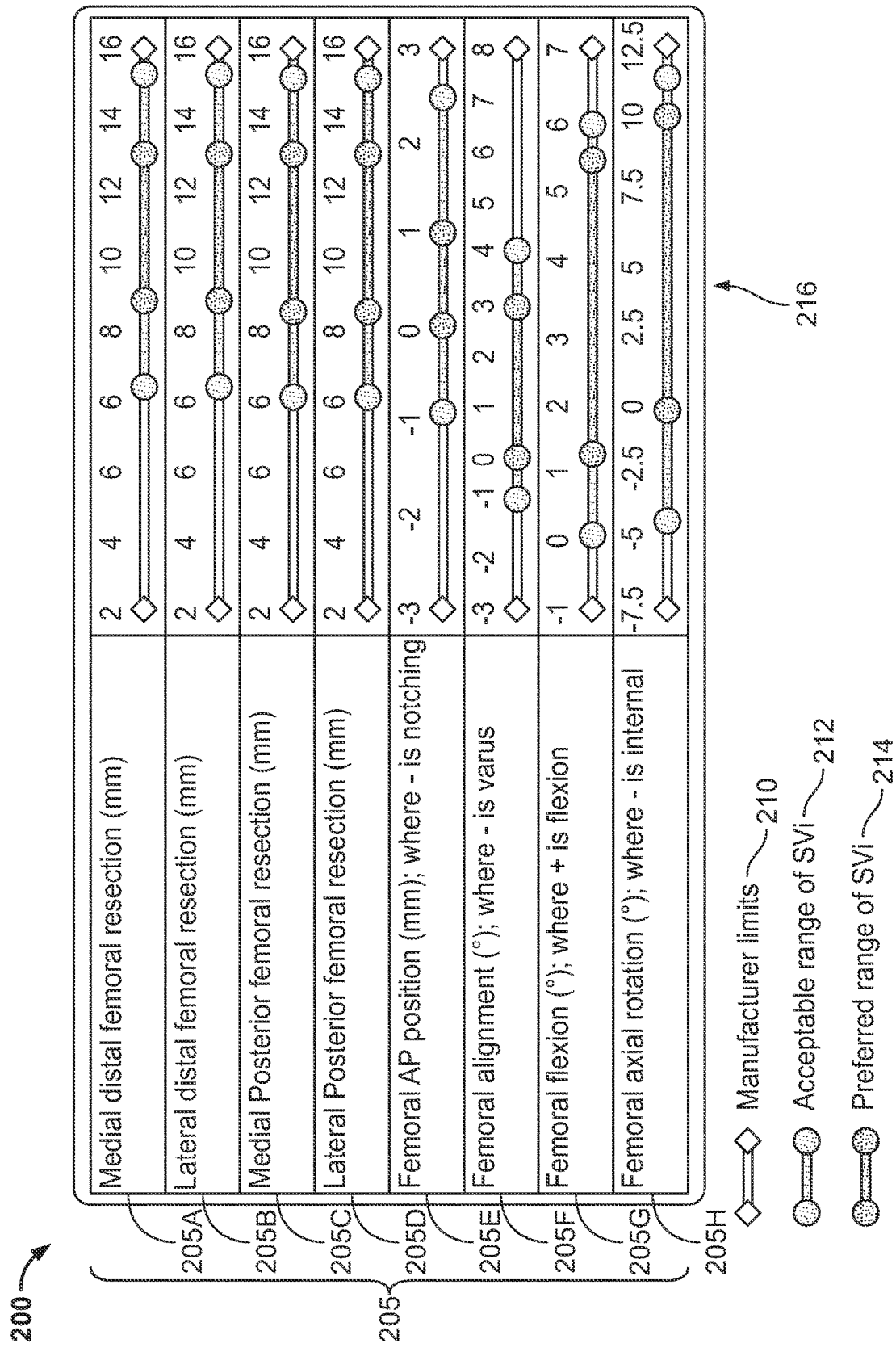
FIG. 4A illustrates a first exemplary snapshot of a graphic user interface in accordance with one or more embodiments of the present disclosure.

FIG. 4A illustrates a first exemplary snapshot 200 of the graphic user interface 61 in accordance with one or more embodiments of the present disclosure. The surgeon 15 may input into the system 10, a surgeon-specific surgery profile 72. The profile may include a range of surgeon-specific surgery guidance values for each of a plurality of surgical parameters 205 (or surgical variable). The plurality of surgical parameters 205 may include, but are not limited to a medial distal femoral resection 205A, a lateral distal femoral resection 205B, a medial posterior femoral resection 205C, a lateral posterior femoral resection 205D, a femoral antero-posterior (AP) position 205E, a femoral alignment angle 205F, a femoral flexion angle 205G, and a femoral axial rotation angle H.

Note that the terms surgical parameter and surgical variable may be used interchangeably herein.

In some embodiments, exemplary surgical parameter ranges for each of plurality of surgical parameters 205 may be displayed on the GUI 61 as shown in FIG. 4A. The range of values for each surgical parameter may be split and displayed as three subranges where a first subrange may be supplied by an implant manufacturer as manufacturer limits 210 based on a known performance of the implant system. The second and third subranges may be provided by the user (e.g., the surgeon 15) based on the surgeon's preferences and may be expressed in terms of a preferred range 214 (i.e., somewhat ideal values for the considered surgical variables) as well as in terms of an acceptable range 212 (i.e., an acceptable "comfort zone" range for the considered surgical variables). The acceptable range 212 is broader than the preferred range 214. The surgical variables 205 may be adjusted prior to the surgery based on surgeon's preference inputs (e.g., surgeon-specific surgery guidance values for each surgical parameter), and/or patient-based inputs, and/or healthcare-specific inputs as well as interactively during any time of the surgery based on additional sets of data (e.g., soft-tissue envelope tension).

Figure 4B:
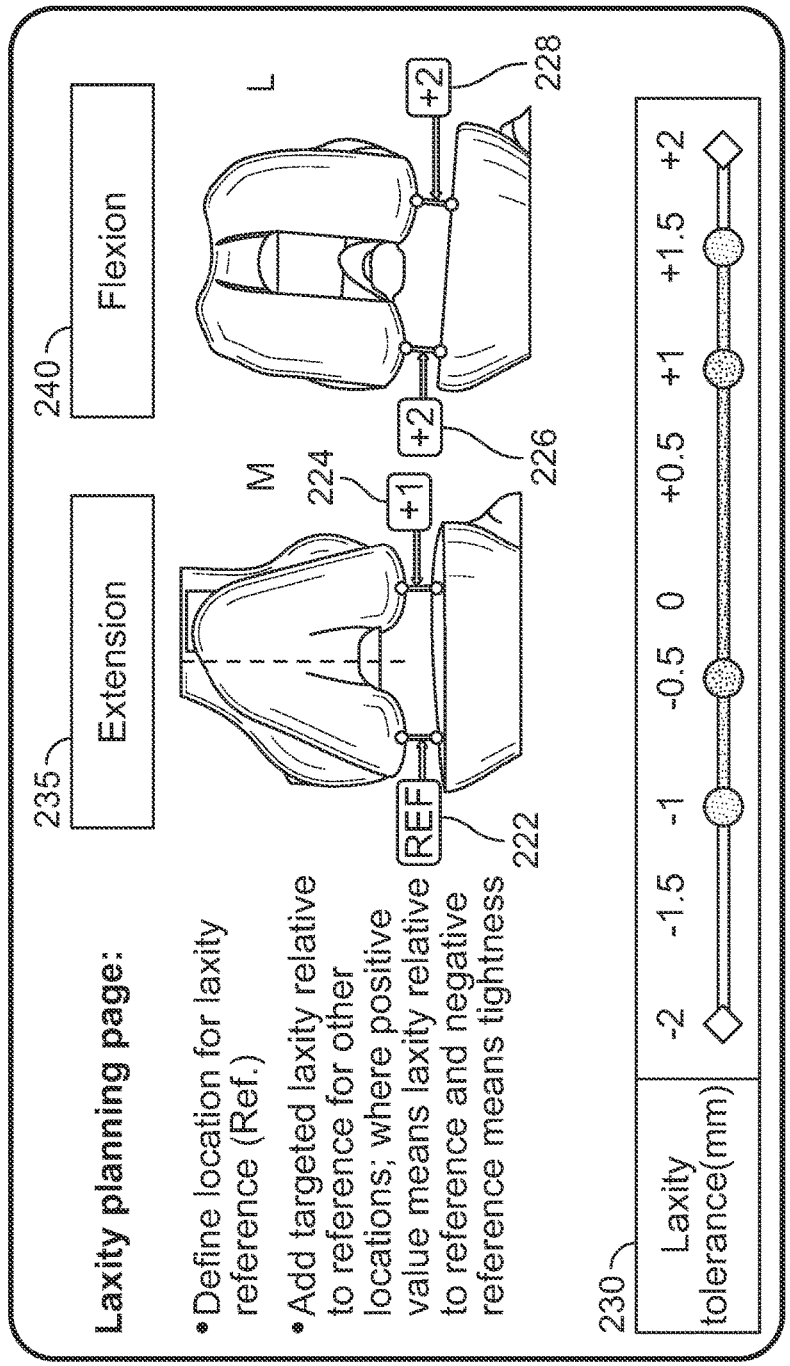
FIG. 4B illustrates a second exemplary snapshot of a graphic user interface in accordance with one or more embodiments of the present disclosure.

FIG. 4B illustrates a second exemplary snapshot 220 of the graphic user interface 61 in accordance with one or more embodiments of the present disclosure. The surgeon may enter into the system 10, the patient-specific post-surgery desired functional profile 73 that may include at least one functional parameter value for at least one functional parameter representative of an expected functional performance of the joint after implantation.

In some embodiments, FIG. 4B may show exemplary functional parameters that may be displayed to the surgeon 15 on the GUI 61. The functional parameters may relate to the expected joint laxities at different poses such as in extension 235 and in flexion 240 at 90 deg. After the selection of a reference 222 (e.g., medial compartment in extension), the other laxities may be expressed relative to the reference such as a laxity of a lateral compartment in extension 224, a medial compartment in flexion 226, and a lateral compartment in flexion 228. In other embodiments, the laxity value may be associated with a range and/or a tolerance 230, where the range and/or tolerance may be defined by the manufacturer based on a known performance of the implant system and/or by the user based on preferences. Additionally, the range and/or tolerance may be expressed in terms of the preferred range and/or tolerance (i.e., somewhat ideal values for the considered surgical variables) as well as in terms of the acceptable range and/or tolerance (i.e., acceptable "comfort zone: range for the considered surgical variables). The acceptable range and/or tolerance may be broader than the preferred range or tolerance.

In some embodiments, the at least one functional parameter may include a medial gap in extension, a medial gap in flexion at 90 degrees, a lateral gap in extension, a lateral gap in flexion at 90 degrees, and a laxity tolerance.

In some embodiments, these functional parameters may be adjusted prior to the surgery based on the surgeon's preference inputs, and/or the patient-based inputs, and/or the healthcare-specific inputs as well as the time of the surgery based on additional set of data (e.g., soft-tissue envelope tension). Finally, instead of being expressed as being relative to a reference as shown by FIG. 4B, the functional parameters may be expressed as absolute values and, in this case, more in terms of joint gaps.

For example, a third set of pre-operative inputs may relate to pre-established recommendations (e.g., pre-established by key opinion leaders, by surgical philosophy) and may encompass a pre-definition of the first and second set of inputs. In some embodiments, the pre-operative inputs may be patient-specific.

For example, a fourth set of pre-operative inputs may relate to pre-operative patient-specific information and may include, but is not limited to, age, height, weight, activity level, pre-existing conditions, comorbidities, prehab performance, health and fitness level, previous joint arthroplasty, and the like. This information may be used to fine-tune the data associated with the surgeon-specific inputs. As an attempt to illustrate the intent of this fourth set of preoperative inputs, considering a total knee arthroplasty, the surgeon may elect to fine-tune the laxities of the knee joint depending on the level of activity of the patient.

In some embodiments, the pre-operative inputs may be healthcare specific. For example, a fifth set of pre-operative inputs may relate to the type of care infrastructure (e.g., payer coverage type, hospital, or outpatient surgery center)

FIG. 5A illustrates different inputs 250 for a pre-operative surgical profile in accordance with one or more embodiments of the present disclosure. Some of the above-mentioned sets of the pre-operative inputs may be used independently or in combination, while others may be considered as being optional. The association of these set of pre-operative inputs may generate a dedicated, pre-operative surgical profile based on surgeon-specific inputs 255, patient-specific inputs 260, and/or healthcare-specific inputs 265. The set of surgeon-specific inputs may be represented herein as $\{FP_1, FP_2 \ldots \}$. The set of patient-specific inputs may be represented herein as $\{FP_I, FP_{II} \ldots \}$. The set of healthcare-specific inputs may be represented herein as $\{FP_a, FP_b \ldots \}$.

In some embodiments, the pre-operative surgical profile may be stored in the memory 80 of the controller 65 associated with a CAS technology to be used during a surgery.

In some embodiments, the surgery may use CAS technology as shown in the operating room 10 (FIG. 1) using an improved computer-based platform for implant planning during a total joint arthroplasty, as well as surgical instruments where the at least one surgical tool 56A may include a tensor to distract the soft-tissue for the acquisition of the laxities.

In some embodiments, at the time of the surgery, the CAS technology may be used to characterize the considered joint as defined by a set of intra-operative inputs including, but not limited to, data associated with the size of at least one implant, data associated with angular alignment, and data associated with soft-tissue in terms of gaps defined as the distance between a first bone and a second bone or in terms of laxity defined as a differential between gaps.

Figure 5B:
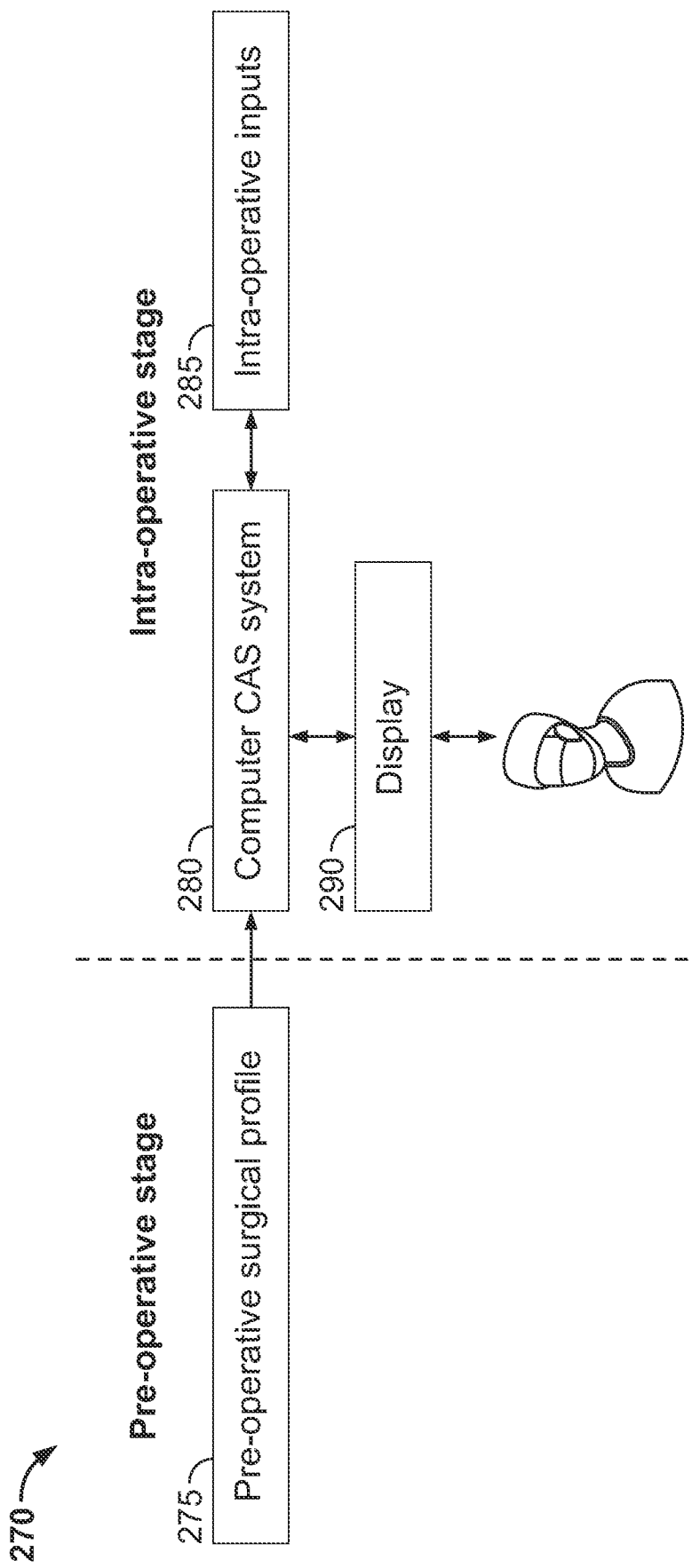
FIG. 5B illustrates a surgical flow combining both a pre-operative stage and intra-operative stage in accordance with one or more embodiments of the present disclosure.

FIG. 5B illustrates a surgical flow 270 combining both a pre-operative stage and intra-operative stage in accordance with one or more embodiments of the present disclosure. The pre-operative stage may include processor 70 acquiring a pre-operative surgical profile 275. The intra-operative stages may include the controller 65 of the computer CAS system 280 receiving the pre-operative surgical profile 275. The computer CAS system 280 may be controlled using the controller 65. Both the pre-operative surgical profile 275 and intra-operative inputs 285 may be combined to feed the algorithm and/or trained machine learning models 77 in the surgical plan generator model 75 of FIG. 2, which may output an updated PSSS surgical plan 78 from the surgical plan generator 75 on a display 290 (e.g., GUI 61 on the display 60 of FIG. 1) to display for the surgeon 15, and may include the subsequent steps to be performed during the surgery.

In some embodiments, the parameters and data shown in FIGS. 5A and 5B may be inputs that are inputted into the surgical plan generator model 75 to generate the patient-specific surgeon-specific surgical plan 78.

Figure 48:
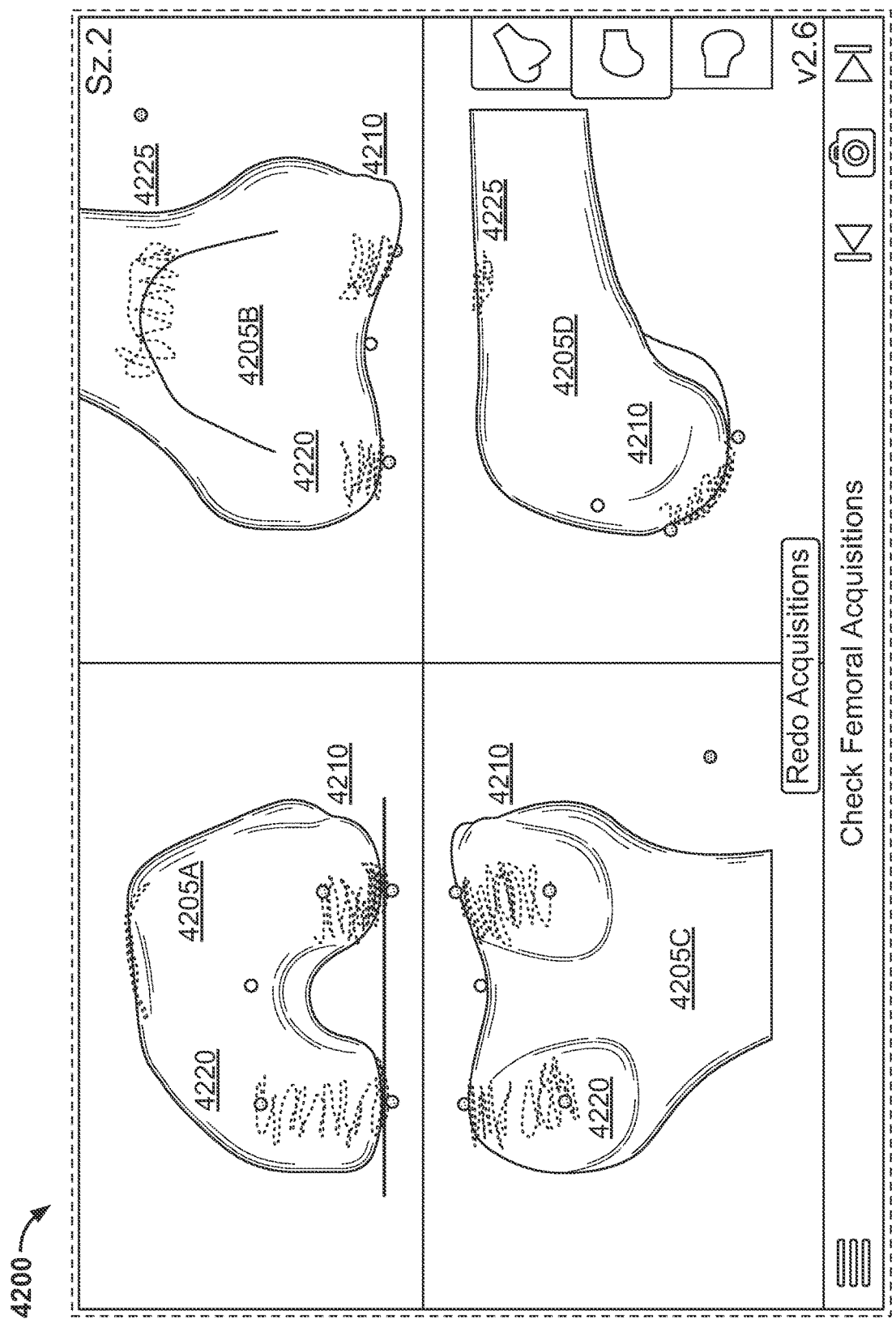
FIG. 48 illustrates a snapshot of graphic user interface displaying a second bone member representation in accordance with one or more embodiments of the present disclosure.
Figure 49:
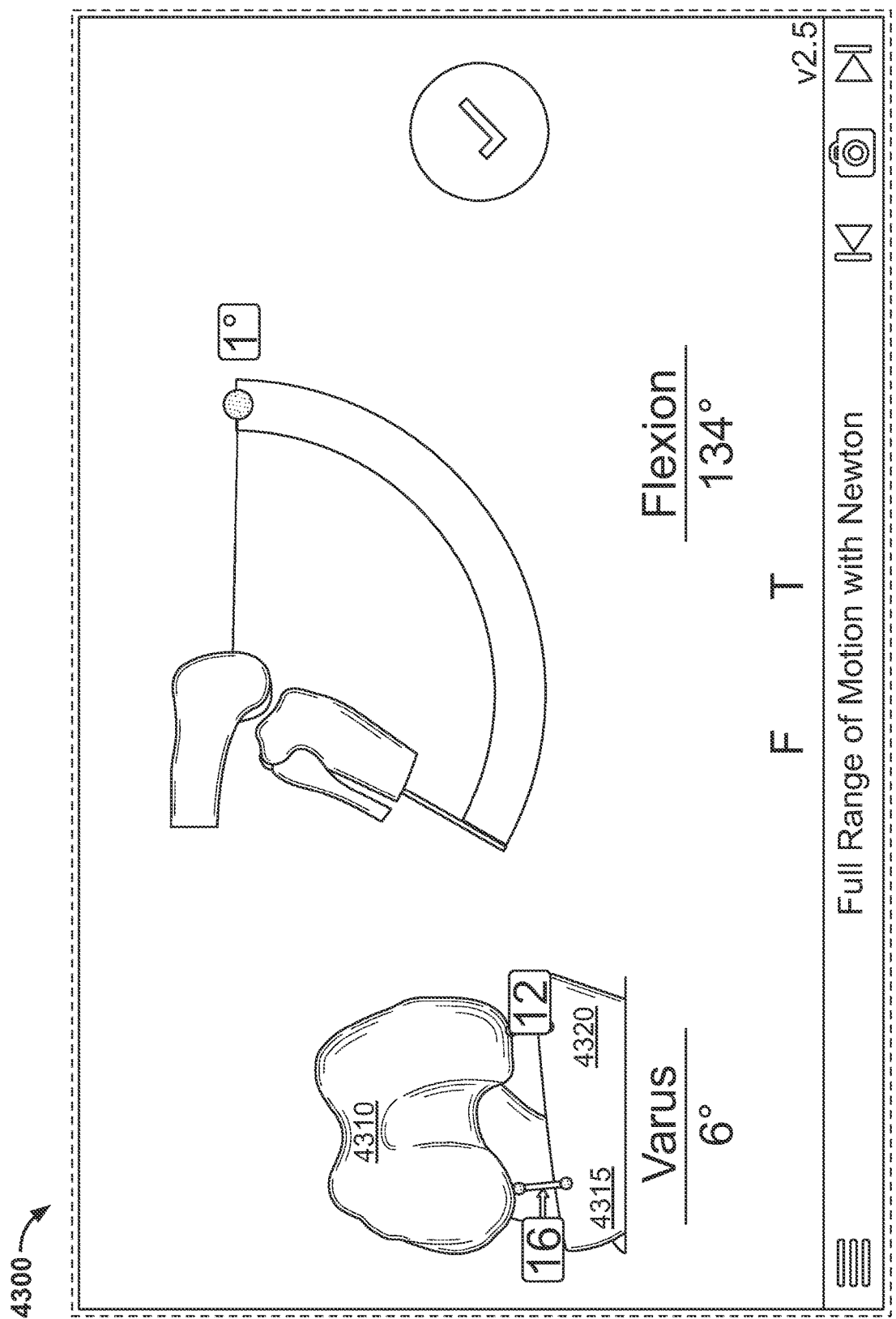
FIG. 49 illustrates a snapshot of a graphic user interface displaying the acquired movement-related data in accordance with one or more embodiments of the present disclosure.
Figure 50:
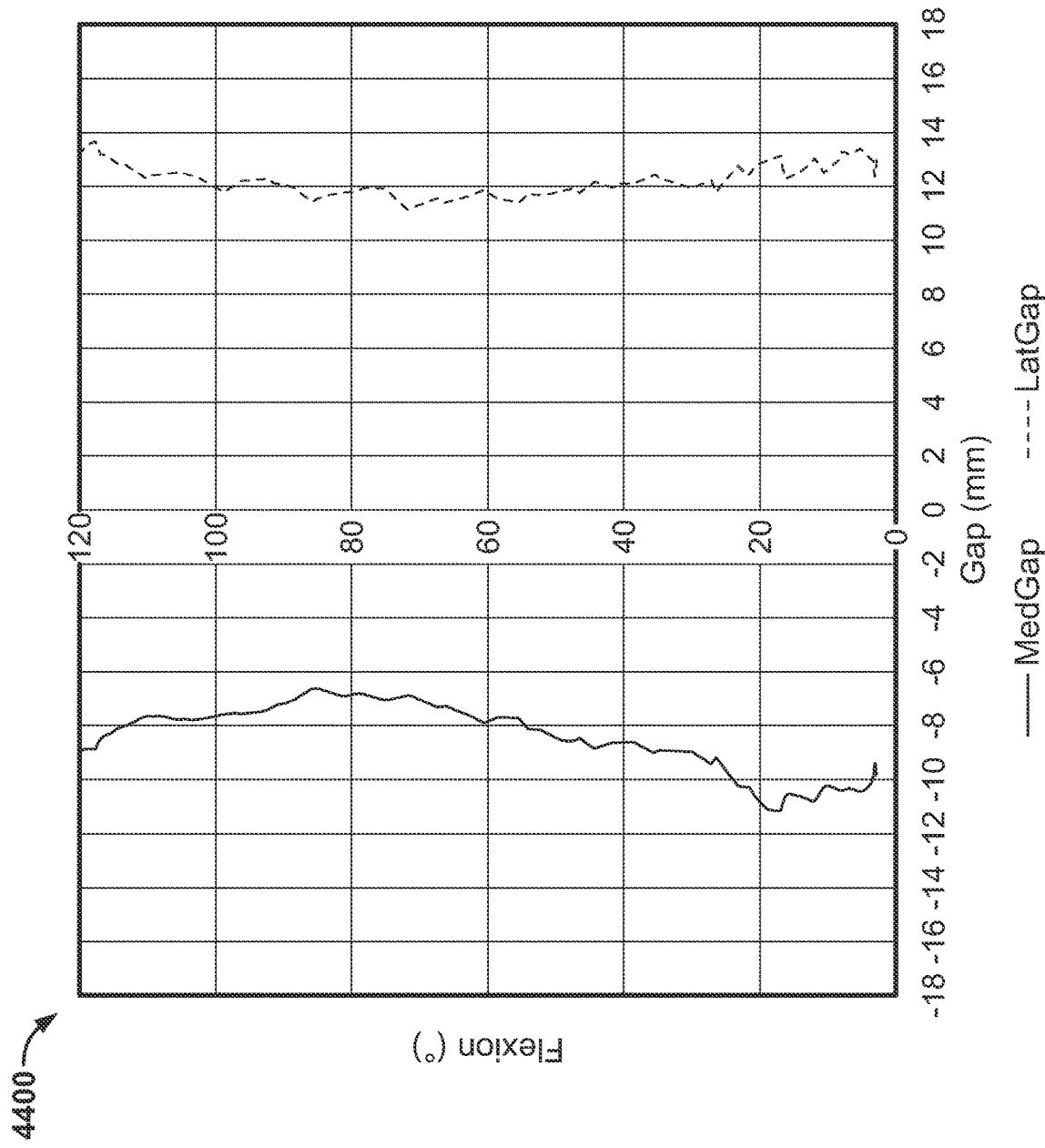
FIG. 50 is a graph of a laxity curve showing the measured medial gap and lateral gap over a range of flexion angles in accordance with one or more embodiments of the present disclosure.

In some embodiments, a plurality of inputs to the surgical plan generator model 75 may include, but are not limited to an implant profile of the implant chosen from the plurality of implants, the first range of surgeon-specific surgery guidance values for each of the plurality of surgical parameters (see FIG. 4A), the at least one functional parameter value for the at least one functional parameter representative of the expected functional performance of the joint after the implantation (see FIG. 4B), the first and the second bone member representations (see FIGS. 47 and 48), and the movement-related data for acquiring the laxity curves (see FIGS. 49 and 50).

Figure 6:
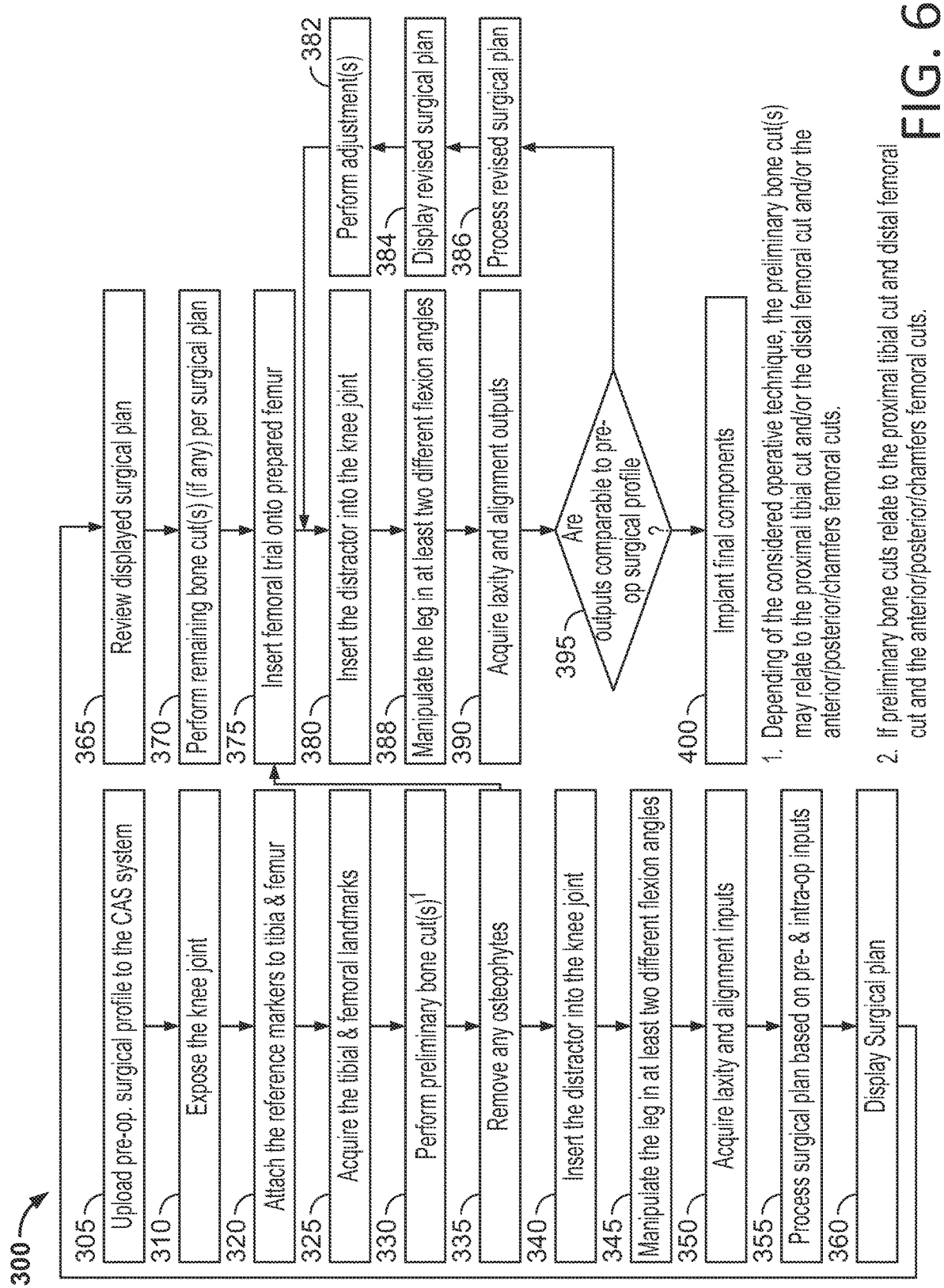
FIG. 6 is a flowchart of an exemplary surgical flow of performing a total knee arthroplasty in accordance with one or more embodiments of the present disclosure.

FIG. 6 is a flowchart 300 of an exemplary surgical flow of performing a total knee arthroplasty in accordance with one or more embodiments of the present disclosure. The exemplary surgical flow of FIG. 6 is one embodiment of the method of FIG. 3. In the exemplary surgical flow of FIG. 6, the distraction force may be applied by an in-situ distractor device placed inside the knee after the surgeon 15 has made the incision 22 in the knee joint 20. The surgical flow may include, once the preparation of the bones performed, placing trial implants. The surgeon may perform a trial reduction to acquire a post-cut signature of the joint, which may be compared to the expected functional parameters. In case of a discrepancy, the algorithm may offer options intended to decrease the deviation level.

In some embodiments, the steps of the exemplary surgical flow as performed by the surgeon 15 is shown in the flowchart 300. The exemplary surgical flow may include the surgeon 15 uploading a pre-operative surgical profile to the CAS system in a step 305. In a step 310, the surgeon may expose the knee joint via the incision 22 in the knee joint 20. In a step 320, the surgeon 15 may attach the reference markers 40A and 40B respectively to the femur 30 and the tibia 45. In a step 325, the processor 70 may acquire tibial and femoral landmarks. In a step 330, the surgeon 15 may perform preliminary bone cut(s). Depending on the considered operative technique, the preliminary bone cut(s) may relate to the proximal tibial cut and/or the distal femoral cut and/or the anterior/posterior/chamfers femoral cuts.

In some embodiments, in a step 335, the surgeon 15 may remove osteophytes. If the preliminary bone cuts may relate to the proximal tibial cut and the distal femoral cut and the anterior/posterior/chamfers femoral cuts, then the surgical flow continues to a step 375. If the preliminary bone cuts may relate to the proximal tibial cut, then in a step 340, the surgeon 15 may insert a distractor device into the knee joint. In a step 345, the surgeon 15 may manipulate the leg in at least two different flexion angles. The range of motions captured by the processor 70 via the reference markers 40A and 40B during the manipulation of the leg may be referred to as spatial poses. In a step 350, the processor 70 may acquire laxity and/or alignment inputs. In a step 355, the processor 70 using the surgical plan generator module 78 may process the surgical plan based on the pre-operative and intra-operative inputs. In a step 360, the processor 70 executing the GUI manager 79 may cause the GUI 61 to display the surgical plan on the display 60. The surgeon 15 may review the displayed surgical plan in a step 365. In a step 370, the surgeon 15 may perform the remaining bone cut(s) per the surgical plan.

In some embodiments, in the step 375, the surgeon 15 may insert the femoral trial onto the prepared femur. In a step 380, the surgeon 15 may insert the distractor into the knee joint 20 to apply a distraction force. In a step 388, the surgeon 15 may manipulate the leg of the patient in at least two different flexion angles (e.g., an embodiment of a plurality of spatial poses) while the processor 70 acquires the movement-related data via the reference markers 40A and 40B. In a step 390, the processor 70 may acquire laxity and/or alignment outputs. In a decision step 395, the processor 70 may assess whether the outputs of the step 390 are comparable to the pre-operative surgical profile. If so, the surgeon 15 may implant the final components in a step 400. If not, the processor 70 in a step 386 may process a revised surgical plan. In a step 384, the processor 70 via the GUI manager 79 may cause the GUI 61 to display on the display 60, the revised surgical plan. The surgeon 15 may perform adjustment(s) in a step 382 and the surgeon 15 may the insert the distractor into the knee joint 20 in the step 380.

In some embodiments, the controller 65 may be configured to input a plurality of inputs into a surgical plan model 75 to generate a patient-specific surgeon-specific surgical plan 78. The plurality of inputs may include, but are not limited to: an implant profile of the implant chosen from the plurality of implants, the first range of surgeon-specific surgery guidance values for each of the plurality of surgical parameters, the at least one functional parameter value for the at least one functional parameter representative of the expected functional performance of the joint after the implantation, the first and the second bone member representations, the movement-related data, or any combination thereof.

In some embodiments, the surgical plan model 75 may be designed to achieve the patient-specific post-surgery desired functional profile 73 based at least in part on a plurality of dependencies between the plurality of surgical parameters 205, the plurality of implant profiles, the at least one functional parameter representative of the expected functional performance of the joint, the movement-related data 76, or any combination thereof. The patient-specific surgeon-specific surgical plan may include an estimated (proposed) patient-specific surgeon-specific value for each of the plurality of surgical parameters outputted by the surgical plan generator model 75.

In some embodiments, the controller 65 may be configured to output the patient-specific surgeon-specific surgical plan 78 on the graphical user interface (GUI) 61 on a surgery assistant device 60 to facilitate the implantation.

In some embodiments, the patient-specific surgeon-specific (PSSS) surgical plan 78 may be displayed to the surgeon 15 on the GUI 61 using a variety of different formats. A first format may relate to the display of basic key indicators regarding the fulfillment level of each FPi (where the fulfillment level may be quantitative or qualitative) and eventual warning messages. A second format may relate to an advanced display of all the parameters, where the surgeon may perform adjustments of the SVi either by the keyboard 62 or on a touchscreen display 60 or through voice control commands and may evaluate their impact on the FPi.

Figure 7:
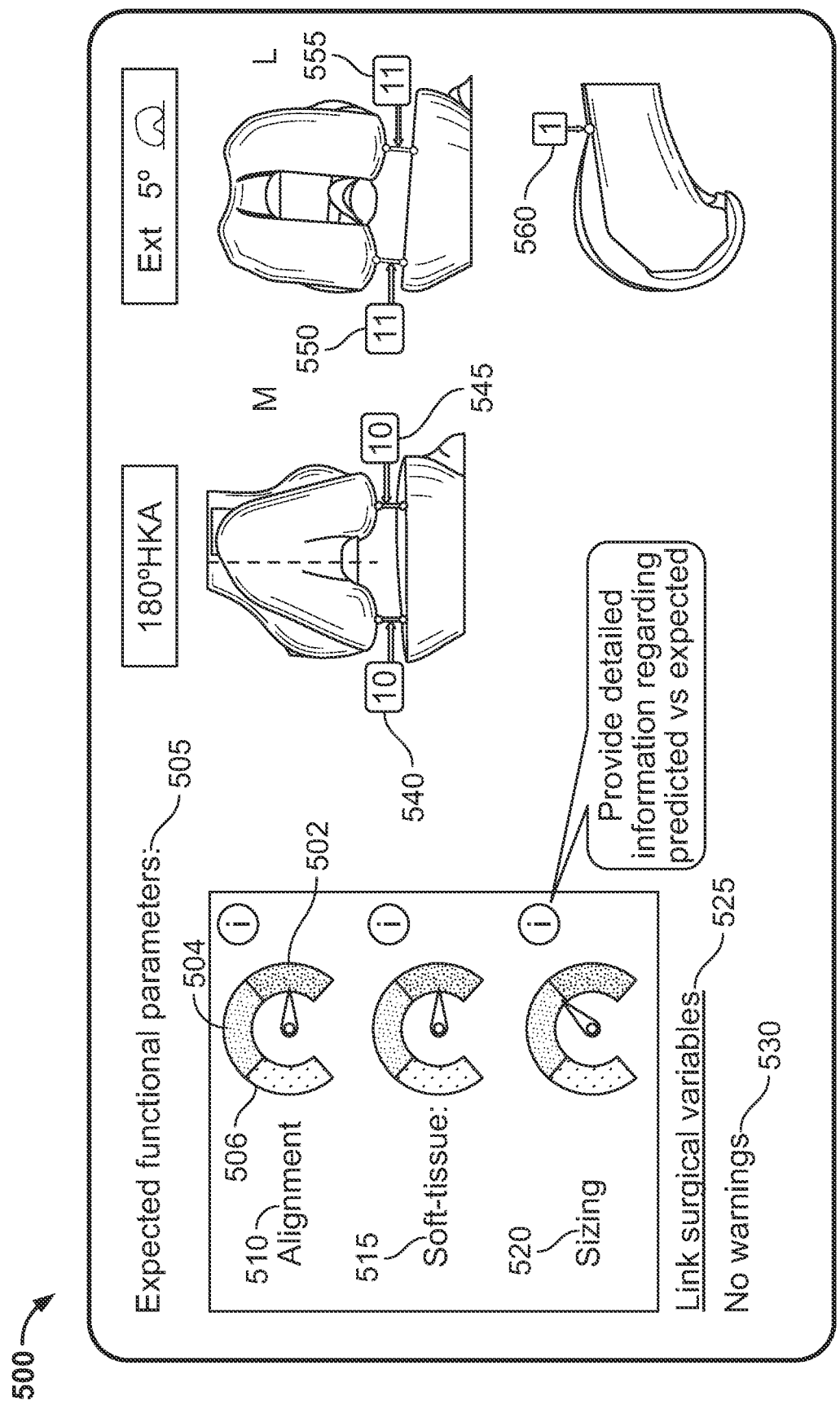
FIG. 7 is a first exemplary snapshot of a patient-specific surgeon-specific surgical plan displayed on a graphic user interface in accordance with one or more embodiments of the present disclosure.
Figure 8:
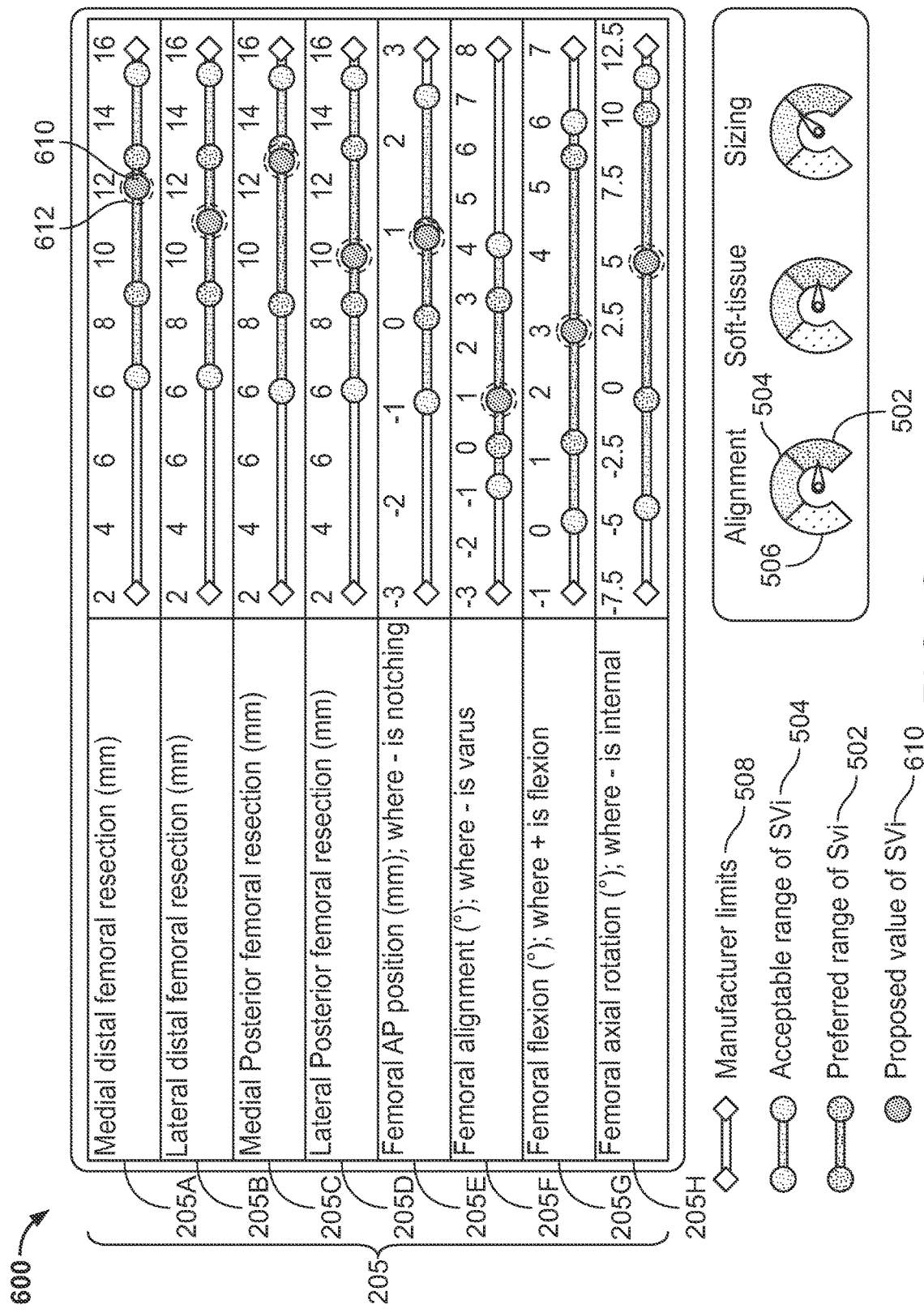
FIG. 8 is a second exemplary snapshot of a patient-specific surgeon-specific surgical plan displayed on a graphic user interface in accordance with one or more embodiments of the present disclosure.

FIGS. 7 and 8 may be exemplary embodiments of the outputted PSSS surgical plan 78 from surgical plan generator model 75.

FIG. 7 is a first exemplary snapshot 500 of the PSSS surgical plan 78 displayed on the GUI 61 in accordance with one or more embodiments of the present disclosure. FIG. 7 illustrates a dashboard of expected functional parameters 505 the representation of the key indicators showing the predicted fulfillment of the FPi for a total knee arthroplasty. The dashboard of expected functional parameters 505 may be used during most of the surgical procedure where the surgical plan generator model 75 may generate an optimal PSSS surgical plan based on the plurality of inputs from FIGS. 4A and 4B, for example. The surgical plan generator model 75 may compute an estimated patient-specific surgeon-specific value for each of the surgical parameters 205.

In some embodiments, the GUI 61 may display the model generated predicted laxity values: a medial component laxity value 540 in extension (e.g., 10 mm), a lateral component laxity value 545 in extension (e.g., 10 mm), a medial component laxity value 550 in flexion (e.g., 11 mm), and a lateral component laxity value 555 in extension (e.g., 11 mm) as well as an alignment parameter 560 (e.g., 1 mm).

In some embodiments, the dashboard of expected functional parameters 505 may include at least one indicator indicating a fulfillment of functional parameters such as an alignment indicator 510, a soft-tissue indicator 515, and a sizing indicator. If the estimated patient-specific surgeon-specific value for each of the alignment surgical parameters, for example, fall within a preferred range of values 502, the arrow of the indicator may point to the preferred range 502 of values. The arrow may point to the acceptable range 504 or to an indication that the surgical variables are outside 506 of the acceptable range. If all indicators indicate that estimated patient-specific surgeon-specific value for each of the surgical parameters are within the preferred range 502, a "No Warnings" indication 530 may be displayed. If any of the surgical variables are outside of the acceptable range, a warning may be given on the GUI 61. Subsequently, the user may click on the link called "Link to surgical variables" 525 change to the surgical variable page as shown below in FIG. 8.

FIG. 8 is a second exemplary snapshot 600 of the PSSS surgical plan 78 displayed on the GUI 61 in accordance with one or more embodiments of the present disclosure. FIG. 8 shows the output from the surgical plan generator model 75 as the PSSS surgical plan 78. However, the surgical parameters 205 may not be only displayed with ranges of surgical parameter values that include a manufacturer limit range 508, the acceptable range 504, and the preferred range 502, but the computed estimated patient-specific surgeon-specific value 610 may be displayed for each of the surgical parameters 205.

In some embodiments, if the surgeon uses the proposed (estimated) values 610 of each surgical variable 205 generated by the surgical plan generator model 75 during the arthroplasty surgical procedure, the predicted functional performance of the joint (e.g., the laxity values shown in FIG. 7 may be achieved.

In some embodiments, the controller 65 may be configured to generate a plurality of interactive GUI interface elements 612 as shown in the dotted circle that are programmed to allow a user to adjust the estimated patient-specific surgeon-specific value for at least one surgical parameter from the plurality of surgical parameters displayed on the GUI by using a pointer or any other input device to move an interactive GUI interface element on the display.

In some embodiments, the controller 65 may be configured to receive an input from any of the plurality of interactive GUI interface elements to a respective surgical parameter of the plurality of surgical parameters. The controller may then be configured to update, based on the surgical plan model 75 and the input from the input device, at least one other interactive GUI interface element corresponding to the estimated patient-specific surgeon-specific value for at least one other surgical parameter from the plurality of surgical parameters.

FIG. 8 illustrates an example of the representation of the SVi and the impact of their adjustment on the prediction of the FPi for a total knee arthroplasty. Thus in other embodiments, the algorithm and/or machine learning models 77 may be configured to provide guidance to the surgeon 15 in terms of providing various surgical options to achieve the desired function of the joint. Such options may include, for example, a recut of a first bone or a second bone with a change of the position and/or orientation of the initial cut, change of the size of the implant, change of the alignment, change of the soft-tissue balance, and/or release of a component within the soft-tissue envelope.

In some embodiments, the surgical flow may be versatile regarding the sequences of preparation of the bone, where the set of intra-operative inputs may include, but are not limited to, data associated with the size of at least one implant, data associated with angular alignment, and/or data associated with soft-tissue laxity obtained after the partial preparation of a first bone, after the preparation of a first bone, after the preparation of a first bone and the partial preparation of a second bone, or after the preparation of both a first bone and a second bone.

Figure 9:
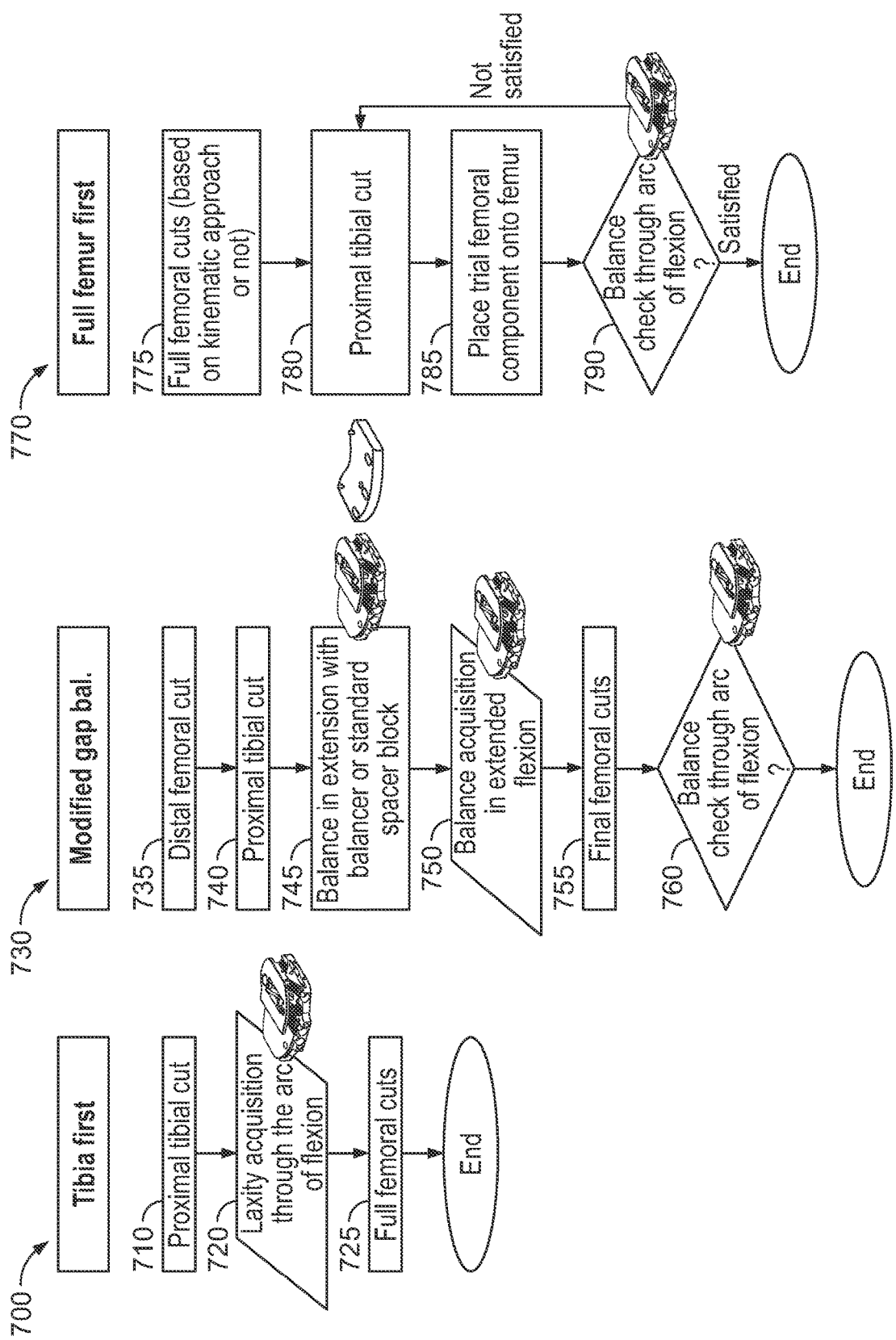
FIG. 9 illustrates three flowcharts for comparing different types of known operative techniques in accordance with one or more embodiments of the present disclosure.

FIG. 9 illustrates three flowcharts for comparing different types of known operative techniques in accordance with one or more embodiments of the present disclosure. In a first flowchart 700 of a tibia first surgical flow, the surgeon 15 may perform a proximal tibial cut in a step 710. In a step 720, laxity acquisition though the arc of flexion (e.g., movement-related data) may be acquired. In a step 725, the surgeon 15 may perform full femoral cuts.

In some embodiments, in a second flowchart 730 of a modified gap balancing surgical flow, the surgeon 15 may perform a distal femoral cut in a step 735. The surgeon may perform a proximal tibial cut in a step 740. In a step 745, the surgeon 15 may balance the knee joint 20 in extension with a balancer or standard spacer block. In a step 750, the surgeon 15 may balance acquisition in extended flexion. In a step 755, the surgeon 15 may perform the final femoral cuts. In a decision step 760, the surgeon 15 may perform a balance check through the arc of flexion.

In some embodiments, in a third flowchart 770 of a full femur first surgical flow, the surgeon 15 may perform full femoral cuts in a step 775 that may or may not be based on a kinematic approach. In a step 780, the surgeon 15 may perform a proximal tibial cut. In a step 785, the surgeon 15 may place a trial femoral component onto the femur. In a decision step 790, the surgeon 15 may perform a balance check through the arc of flexion. If the surgeon is satisfied, the surgery is finished. If the surgeon is not satisfied, the surgeon 15 may continue to perform the proximal tibial cut in the step 780.

In some embodiments, the disclosed total joint arthroplasty techniques described herein may be applied to a total shoulder, hip, ankle, total knee, lateral partial knee and/or medial partial knee arthroplasty surgical procedure.

In some embodiments, the display of the SVi as shown in FIG. 4A may be used at the time of the surgery so as to let the surgeon intra-operatively adjust them in order to achieve a proper function of the considered joint. When the number of SVi are limited (e.g., size and alignment inputs), the surgeon may cognitively process them and adjust them intra-operatively on-the-fly to achieve the proper function of the joint under consideration. On the other hand, if the number of SVi is too large (e.g., size, alignment, and soft-tissue inputs), which may be needed to gain better understanding of the joint, then the cognitive burden may be too high on the surgeon and too time consuming on the surgeon for adjusting them during surgery.

In contrast, the embodiments disclosed herein rely on a pre-operative surgical profile that is surgeon-specific regarding the targeted function of the considered joint (FPi) and the acceptable range of the SVi in addition to patient-specific and healthcare-specific inputs combined with intra-operative inputs regarding the characterization of the considered joint during the procedure. To solve these technical problems when the number of surgical parameters are too high for the surgeon 15 to cognitively process, the processor 70 may use the algorithm and/or trained machine learning models 77 (e.g., mathematical-based or machine learning-based), where these inputs may be translated into the patient-specific surgeon-specific surgical plan 78 for the completion of the bone cut(s) in order to achieve the expected FPi, while keeping the SVi within their assigned tolerance bands. In case of issues and/or warnings such as when there may be no result based on the inputs, the algorithm may display alternative results. The display of the surgical plan under the format of the functional parameters (e.g., alignment, soft-tissue, size) being expressed as key indicators may be a key aspect of the embodiments disclosed herein.

FIG. 10 shows an exemplary embodiment of a ligament balancing device 800 in accordance with one or more embodiments of the present disclosure. The ligament balancing device 800 shows an example of a tensor or a distractor device for applying a distraction force between the two bones of the joint, in this exemplary embodiment, the knee joint. In the ligament balancing device 800, the spring families 860, 870 cooperate to maintain a substantially constant axial distraction force between the first plate 810 or 820 for interfacing with the femoral medial and lateral condyles, and the second plate 850 for interfacing with the tibia regardless of the distance/height between the first plate 810 or 820 and the second plate 850. The distraction force may be applied by the axial springs 870 along the range of motion of the first plate 810 or 820 to the bone members of the joint for enabling the measurement of movement-related data of the joint.

The exemplary embodiment of the intra-operative distractor device (e.g., the ligament balancing device 800) as shown in FIG. 10 is merely for visual and conceptual clarity and not by way of limitation of the embodiments disclosed herein. Any suitable tensor and/or distractor device may be used to apply the distraction force to the joint either intra-operative or pre-surgery so as to measure the movement-related data after the first bone member of the joint, the second bone member of the joint, or both, have been put through at least one movement when the distraction force is applied between the first bone member and the second bone member throughout a continuous range of motions either non-invasively, pre-surgery or intra-operatively as the ligament balancing device 800 of FIG. 10.

As an attempt to simplify the set-up of the intra-operative surgical plan, there may a tendency to pre-define the parameters used as inputs/references for the set-up of the surgical plan. Lack of control of these parameters may impact the inputs and references used for the surgical planning and thus the definition of the surgical plan itself. During a total knee arthroscopy (TKA) procedure, for example, the surgeon may collect the laxities of the knee joint under distraction force applied by the tensor, or distractor device, through the arc of motion. The measured laxities may be used to set-up a surgical plan in which the surgical plan typically references the joint gaps in "extension" and in "flexion". However, there is a lack of consistency regarding the definition of extension as an input for the surgical plan. Some implant manufacturers may arbitrarily recommend performing the acquisition in extension at 5° of flexion. Other manufacturers may recommend performing the acquisition in extension at 10° of flexion as it may decrease the mid-flexion instability, but may lead to a flexion contracture requiring a release of the posterior capsule. Finally, some manufacturers make no recommendation for the acquisition in extension leading to a vast range of angles (e.g., 4.5±10.3°) as per the embodiments disclosed herein.

In some embodiments, a definition for a patient-specific extension angle may leverage investigational studies, where it was observed that during the final straightening of the leg, due to the combined action of the posterior capsule and the medial co-lateral ligament, the joint gaps that were measured under constant distraction force tend to substantially decrease.

FIGS. 11A and 11B illustrate laxity curves 900 and 920 for two patients in accordance with one or more embodiments of the present disclosure. As shown in FIG. 11A for patient A and FIG. 11B for patient B, both the magnitude of the change (Y-axis) of the joint gap as well as the flexion angle (X-axis) where the inflection point occurs (see orange dot in FIG. 12B) may tend to be patient specific. The extension angle may be defined based on the treatment and/or on the processing of the laxity curves to use a personalized input for the set-up of the surgical plan.

Figure 12C:
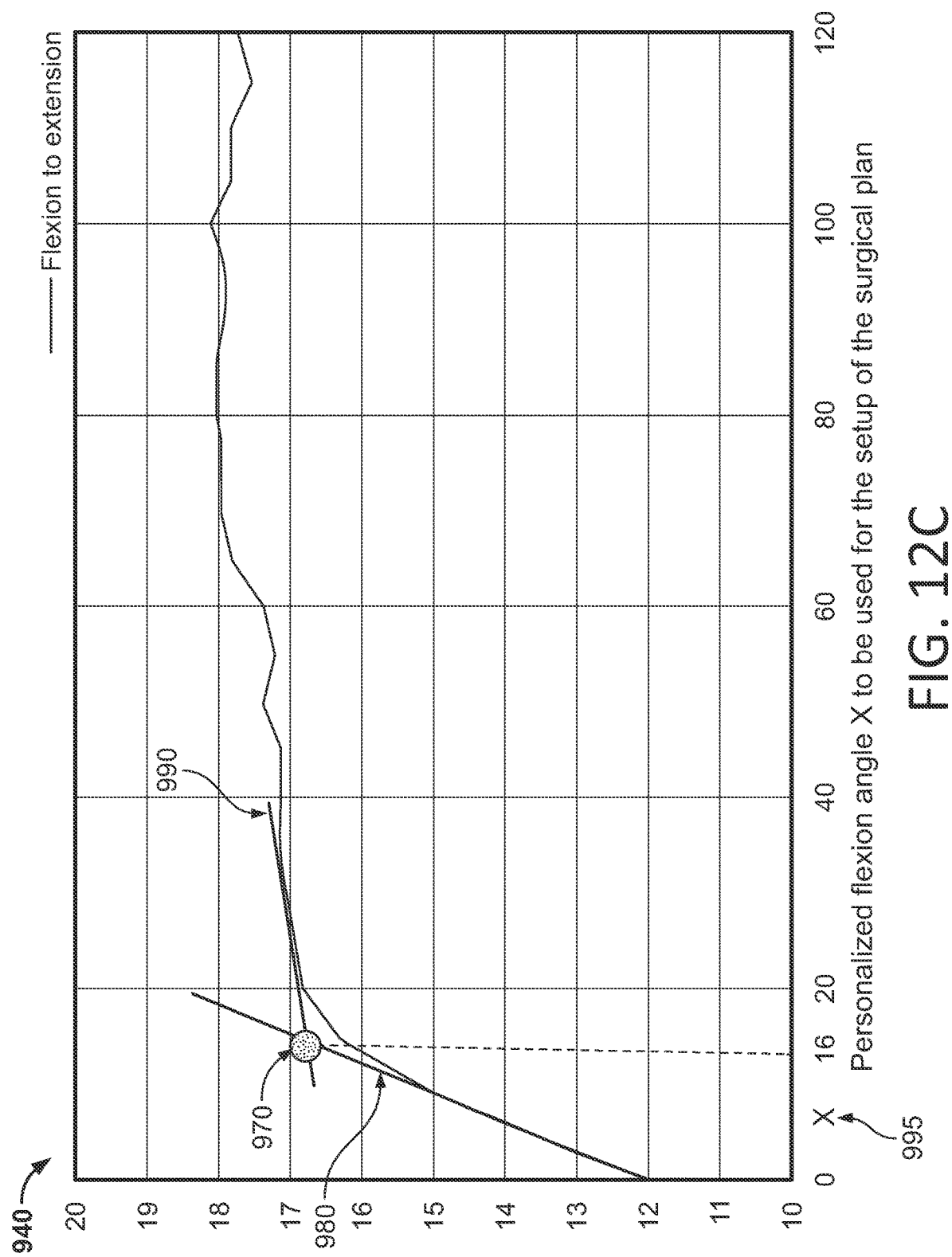

FIGS. 12A-12C illustrate a flow for modeling joint laxity curves in accordance with one or more embodiments of the present disclosure. For example, as shown in FIG. 12A, during the early flexion (e.g., from max. extension to 20°), two portions of the laxity curve 940 may be identified based on their slope (i.e., $\Delta Y/\Delta X$) as shown in the two rectangles 945 and 950. A linear regression may be applied to each portion. The point of discontinuity which there is a change in slope as defined as the intersection between lines 980 and 990 is identified by a circle 970 in FIGS. 12B and 12C corresponding to a flexion angle of 16 degrees. The personalized flexion angle X may be expressed as fraction of this angle (e.g., half of the identified angle). In some embodiments, to the personalized flexion angle X may be obtained by using a corpus of patient-specific data, such as for example, from cadaveric knees as shown in the following figures.

Note that the term patient-specific benchmark parameter may refer to, but is not limited to, the parameters of the laxity curve (e.g., joint gap versus joint angle). Note that the term patient-specific benchmark parameter may refer to, but is not limited to, the personalized flexion angle X, for example, that may be used for the setup of the surgical plan as shown in FIG. 12C.

In some embodiments, the patient-specific benchmark parameter may be a patient-specific dimension of at least one gap between first and second bone members (e.g., tibia and femur, for example).

Figure 13:
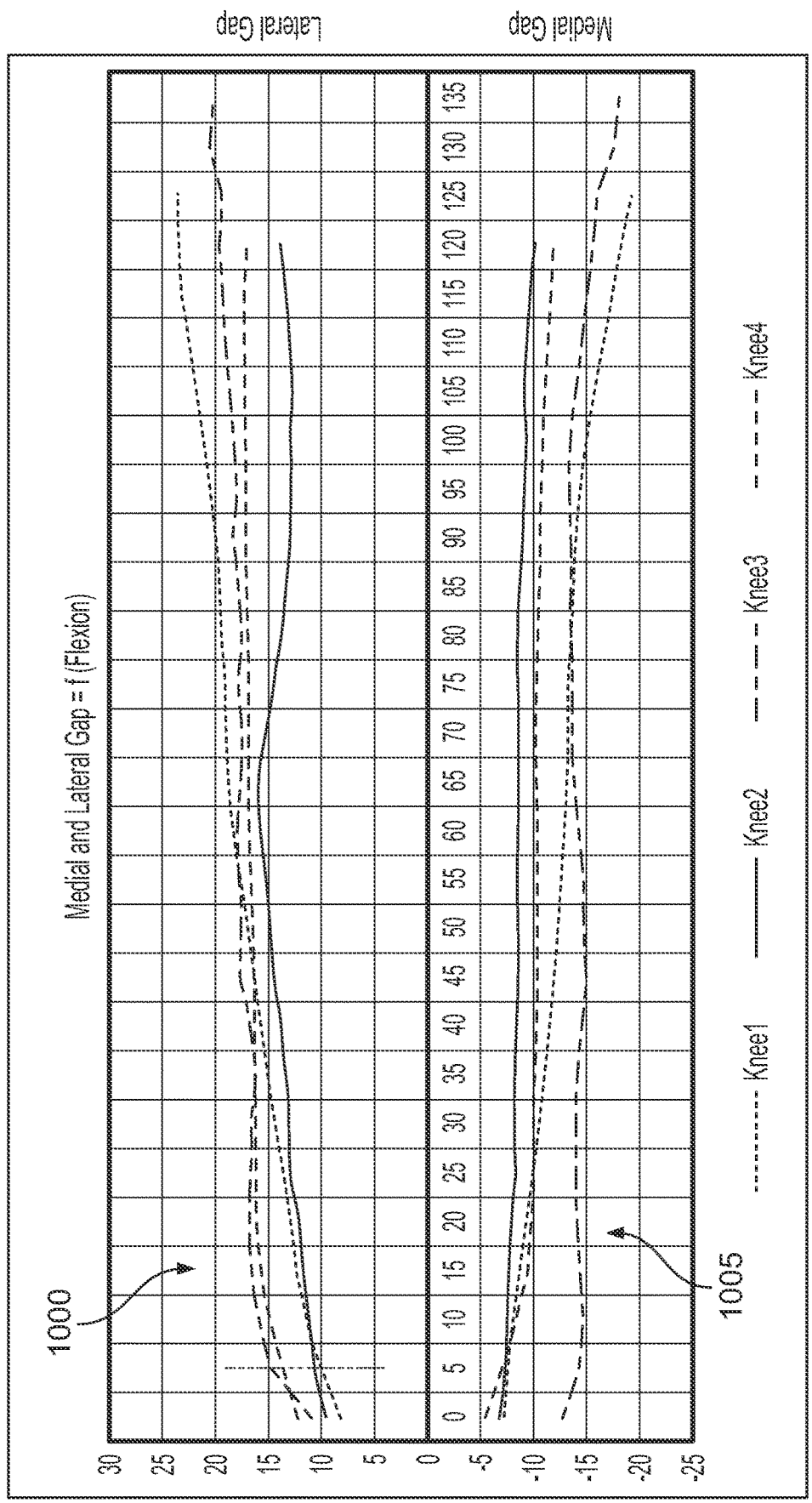
FIG. 13 are graphs illustrating an embodiment for computing a patient-specific benchmark value from patient-specific data in accordance with one or more embodiments of the present disclosure.

FIG. 13 are graphs 1000 and 1005 illustrating an embodiment for computing a patient-specific benchmark value from patient-specific data in accordance with one or more embodiments of the present disclosure. In this embodiment, the patient-specific benchmark parameter may be the flexion angle and the patient-specific benchmark value may be the personalized flexion angle X taken from the lateral and/or medial gap versus flexion angle data (e.g., the patient-specific data) from four cadaveric knees. The first graph 1000 shows a lateral gap in millimeters of a knee joint versus flexion angle in degrees for the four cadaveric knees. The second graph 1005 shows a medial gap in millimeters of a knee joint versus flexion angle in degrees for the four cadaveric knees.

In some embodiments, two coefficients may be computed from the data of graphs 1000 and 1005 using the two equations as follows:

$$CMed = \Delta MedialGap/\Delta Flexion \quad (1)$$

$$CLat = \Delta LateralGap/\Delta Flexion. \quad (2)$$

Figure 14B:
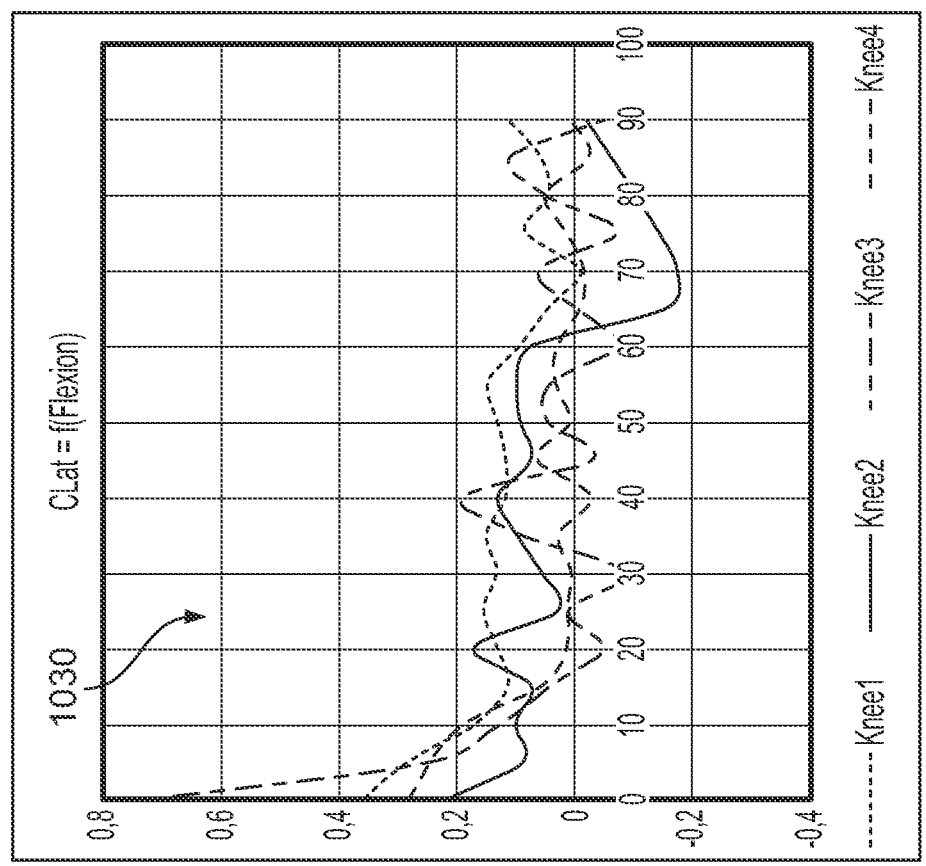
FIGS. 14A and 14B are graphs of the medial and lateral gaps versus flexion angle in accordance with one or more embodiments of the present disclosure.
Figure 14A:
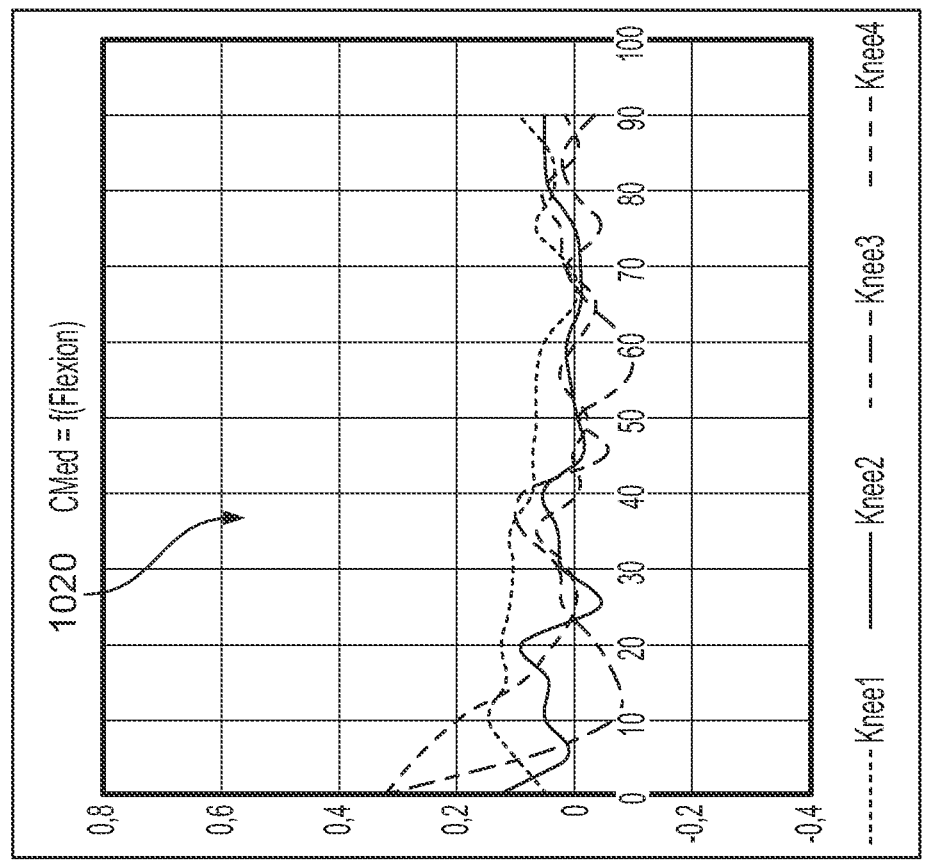

FIGS. 14A and 14B are graphs 1020 and 1030 of the medial and lateral gaps versus flexion angle in accordance with one or more embodiments of the present disclosure. Using these two graphs the personalized flexion angle may be computed by the processor 70 using a personalized flexion angle algorithm as follows: Personalized flexion angle X is defined as, the minimum angle where: (1) the leading coefficient hits a local minimum. Tangency is at a local minimum, the curve stays "below" the tangent, or (2) the leading coefficient pass below a "clinical relevant threshold" (T), where ligament no longer stretches when Flexion increases. If T=0, the ligament retracts when Flexion increases or, for this example, T may be set at 0.05 mm/deg, such that for the ligament to stretch 1 mm more, the patient's leg should be further flexed by 20° more.

Figure 15A:
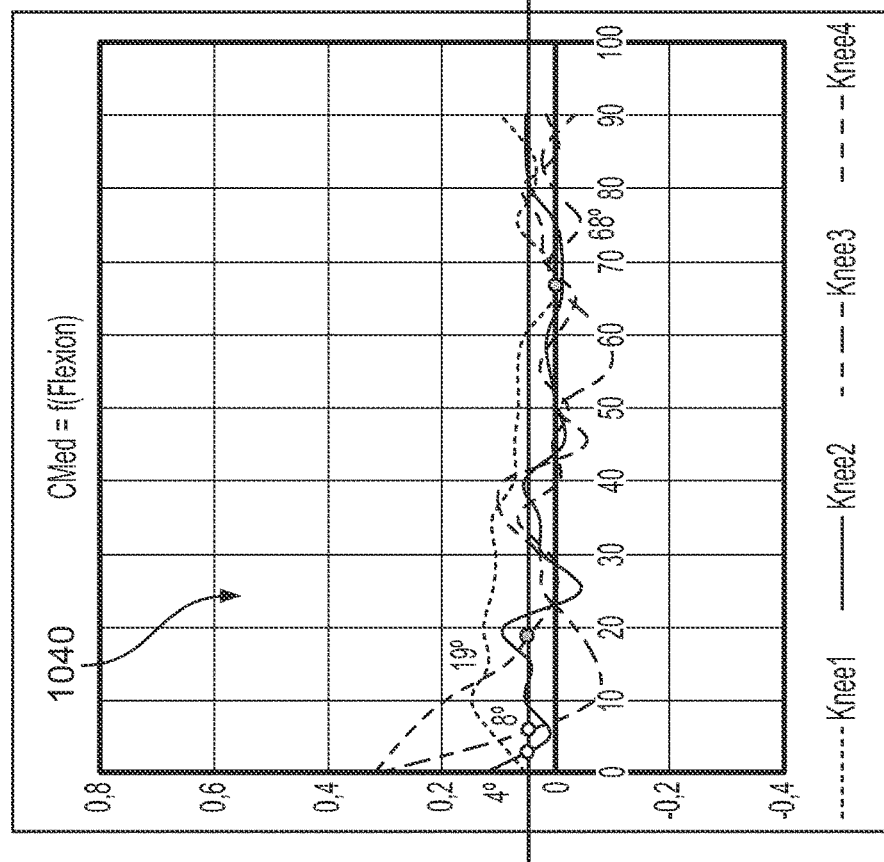
FIGS. 15A and 15B are graphs of the medial and lateral gaps versus flexion angle with minimum angles identified in accordance with one or more embodiments of the present disclosure.
Figure 15B:
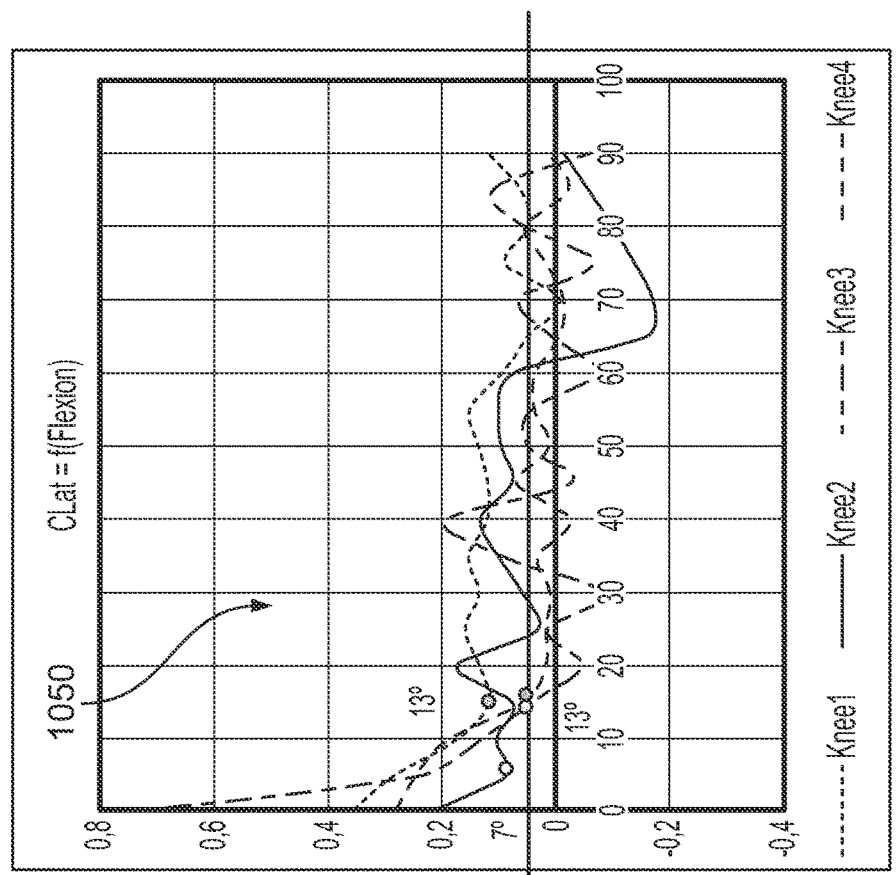

FIGS. 15A and 15B are graphs 1040 and 1050 of the medial and lateral gaps versus flexion angle with minimum angles identified in accordance with one or more embodiments of the present disclosure. The processor 70 may compute the personalized flexion angle as the minimum angle for each gap where previous conditions may be met in evaluating the minimum flexion angle for both the medial and lateral analysis. For example, the personalized flexion angle may be obtained from the curves as follows: For knee 1, the minimum angle is 13° from the CLat curve. For knee 2, the minimum angle is 4° from the CMed curve. For knee 3, the minimum angle is 8° from the CMed curve. For knee 4, the minimum angle is 13° from the CLat curve.

Figure 16:
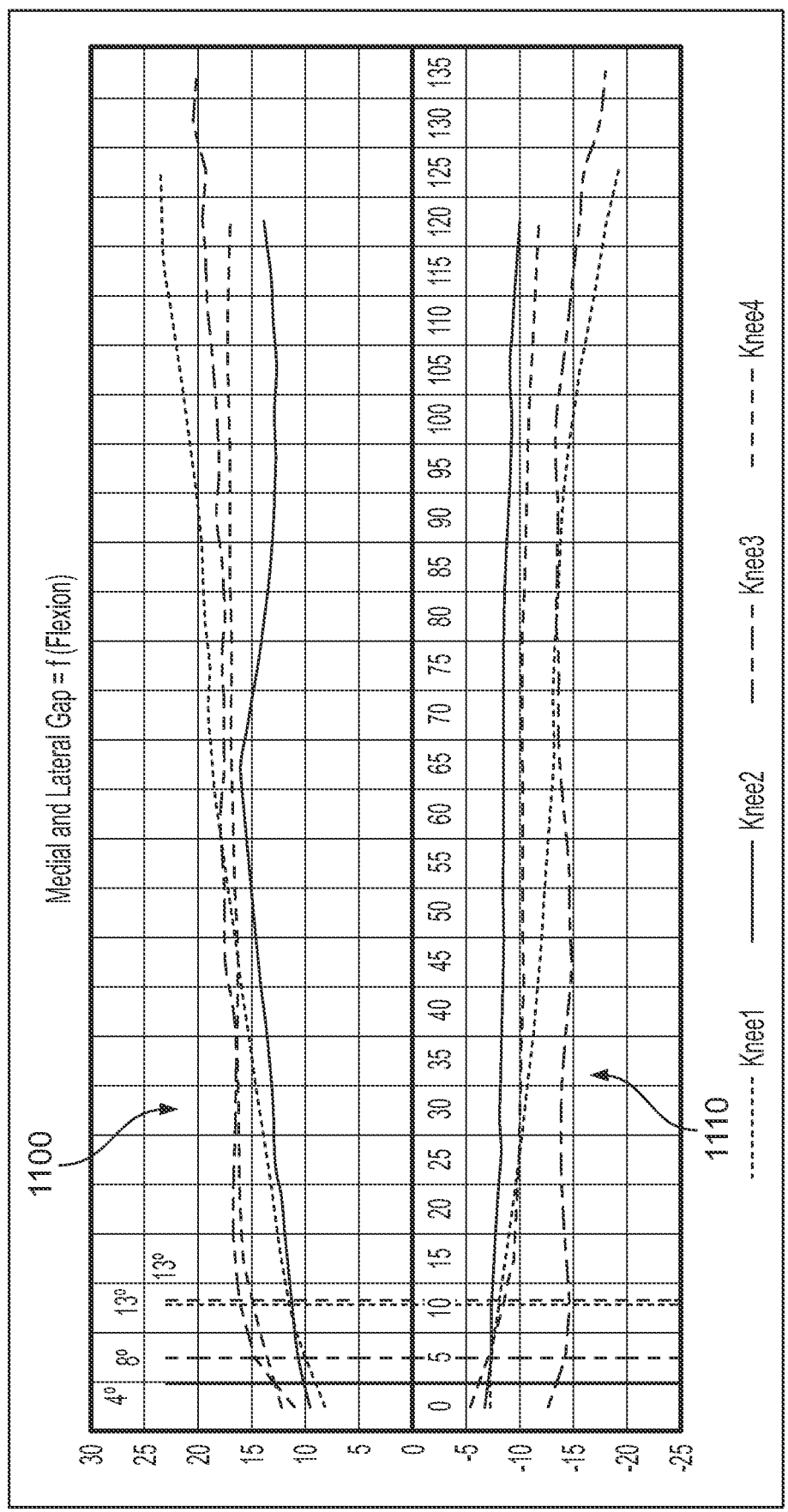
FIG. 16 are graphs showing the patient-specific benchmark values from patient-specific data in accordance with one or more embodiments of the present disclosure.

FIG. 16 are graphs 1100 and 1110 showing the patient-specific benchmark values from patient-specific data in accordance with one or more embodiments of the present disclosure. The personalized flexion angles for the four cadaveric knees are shown on the graph 1100 for the lateral gap and the graph 1110 for the medial gap (see FIG. 13).

Figure 17:
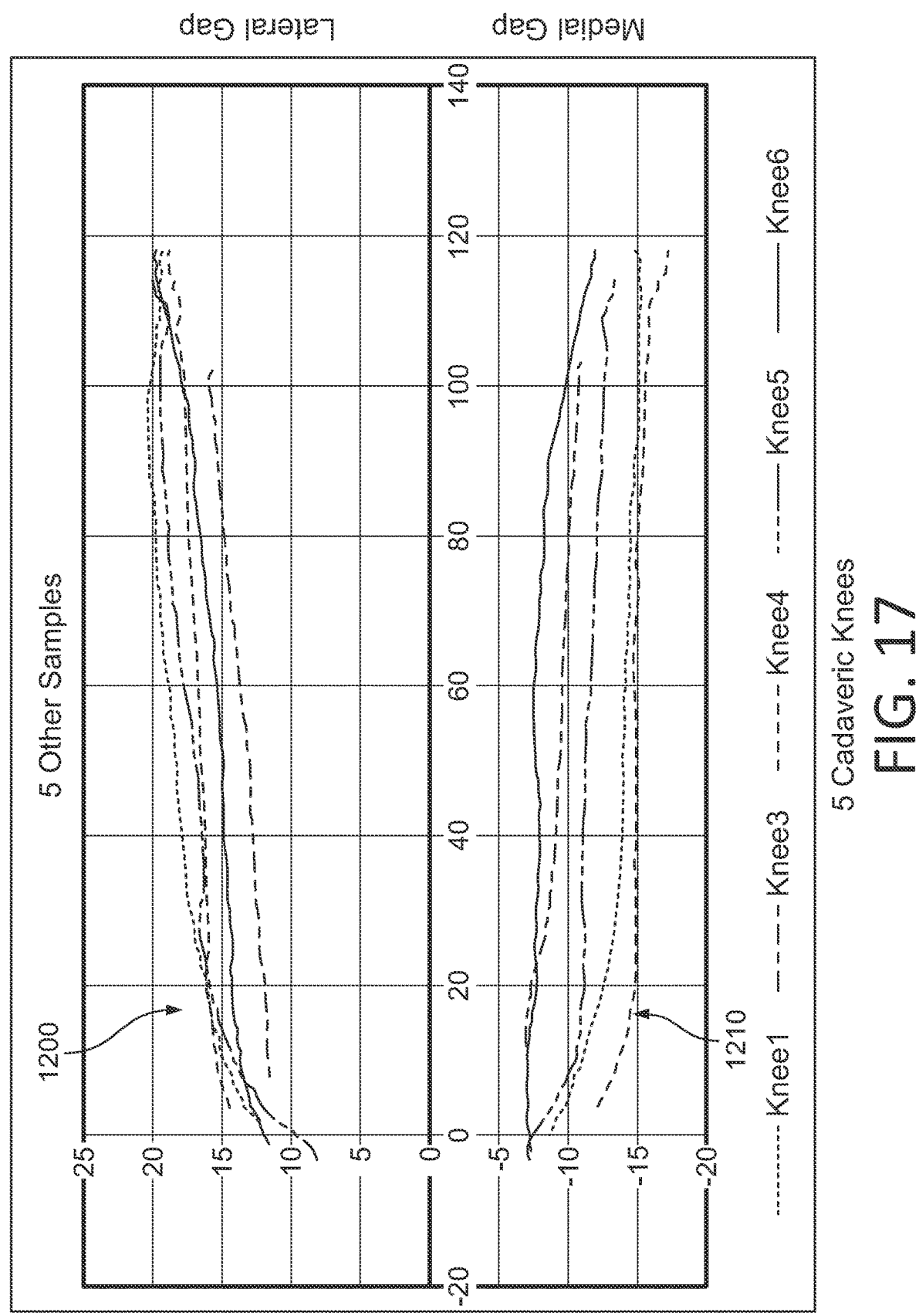
FIG. 17 are graphs illustrating a second embodiment for computing a patient-specific benchmark value from patient-specific data in accordance with one or more embodiments of the present disclosure.

FIG. 17 are graphs 1200 and 1210 illustrating a second embodiment for computing a patient-specific benchmark value from patient-specific data in accordance with one or more embodiments of the present disclosure. 5 cadaveric knees may be considered: knee 1, knee 3, knee 4, knee 5, and knee 6.

Figure 18A:
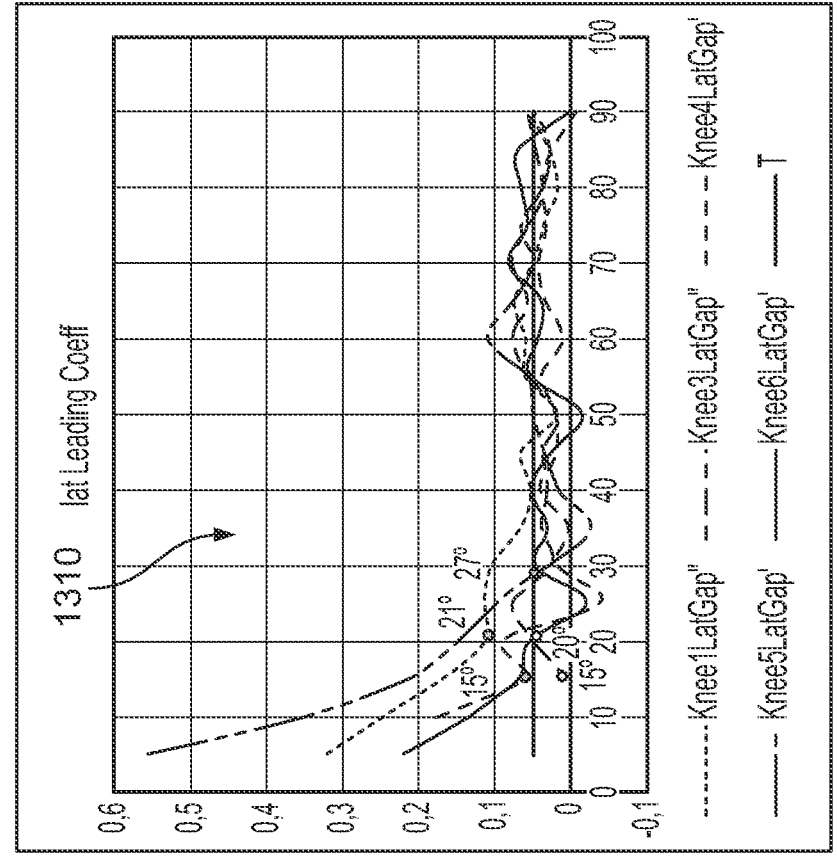
FIGS. 18A and 18B are graphs of the medial and lateral gaps versus flexion angle with minimum angles identified in accordance with one or more embodiments of the present disclosure.
Figure 18B:
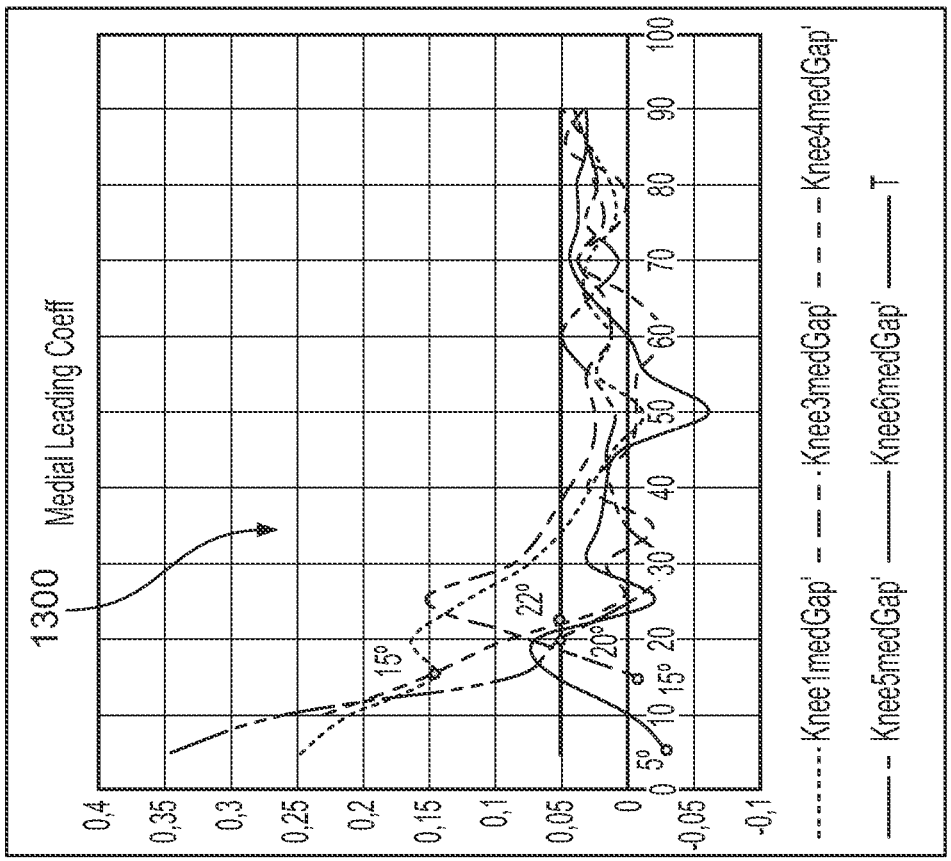

FIGS. 18A and 18B are graphs 1300 and 1310 of the medial and lateral gaps versus flexion angle with minimum angles identified in accordance with one or more embodiments of the present disclosure. Here for the second embodiment, the personalized flexion angle algorithm as similarly shown in FIGS. 14A and 14B may be used to compute the personalized flexion angle: 15° for knees 1, 3, and 4, 20° for knee 5, and 5° for knee 6.

Figure 19:
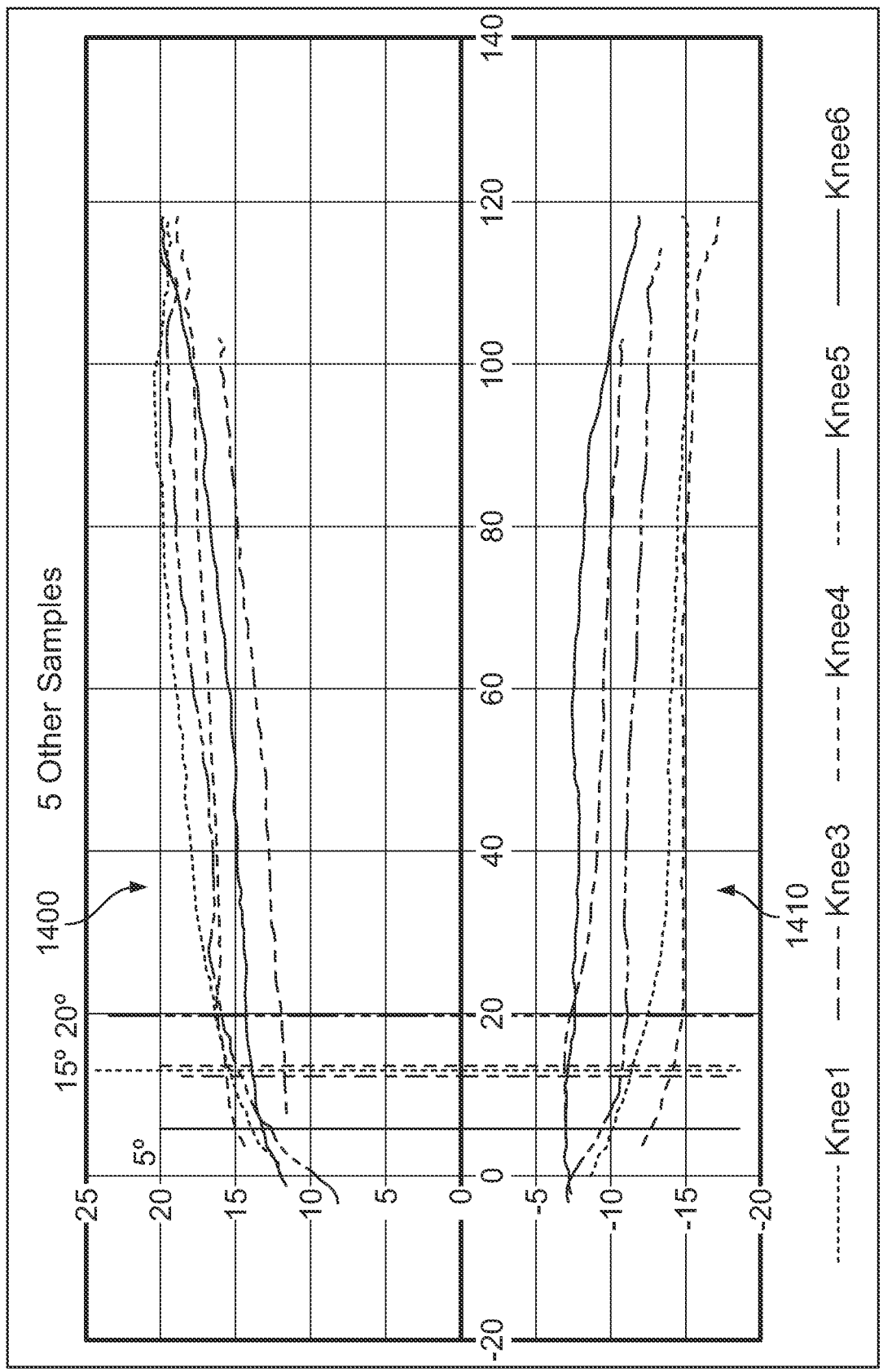
FIG. 19 are graphs showing the patient-specific benchmark values from patient-specific data in accordance with one or more embodiments of the present disclosure.

FIG. 19 are graphs 1400 and 1410 showing the patient-specific benchmark values from patient-specific data in accordance with one or more embodiments of the present disclosure. The personalized flexion angles computed by the processor 70 using the personalized flexion angle algorithm for the five cadaveric knees are shown on the graph 1200 for the lateral gap and the graph 1210 for the medial gap (see FIG. 17).

In some embodiments, processor 70 may use other algorithms to compute the patient-specific benchmark values (e.g., the personalized flexion angle) from the patient-specific data (e.g., the gap versus flexion angle data). The other algorithms may include: (1) an analysis of the second derivative (sign inversion, local minimum, (2) models using a preliminary implant planning and evolution of associated gaps, (3) a model using a combination of medial and lateral gap rather than isolated definitions of medial and lateral gap leading coefficient and/or the surgical plan generator model 75 and/or (5) the machine learning model (MLM) 77 which uses correlations with patient outcomes.

There are several known surgical workflows for total knee arthroscopy (TKA) preparation such as for example, the measured resection technique, the modified gap balancing technique, and the full gap balancing technique. Regardless of the selected workflow, the surgeon may select the cut parameters in terms of alignment based on pre-established recommendations or personal preferences, but the surgeon's selection is rarely based on patient-specific considerations. The surgeon may address the ligament laxities based on qualitative considerations and often after the full preparation of both the tibia and the femur. The lack of combination between the management of the alignment and laxity considerations as well as the lack of quantitative patient specific information may account for the large percentage of unsatisfied TKA patients.

Thus, in the embodiments disclosed herein, the software-based CAS system implemented by the controller 65 and the algorithms executed thereon as shown in FIG. 2 provide a technical solution to these technical problems. For example, these advanced technologies (e.g., Newton) may allow for the acquisition of the knee laxities under a distraction force throughout the full arc of motion.

In some embodiments, the patient-specific laxity curves may be combined with the surgeon's inputs via the display 60 and keyboard 62 in terms of desired cut parameters, size, and alignment to define a personalized surgical plan based on these inputs. In other embodiments, the patient-specific laxity curves may be combined with the surgeon's inputs in terms of desired cut parameters, size, and alignment to define a personalized surgical plan based on these inputs to match the expected functional parameters.

Figures 20A, 20B:
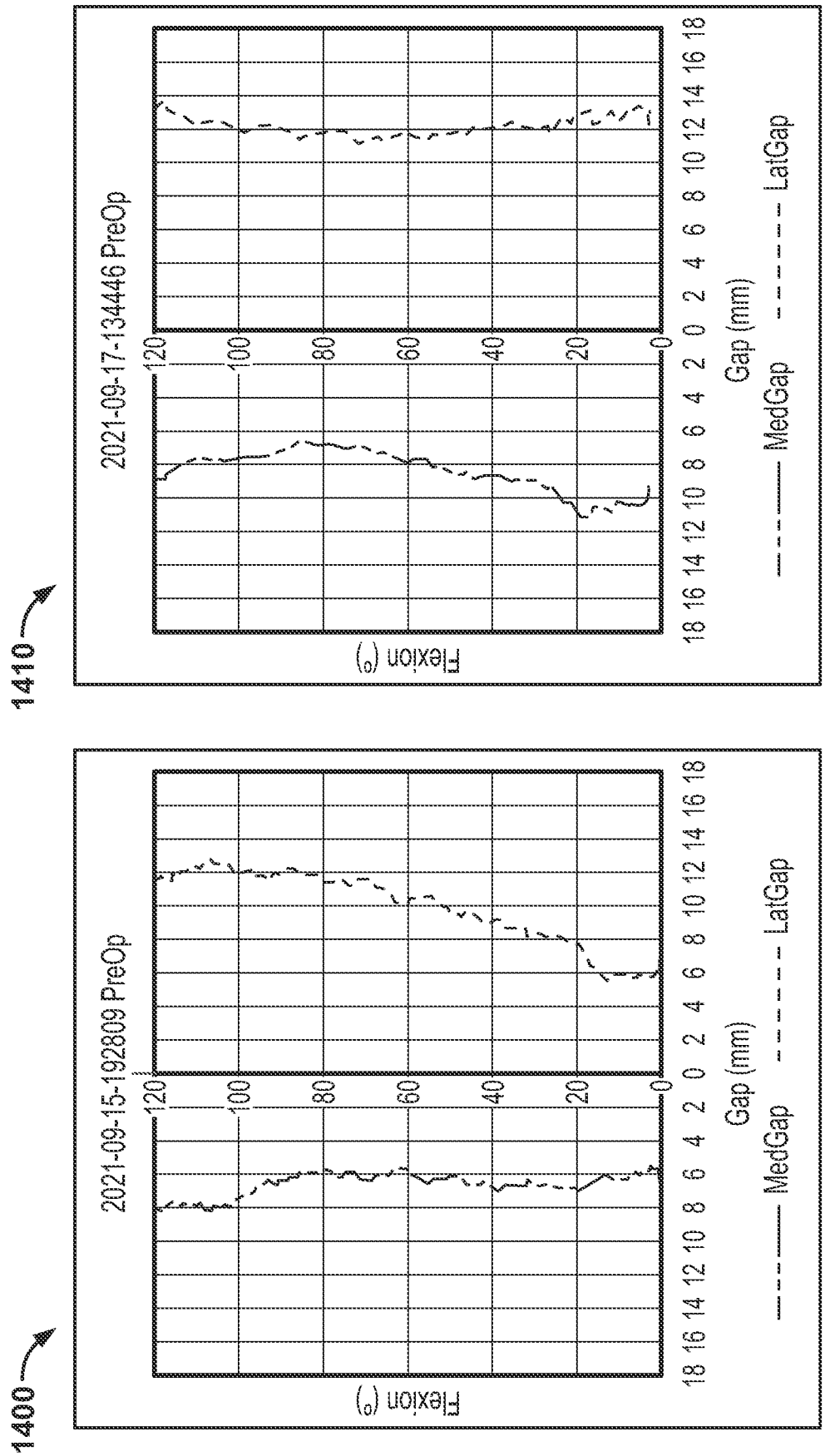
FIGS. 20A and 20B are graphs of two exemplary laxity curves in accordance with one or more embodiments of the present disclosure.

FIGS. 20A and 20B are graphs of two exemplary laxity curves 1400 and 1410 in accordance with one or more embodiments of the present disclosure. The exemplary laxity curves are between the native femur and the proximal tibial cut when the native femur is distracted from the proximal tibial cut through the action of a tensor (e.g., the ligament balancing device 800) of FIG. 10. The X-axis (joint gap in mm) represents the distance between the closest point of the medial condyle (MedGap) to the proximal tibial cut and the distance between the closest point of the lateral condyle (LatGap) to the proximal tibial cut. The Y-axis represents the flexion angle between the tibial mechanical axis and the femoral mechanical axis.

Figures 21A, 21B, 21C:
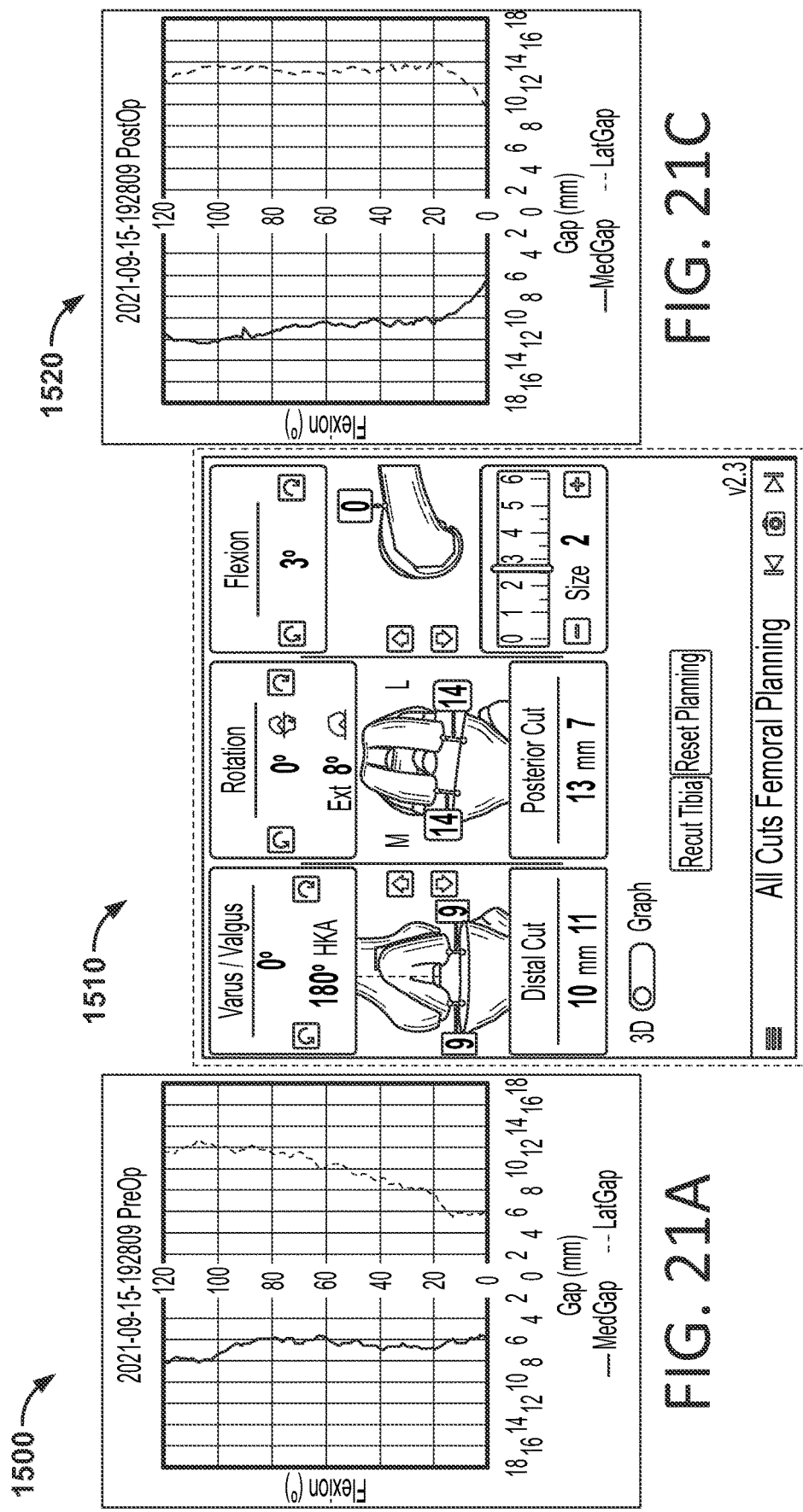
FIG. 21A is a laxity curve of a pre-femoral cut acquisition in accordance with one or more embodiments of the present disclosure.
FIG. 21B illustrates an exemplary snapshot of a graphical user interface output showing a personalized surgical plan in accordance with one or more embodiments of the present disclosure.
FIG. 21C is shows a final laxity curve in accordance with one or more embodiments of the present disclosure.

FIG. 21A is a laxity curve 1500 of a pre-femoral cut acquisition (e.g., step 350 FIG. 6) in accordance with one or more embodiments of the present disclosure. The laxity curve 1500 may indicate a large joint balance discrepancy in flexion (i.e., ~6 mm medial gap at 90° vs. ~12 mm lateral gap at 90°).

FIG. 21B illustrates an exemplary snapshot 1510 of a graphical user interface output showing a personalized surgical plan in accordance with one or more embodiments of the present disclosure. The exemplary snapshot 1510 may be displayed on the graphical user interface 61 of the display 60. The surgical plan may define the following parameters of a Neutral HKA (i.e., HKA=180°), a rectangular gap in extension (e.g., the same gap between medial and lateral compartments), a rectangular gap in flexion (e.g., the same gap between medial and lateral compartments), a recommendation of externalizing the femur by 8° (instead of usual 3°) in order to close the lateral gap in flexion, and 5 mm added laxity in flexion compared to extension (e.g., the surgeon's personal preference).

FIG. 21C is shows a final laxity curve 1520 in accordance with one or more embodiments of the present disclosure. The final laxity curve 1520 may be displayed to the surgeon 15 on GUI 61. The final laxity curves 1520 may indicate symmetrical laxities between medial and lateral compartments throughout the full arc of motion with approximately a 9 mm gap in personalized extension (e.g., an angle between 10 and 15° of flexion) and approximately a 14 mm gap at 90° of flexion.

With regard to the definition of a tibial insert as an input to the surgical plan, once the bone cuts are performed, the surgeon 15 may place trial components onto the prepared bones and may perform manual trial reductions by sequentially placing monoblock trial tibial inserts of different thicknesses (and eventually design types). Based on this evaluation, the surgeon 15 may select the characteristics of the final tibial insert to be implanted. In addition to being time consuming, this evaluation is also qualitative by nature.

Thus, in some embodiments, instead of using monoblock trial tibial inserts, a distractor device such as for example, the ligament balancing device 800 of FIG. 10 may be used to apply a quasi-constant distraction force. The distractor device may be placed between the prepared proximal tibial cut and the trial femoral component, and a range of motion may be subsequently induced to capture the spatial poses of the knee joint 20 with the distractor device.

Figures 22A, 22B:
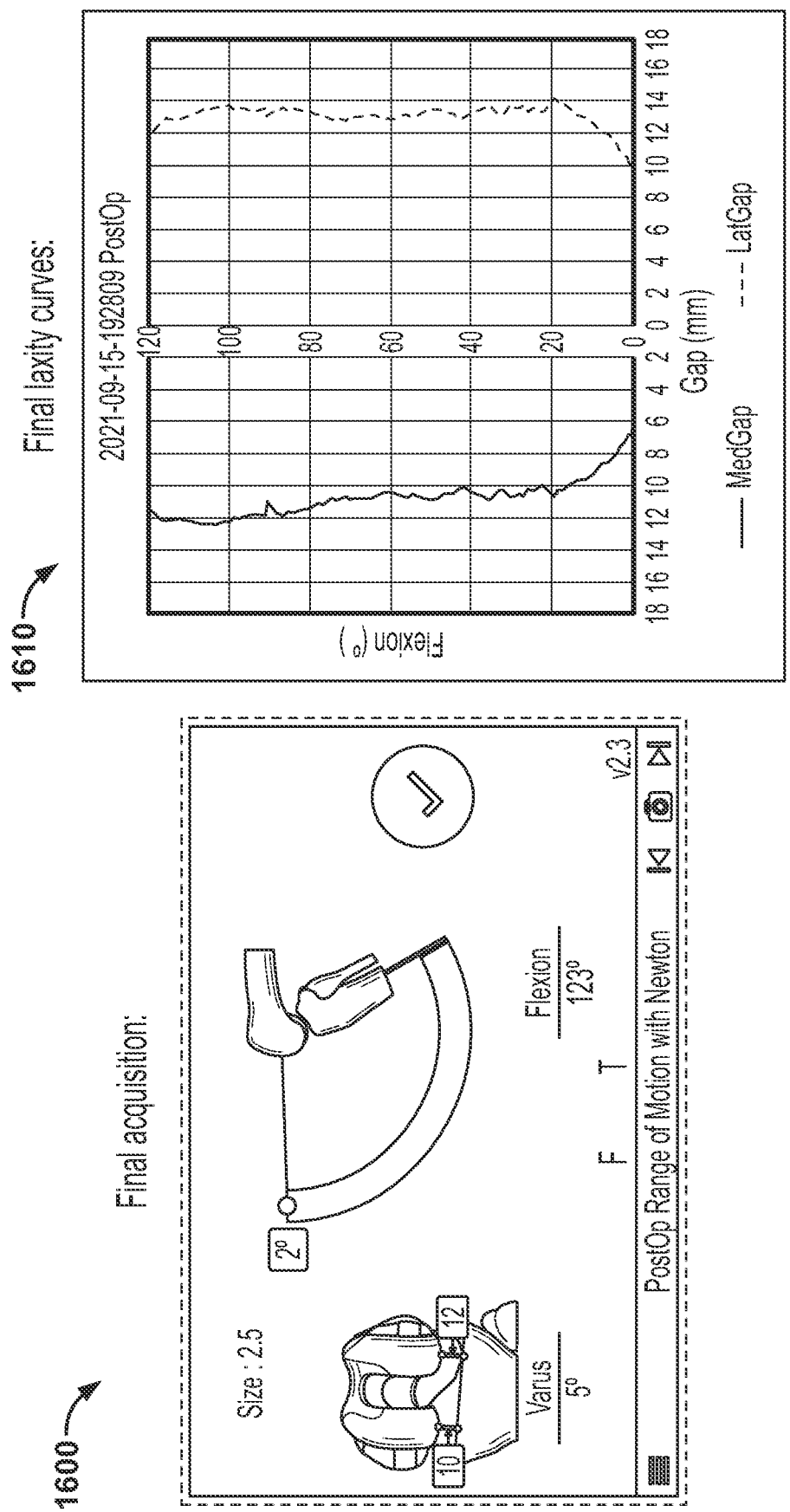
FIG. 22A shows an exemplary graphic user snapshot of a final acquisition in accordance with one or more embodiments of the present disclosure.
FIG. 22B shows a final laxity curve in accordance with one or more embodiments of the present disclosure.

FIG. 22A shows an exemplary graphic user snapshot 1600 of a final acquisition in accordance with one or more embodiments of the present disclosure. The exemplary graphic user snapshot 1600 of a final acquisition may be displayed on the GUI 61.

FIG. 22B shows a final laxity curve 1610 in accordance with one or more embodiments of the present disclosure. The final laxity curve 1610 may be displayed on the graphic user interface 61.

Figure 22C:
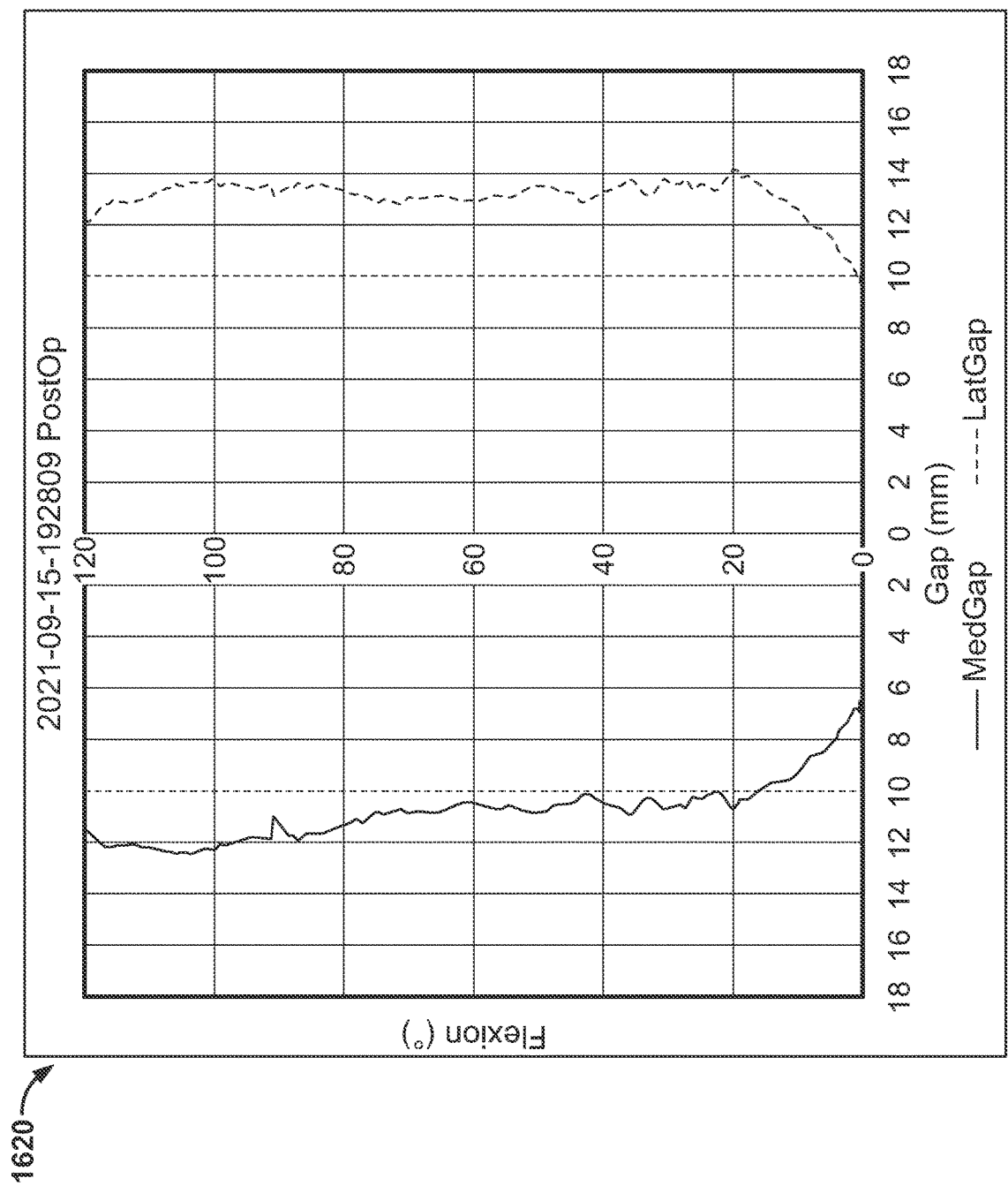
FIG. 22C shows a final laxity curve with tibial insert recommendations in accordance with one or more embodiments of the present disclosure.

FIG. 22C shows a final laxity curve 1620 with tibial insert recommendations in accordance with one or more embodiments of the present disclosure. The final laxity curve 1620 with tibial insert recommendations may be displayed on the graphic user interface 61. The tibial insert thickness recommendations may be based on a range of motion (i.e., avoid flexion contracture) and/or based on joint laxity preference defined by the surgeon 15.

Figure 23B:
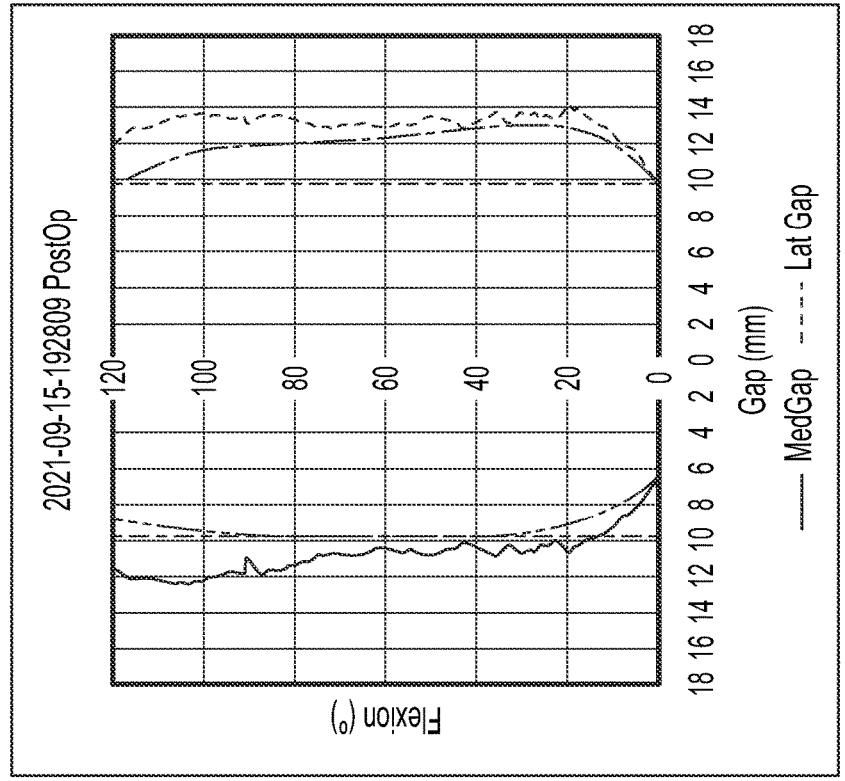
FIGS. 23A and 23B shows final laxity curves respectively before and after compensation in accordance with one or more embodiments of the present disclosure.
Figure 23A:
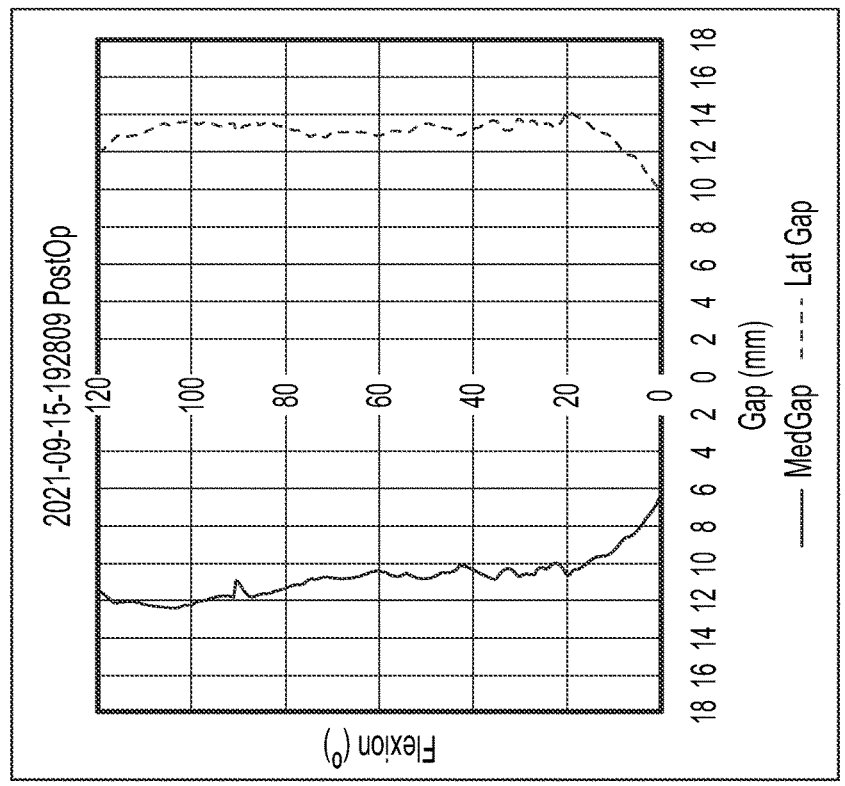

FIGS. 23A and 23B shows final laxity curves 1700 and 1710 respectively before and after compensation in accordance with one or more embodiments of the present disclosure. The final laxity curves may be compensated by the assumed kinematic of the knee joint (e.g., rollback of the femoral component/tibial component in flexion leading to the femoral component to ride against the posterior lip of the insert).

With regard to alignment phenotype as input to the surgical plan, the foundation of a successful knee replacement is the restoration of neutral knee alignment. Medical data has shown that based on 4,884 lower limb CT-scans of patients scheduled for knee replacement, only 0.1% of patients had both a mechanical proximal tibial and distal femoral angles at neutral. Precut kinematics acquisition may provide patient-specific information regarding the overall limb alignment.

Figure 24:
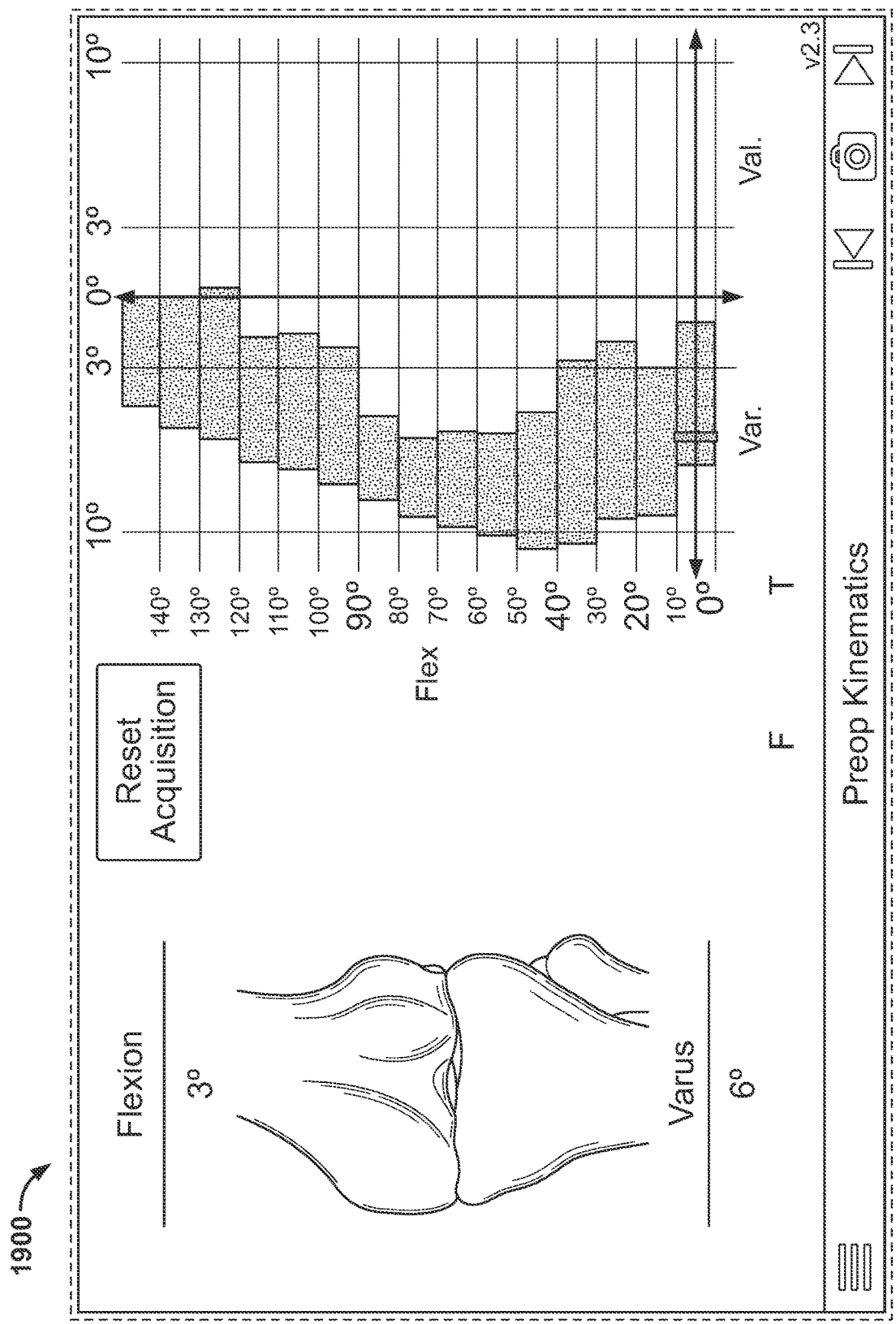
FIG. 24 shows an exemplary preoperative kinematics snapshot of a graphic user interface in accordance with one or more embodiments of the present disclosure.
Figures 25A, 25B, 25C:
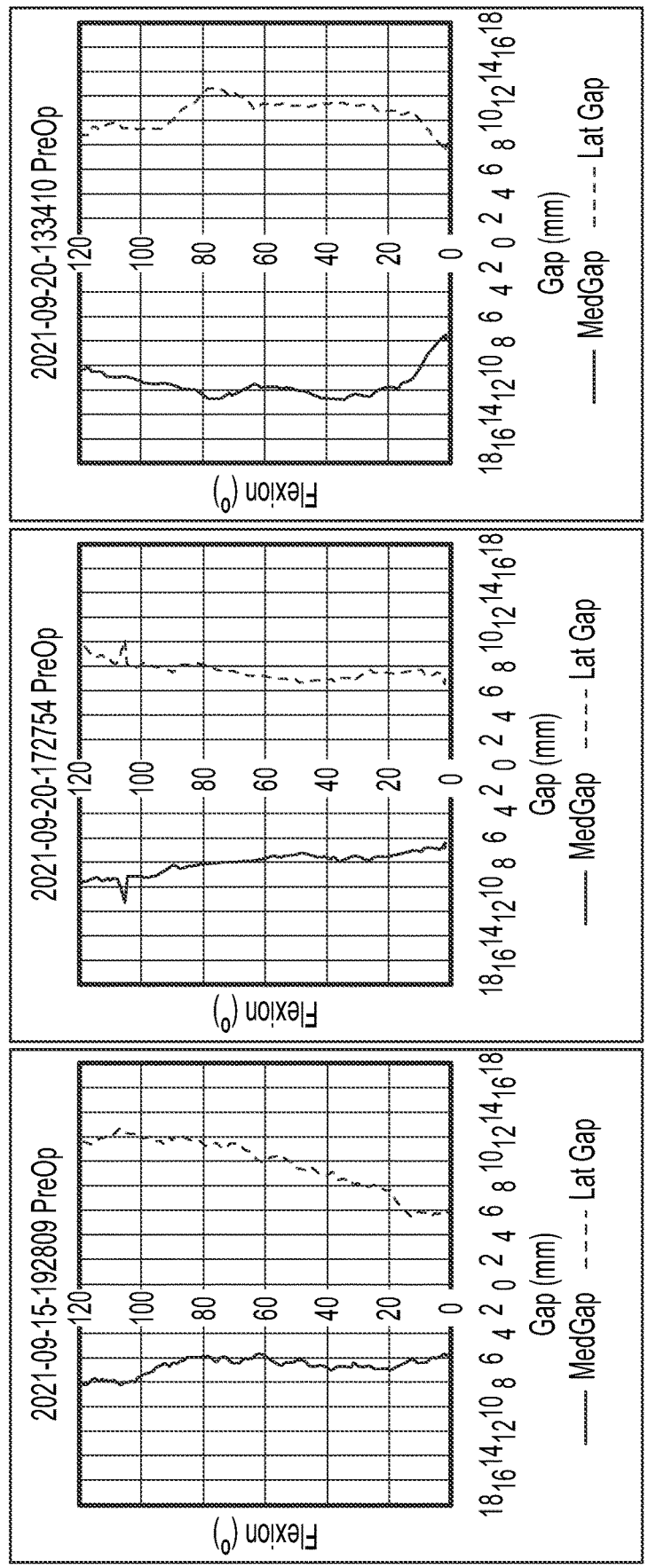

FIG. 24 shows an exemplary pre-operative kinematics snapshot 1900 of the graphic user interface 61 in accordance with one or more embodiments of the present disclosure. Precut kinematics acquisition may provide patient-specific information regarding the overall limb alignment and therefore the alignment target. The exemplary pre-operative kinematics snapshot 1900 as shown in FIG. 24 illustrates that the knee joint of the patient prior to surgery may exhibit varus alignment over the range of flexion angles.

FIGS. 25A-25E show pre-operative laxity curves in accordance with one or more embodiments of the present disclosure. With regard to laxity phenotype, pre-femoral cut laxity may define the laxity curves for the medial and lateral compartments throughout the arc of flexion. The curves 2000, 2010, 2020, 2030, and 2040 may represent the patient-specific signature of the soft-tissue envelope. While the current standard is to obtain symmetrical gaps (i.e., same gap between medial and lateral compartments) and constant gaps (i.e., same gap throughout the arc of motion), these curves may fluctuate substantially from patient to patient, such that optimal laxity may be patient-specific. Thus, processing of these curves may be used to define the optimal post-operative laxity (i.e., functional parameter(s)) to achieve, thus affecting, without limitations, the definition of the surgical plan. The possibility of compensating the pre-femoral cut (but post-tibial cut) but reversing the tibial cut (i.e., subtract the laxity by the thickness of the tibial cut at each discrete angle of flexion) to obtain a virtual native laxity curve under quasi-constant distraction force before any bone cuts are made.

With regard to three-dimensional soft tissue management, soft-tissue balance may be predicted for any joint using a single dimension defined by the gap between the two boney entities of the given joint. In considering a knee joint, the gap may relate, for example, to the distance between the proximal tibial cut and the most distal point of one femoral condyle, measured on an axis perpendicular to the proximal tibial cut preferably under constant distraction force. Such measurement may be performed by femoral condyle at several angles of flexion, thus providing a cartography of the gaps. The cartography of the gaps may be leveraged to plan the position and orientation of the implants for obtaining a properly aligned and balanced joint. During the planning phase, the management of the soft-tissue may be treated from a sole unidimensional point of view with no consideration for the impact of the 3D volume aspect of the joint on the unidimensional measurement.

While some osteophytes may be removed before any bone cuts, some osteophytes such as posterior condylar osteophytes of the femur, for example, tend to only be accessible after at least a preliminary cut, which is not an option for a pre-cut planning approach. Planning of the components performed prior to removal of the osteophytes may lead to discrepancies in terms of soft-tissue balance.

Another limitation in soft-tissue management may be, for example, that during a TKA planning phase, if there is a need to close the flexion gap by 2 mm, then the femoral component may be flexed or a larger component may be used to increase to posterior build-up that reduces the flexion gap. However, this basic approach does not consider that the increased build-up may stretch the soft-tissue envelope if the implant-based posterior condylar offset may be higher than the native posterior condylar offset. This may impact the unidimensional measure of the planned gap.

In some embodiments, to address these limitations in soft-tissue management, three tools may be used. A volumetric indicator tool may be used to predict the impact of a volume change on the unidimensional measurement of the gap. By doing so, the volume change may be considered in the definition of the planning of the joint gap.

In some embodiments, an osteophyte indicator tool may be used to predict the impact of the osteophyte(s) on the pre-cut planning. The osteophyte indicator tool may acquire anatomical landmarks, define the location and size of the osteophyte(s) from an imaging modality, superpose the two sets of information, perform some acquisition, such as ROM, stress VV, etc, (may be conducted at any earlier step), issue a pre-cut planning based on acquisitions, and/or issue a pre-cut planning based on acquisitions and simulated compensation of the osteophyte(s).

Figure 26A:
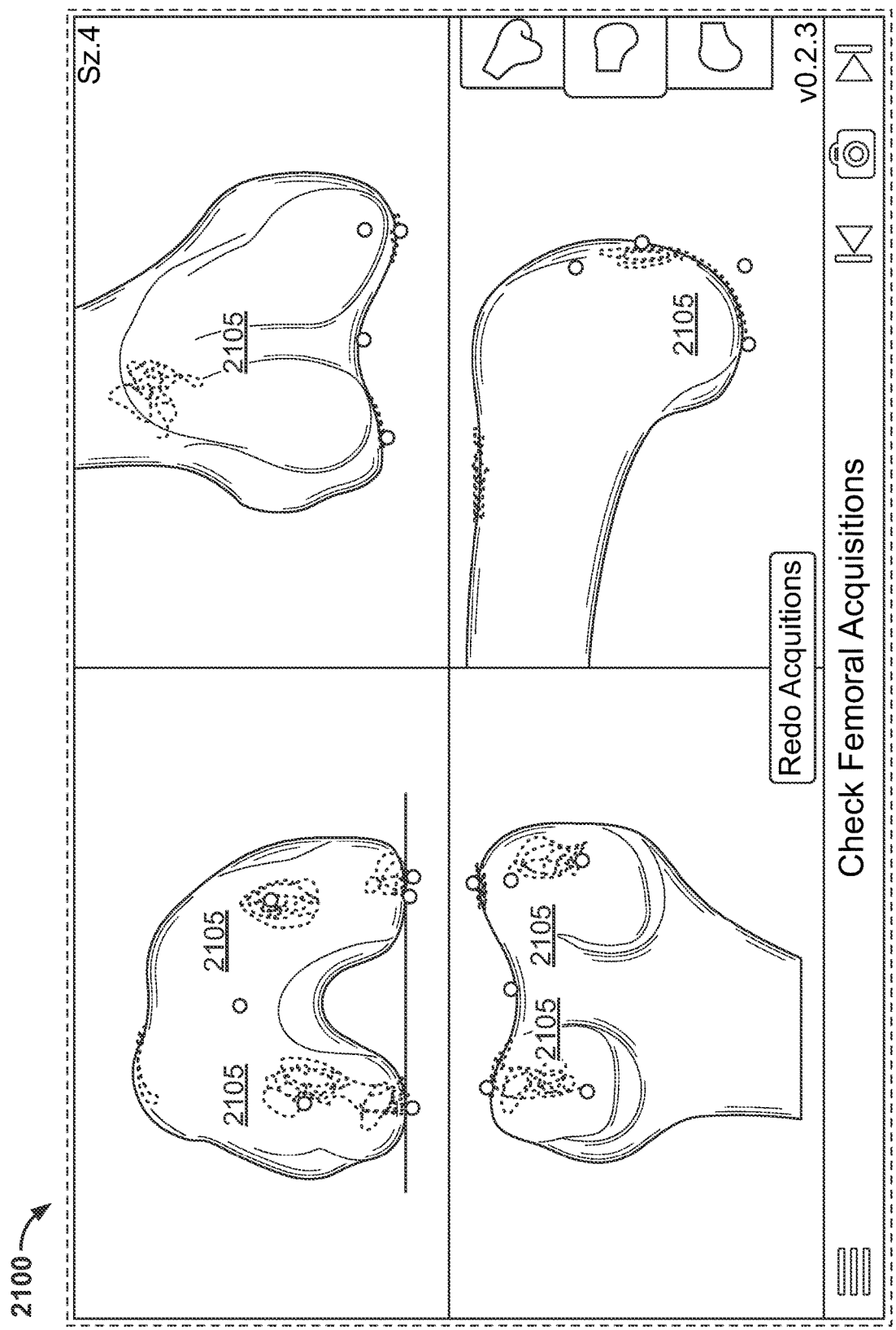
FIG. 26A shows a first exemplary snapshot of an osteophyte indicator tool for anatomical acquiring landmarks in accordance with one or more embodiments of the present disclosure.
Figure 26B:
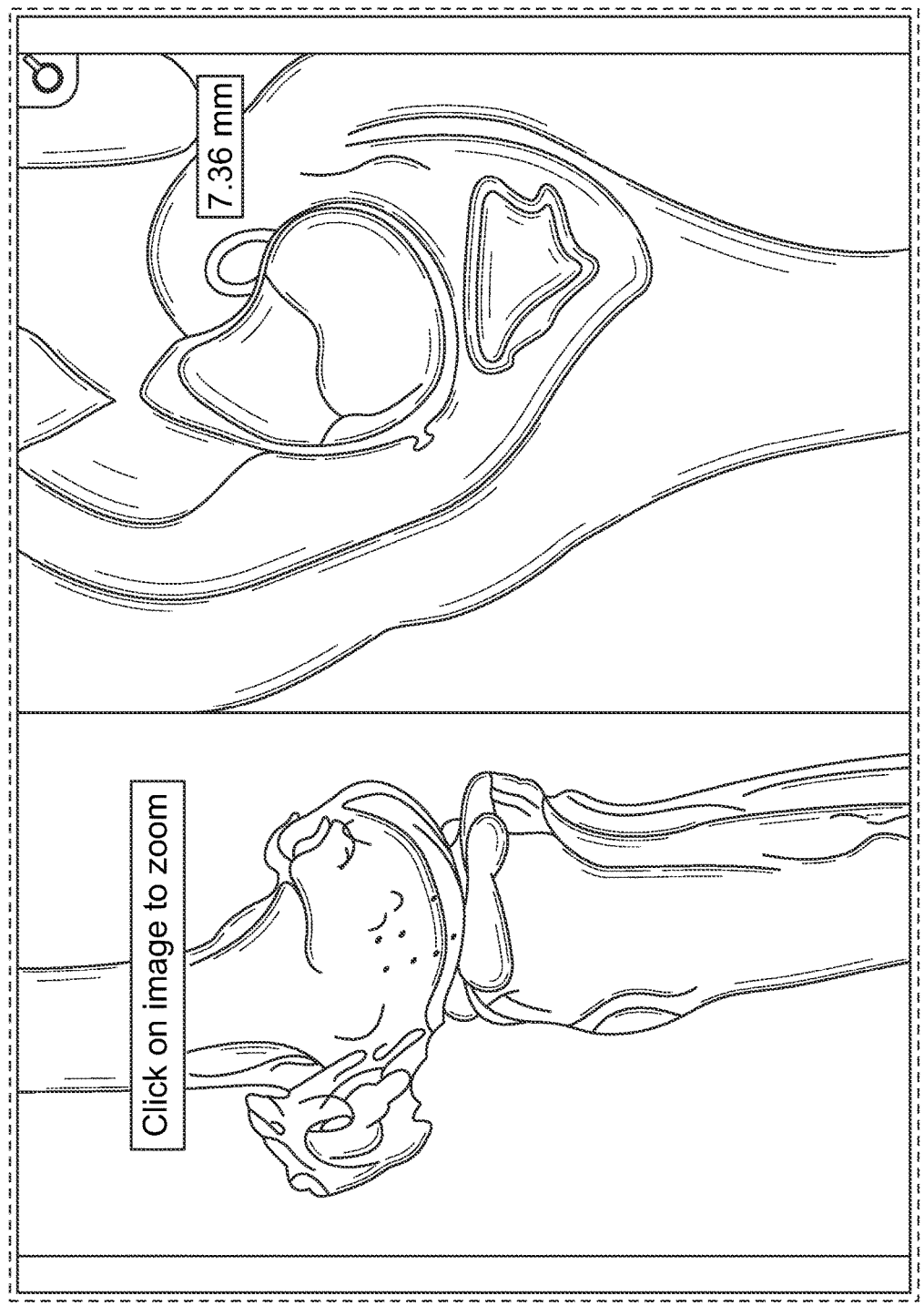
FIG. 26B shows an exemplary image for defining a location and size of osteophytes from an imaging modality in accordance with one or more embodiments of the present disclosure.
Figure 26C:
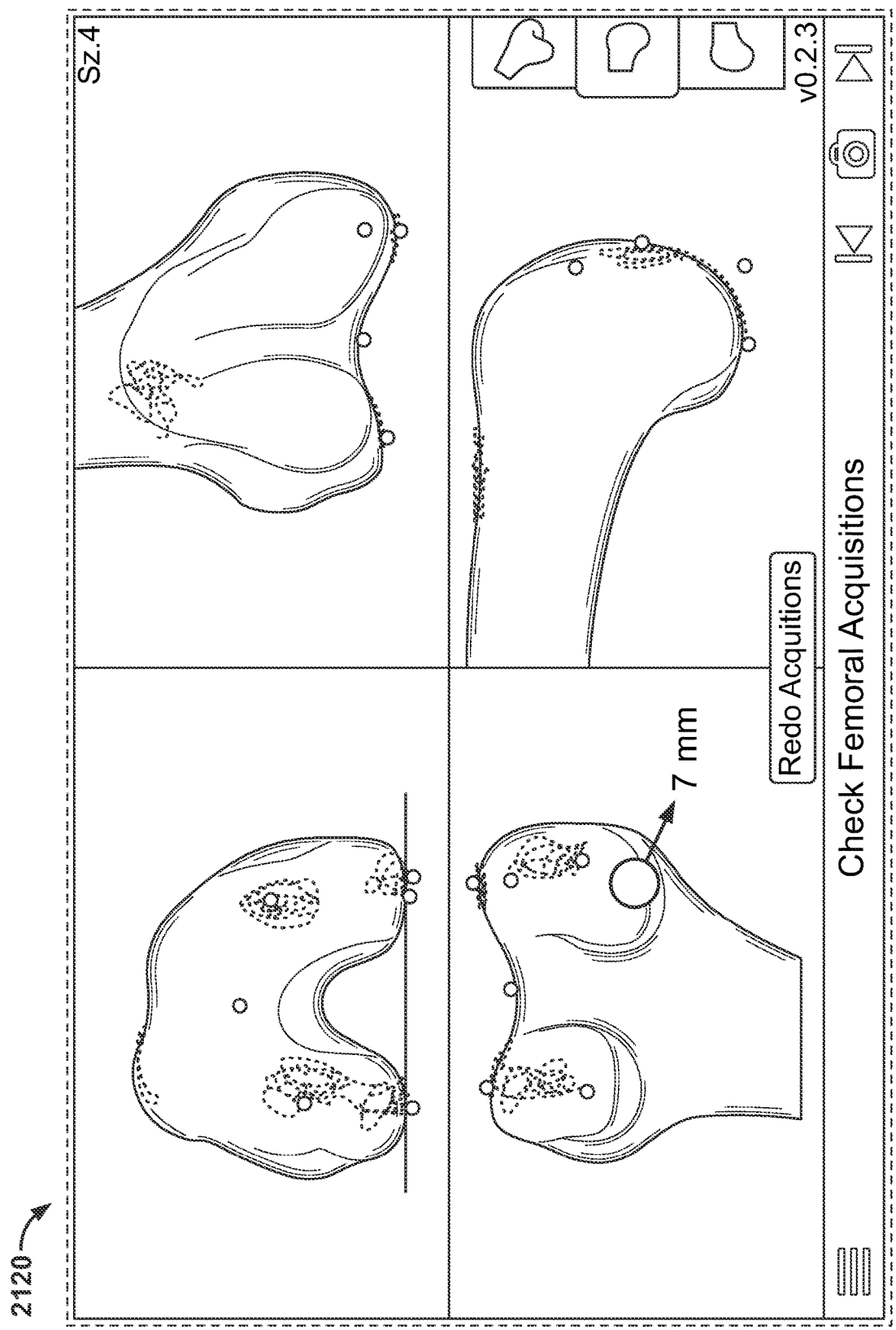
FIG. 26C shows a second exemplary snapshot of an osteophyte indicator tool for anatomical acquiring landmarks in accordance with one or more embodiments of the present disclosure.

FIG. 26A shows a first exemplary snapshot 2600 of an osteophyte indicator tool for anatomical acquiring landmarks in accordance with one or more embodiments of the present disclosure. The traces along the condyles may be the trajectories of landmarks over a range of motions. The traces may also be referred herein as trajectories. FIG. 26B shows an exemplary image 2110 for defining a location and size of osteophytes from an imaging modality in accordance with one or more embodiments of the present disclosure. FIG. 26C shows a second exemplary snapshot 2120 of an osteophyte indicator tool for anatomical acquiring landmarks in accordance with one or more embodiments of the present disclosure.

Figure 27:
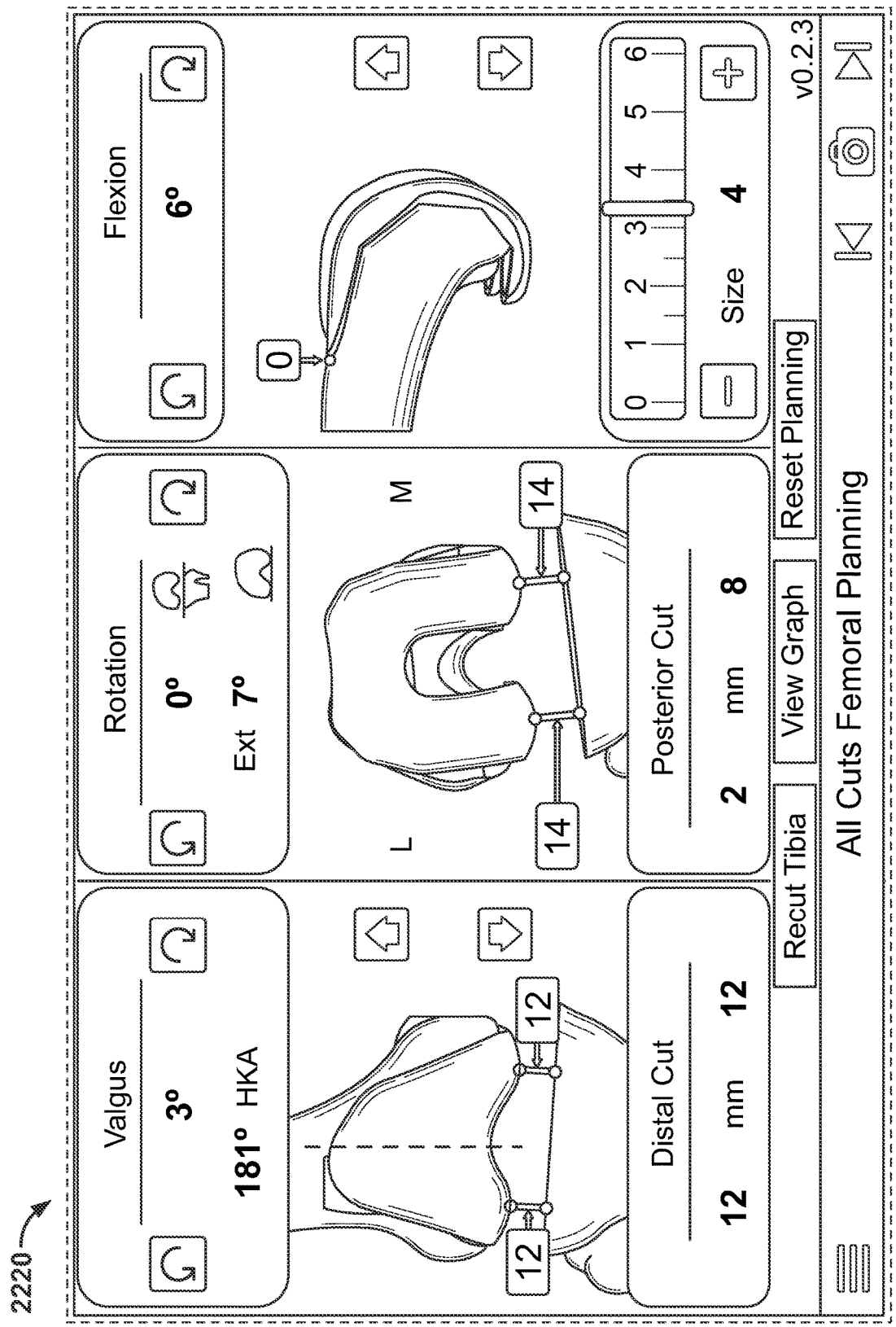
FIG. 27 is an exemplary snapshot of a graphic user interface of a soft-tissue compensation tool in accordance with one or more embodiments of the present disclosure.

FIG. 27 is an exemplary snapshot 2200 of a graphic user interface of a soft-tissue compensation tool in accordance with one or more embodiments of the present disclosure. The soft-tissue compensation tool may perform a thickness comparison between the implant and the virtual bone cut resulting from the planned position and orientation of the component. The soft-tissue compensation tool may be configured to perform planning of the component, to compare the thickness of the implant versus bone cut, and to assign a compensation on displayed gaps if thickness of the implant may be larger than the thickness of the anticipated bone cut as an attempt to consider the shortening of the ligament due to added build-up. The exemplary snapshot 2200 of FIG. 27 shows an example where the bone resection (2 mm) was substantially lower than the implant thickness (8 mm) that may lead to tightness in extension. Instead, the final insert was 9 mm and not 12 mm as planned.

Before the implementation of the embodiments disclosed in this disclosure, the standard approach to setting up a surgical plan for a total joint arthroplasty procedure involved the surgeon providing an initial manual definition of the bone cut parameters as inputs with expected functional output in terms of alignment, laxity, and size. However, specifically with regard to TKA, the embodiments of the present disclosure reverse this standard approach where the functional aspects of the knee in terms of alignment, laxity, and size may be treated as input to drive the definition of the cut parameters. Stated differently, the definition of the expected functional outcomes of the knee may be used by the CAS system as inputs, which leads to the definition of an algorithm-based surgical plan using the bone cut parameters as variables as shown in FIG. 4A.

Furthermore, with regard to the CAS systems and methods disclosed herein, the tradeoffs between the number of inputs to be considered for the surgical plan and the ease of intra-operatively setting-up the surgical plan may be addressed in that if there are a limited number of inputs, so the set-up of the surgical plan is easily manageable, then key parameters such as the soft-tissue data measured over the arc of motion, for example, may be missing. On the other hand, if the number of inputs to be considered is too large, such as the soft-tissue data measured over the arc of motion, for example, then the set-up of the surgical plan represents a substantial cognitive burden on the surgeon during surgery.

In some embodiments, the CAS systems and methods described herein may leverage (1) expected functional parameters, (2) a ranking of these functional parameters, (3) ranges of acceptable cut parameters in terms of position/ orientation, and (4) intraoperative acquisitions as inputs to feed an algorithmic based model and/or machine learning model, which may define a surgical plan as an output that may be expressed in terms of singular cut parameters (i.e., position/orientation considerations) preferably chosen inside a range of acceptable cut parameters. The functional parameters may be surgeon-based, patient-based, surgeon and patient-based, or may relate to expected outcomes as defined by a mode such as sport, comfort, range of motion, longevity, etc.

Figure 28A:
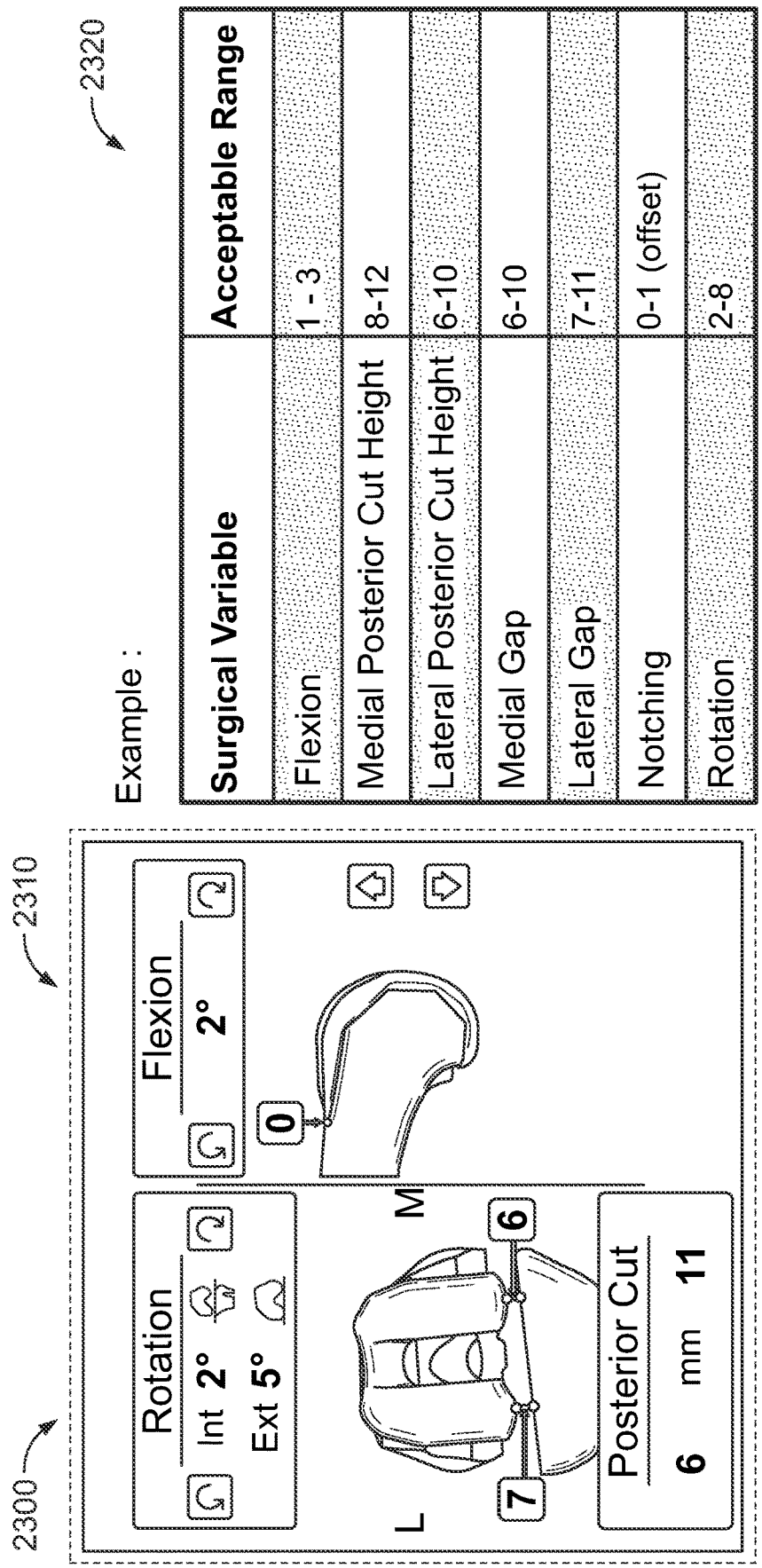
FIGS. 28A and 28B illustrate dependencies between surgical variables in accordance with one or more embodiments of the present disclosure.
Figure 28B:
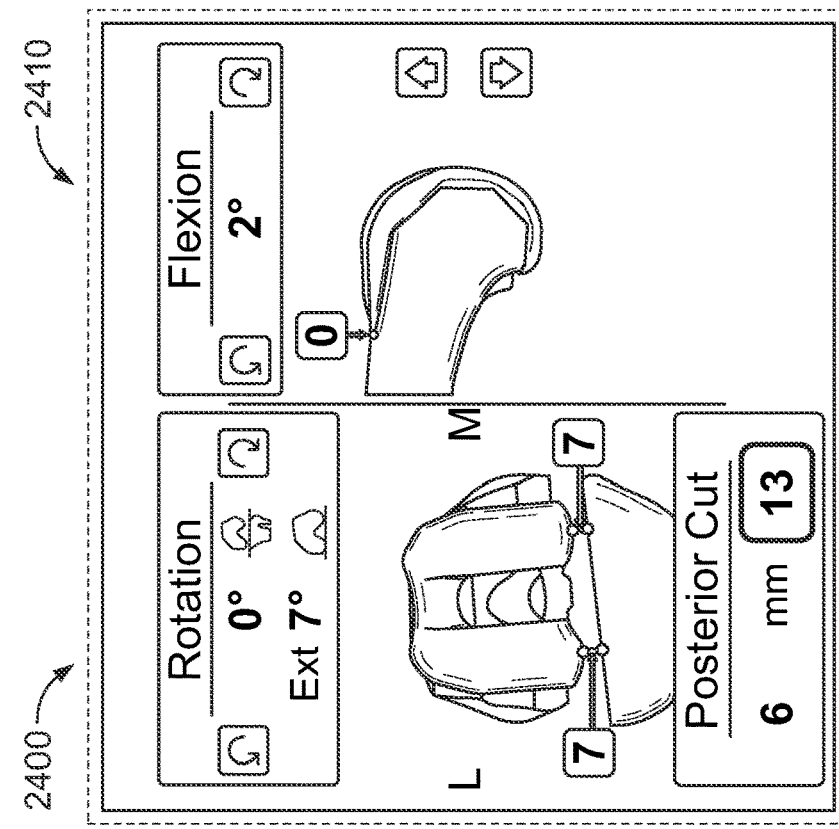

FIGS. 28A and 28B illustrate dependencies between surgical variables in accordance with one or more embodiments of the present disclosure. The initial rotation 2300 and flexion 2310 parameters may be outputted to the surgeon 15 along with the surgical variable table 2320 on the GUI 61 as shown in FIG. 28A. FIG. 28B illustrates the changes in rotation 2400 and flexion 2410 parameters as well as parameter table 2420 relative to FIG. 28A after the surgeon 15 simulates the impact of setting the flexion angle to 2° exactly. This may force the rotation range to be at 6° maximum, which may lead to an excessive posterior cut.

Figure 29:
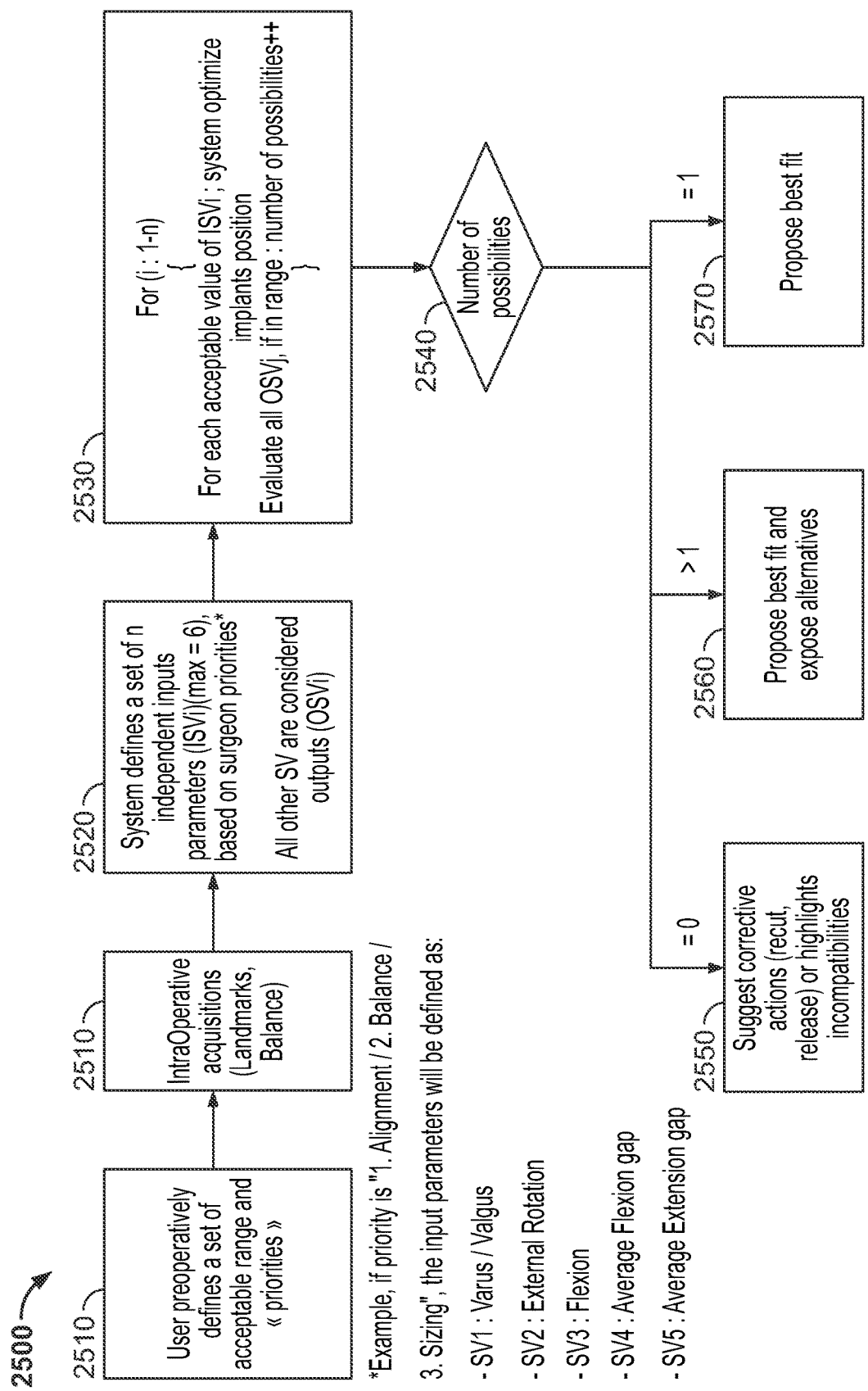
FIG. 29 is a flowchart describing a method for determining dependencies between surgical variables in accordance with one or more embodiments of the present disclosure.

FIG. 29 is a flowchart 2500 describing a method for determining dependencies between surgical variables in accordance with one or more embodiments of the present disclosure. In a step 2510, a user (e.g., the surgeon 15) preoperatively defines a set of acceptable ranges and priorities defining the weight between the functional parameters. In a step 2510, intraoperative acquisitions such as, without limitations, landmark, alignment, soft-tissue balance, for example, may be obtained. In a step 2520, the system (e.g., the controller 65) defined a set of n independent input surgical variable parameters (ISVi), where i is the index and n is an integer, based on surgical priorities. All other surgical variable parameters SV are considered output surgical variable parameters (OSVi).

In some embodiments, n=6 may be the maximum. In other embodiments, if the user-defined priorities are "1. Alignment/2. Balance/3. Sizing", the controller 65 may define the input parameters as:

SV1: Varus/Valgus
SV2: External Rotation
SV3: Flexion
SV4: Average Flexion gap
SV5: Average Extension gap In a step 2530, the controller 65 may execute an algorithm where:

```
For (i:1-n)
{
For each acceptable value of ISVi; system optimize
Implant position
Evaluate all OSVj, if in range:number of possibilities++
}
```

In a decision step 2540, if the controller 65 may assess that the number of possibilities are zero, in a step 2550, the controller 65 may suggest corrective actions (recut, release) or highlight incompatibilities.

In the decision step 2540, if the controller 65 may assess that the number of possibilities are greater than 1, in a step 2560, the controller 65 may propose a best fit and expose alternatives.

In the decision step 2540, if the controller 65 may assess that the number of possibilities is 1, in a step 2570, the controller 65 may propose a best fit.

With regard to selected arthroplasty modes that may impact intra and post-operative actions, joint arthroplasty typically follows universal rules, guidelines, recommendations that are mostly based on empirical medical knowledge. For example, during a TKA, the surgeon may elect to strictly align the implants along the mechanical axis and target for 3° of external rotation of the femoral component regardless of the diagnostic. Furthermore, patient rehabilitation after a joint procedure may follow pre-defined protocols regardless of the patient's unique situation.

In the embodiments disclosed herein, the CAS systems (e.g., the controller 65) may be used to develop mode-based arthroplasty programs as a pre-operative inputs based on patient-specific (e.g., subjective: patient and/or objective: wearable/measure), surgeon-specific, and health care infrastructure-specific information. The arthroplasty mode may be chosen from a list of different types of expected outcomes such as sport, range of motion, comfort, longevity, etc. The arthroplasty mode may define the subsequent decisions along the path of patient care such as: (1) selection of the implant, (2) definition of the functional parameters used for the definition of the surgical planning (Intra-operative), (3) definition of the rehabilitation program (Post-operative), (4) development of smart implants for joint indication, where the smart implants may be able to change at least one parameter in order to adapt to the proper mode such as sport, range of motion, comfort, longevity, etc. Furthermore, the smart implants may be adaptable based on an input from the joint recipient (e.g., through an app) or through self-detection of the activity.

Figure 30:
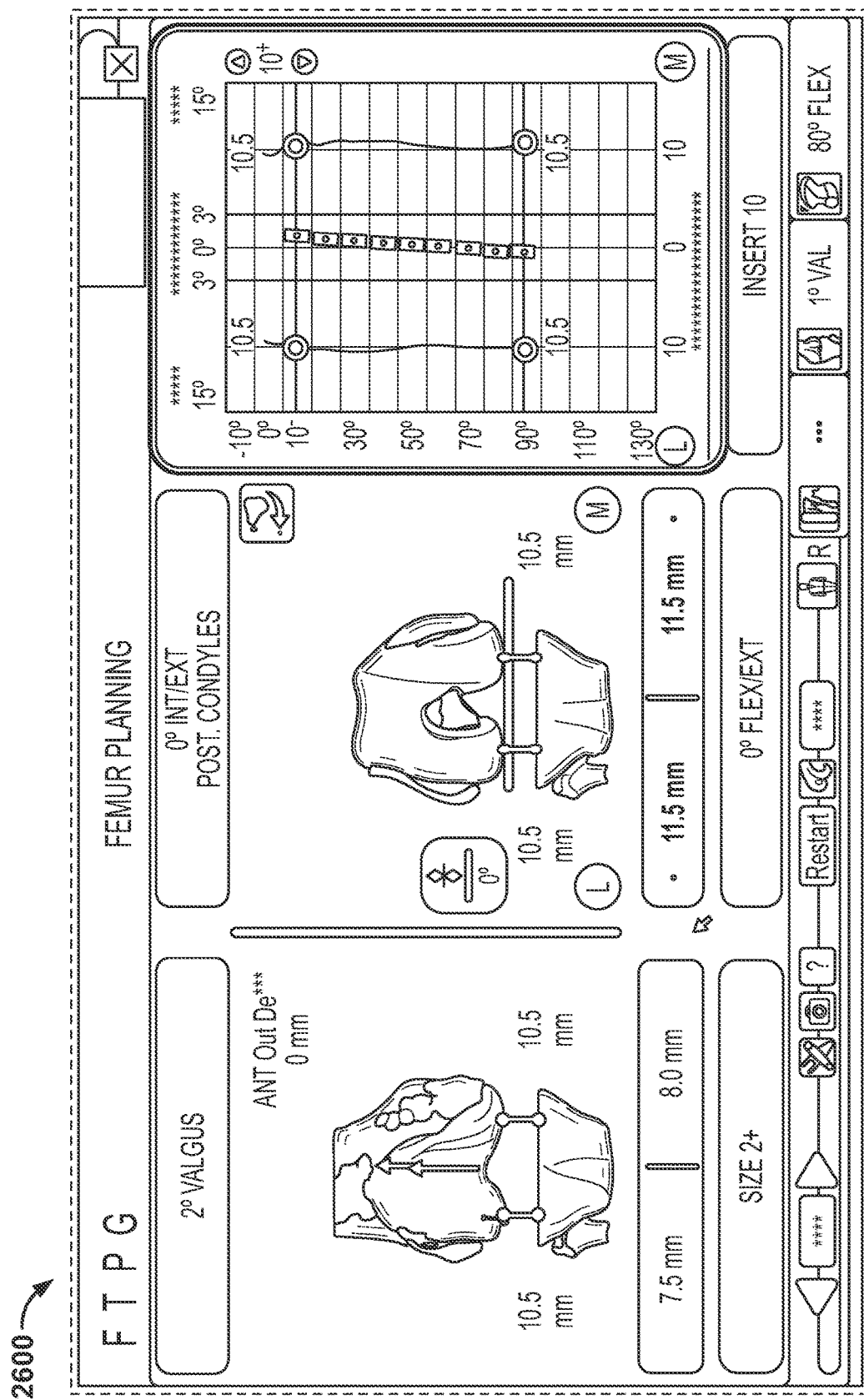
FIG. 30 is an exemplary snapshot of graphical user interface in accordance with one or more embodiments of the present disclosure.

FIG. 30 is an exemplary snapshot 2600 of the graphical user interface 61 in accordance with one or more embodiments of the present disclosure. The exemplary snapshot 2600 shown here exhibits a surgical plan displaying too much information due to the quantity of parameters in the displayed information to the surgeon 15 in contrast to the embodiments disclosed herein. For example, when there is too much displayed information (e.g., more than 30 items of distinct information) to the surgeon, the overload of displayed information may not answer the following questions to the surgeon 15 in real-time during the arthroplasty procedure such as what are the key parameters, what are the dependencies between these parameters, and what is the impact of these parameters on function?

Figure 31:
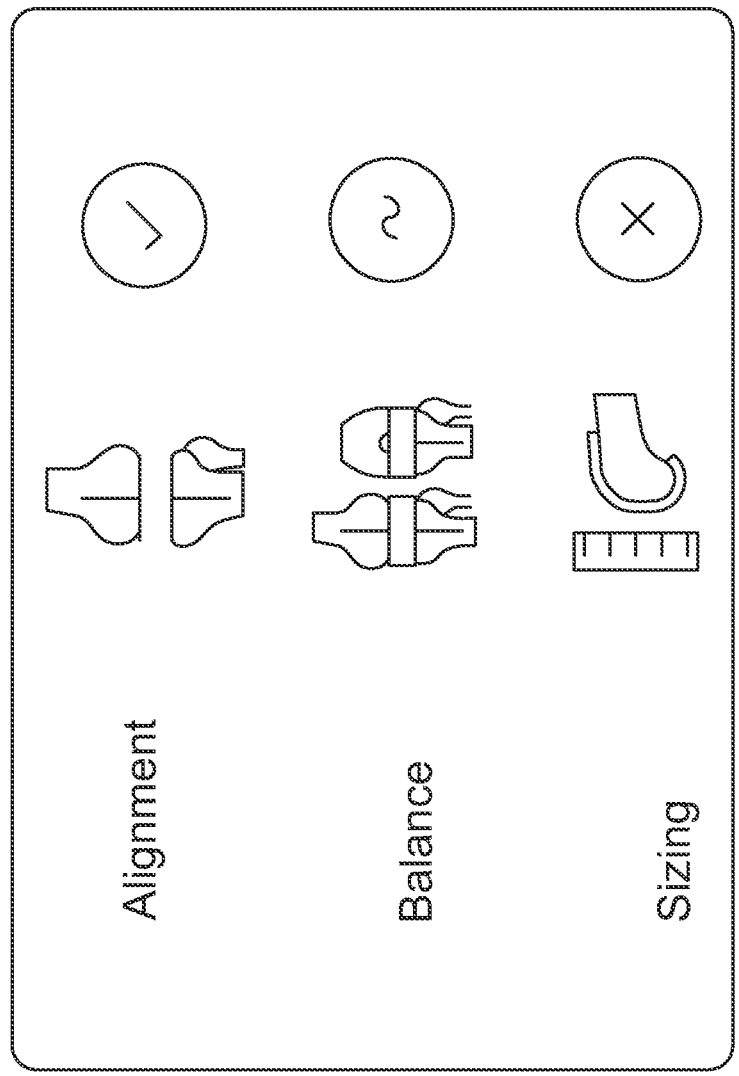
FIG. 31 shows graphical key performance indicators to display on a graphical user interface in accordance with one or more embodiments of the present disclosure.

FIG. 31 shows graphical key performance indicators 2700 to display on the graphical user interface 61 in accordance with one or more embodiments of the present disclosure. In some embodiments, the CAS system may offer to the surgeon a multi-layered communication of the surgical plan such as a summary of the fulfillment of the functional parameters using the graphical key performance indicators 2700. The graphical key performance indicators 2700 may include at least one indicator for indicating a fulfillment of alignment, balance, and/or sizing functional parameters.

Figure 32:
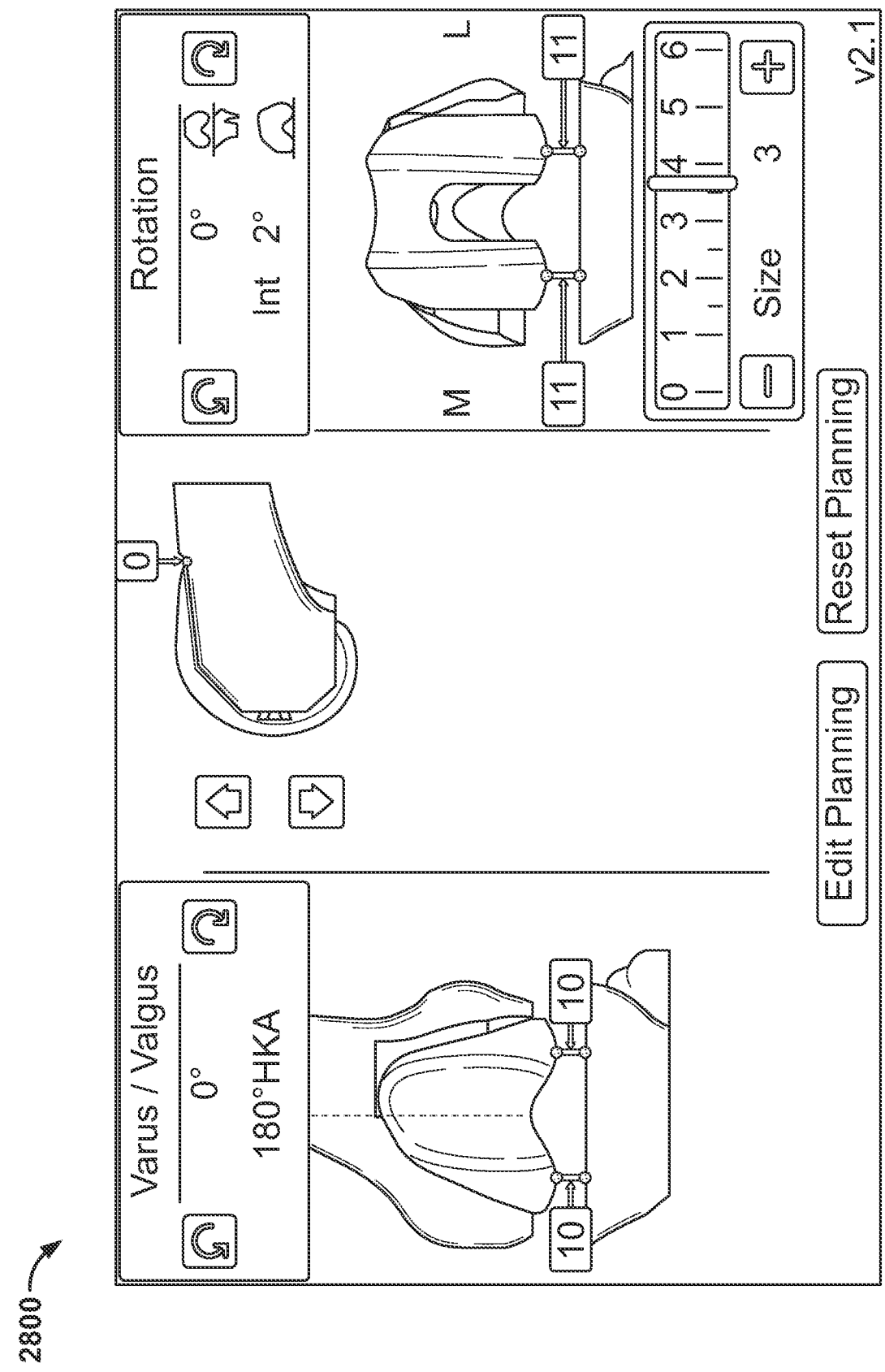
FIG. 32 shows an exemplary snapshot of a graphical user interface with planning subcomponents in accordance with one or more embodiments of the present disclosure.

FIG. 32 shows an exemplary snapshot 2800 of the graphical user interface 61 with planning subcomponents in accordance with one or more embodiments of the present disclosure. The planning subcomponents layer may include, for example, "Edit Planning" and "Reset Planning" icons.

Figure 33:
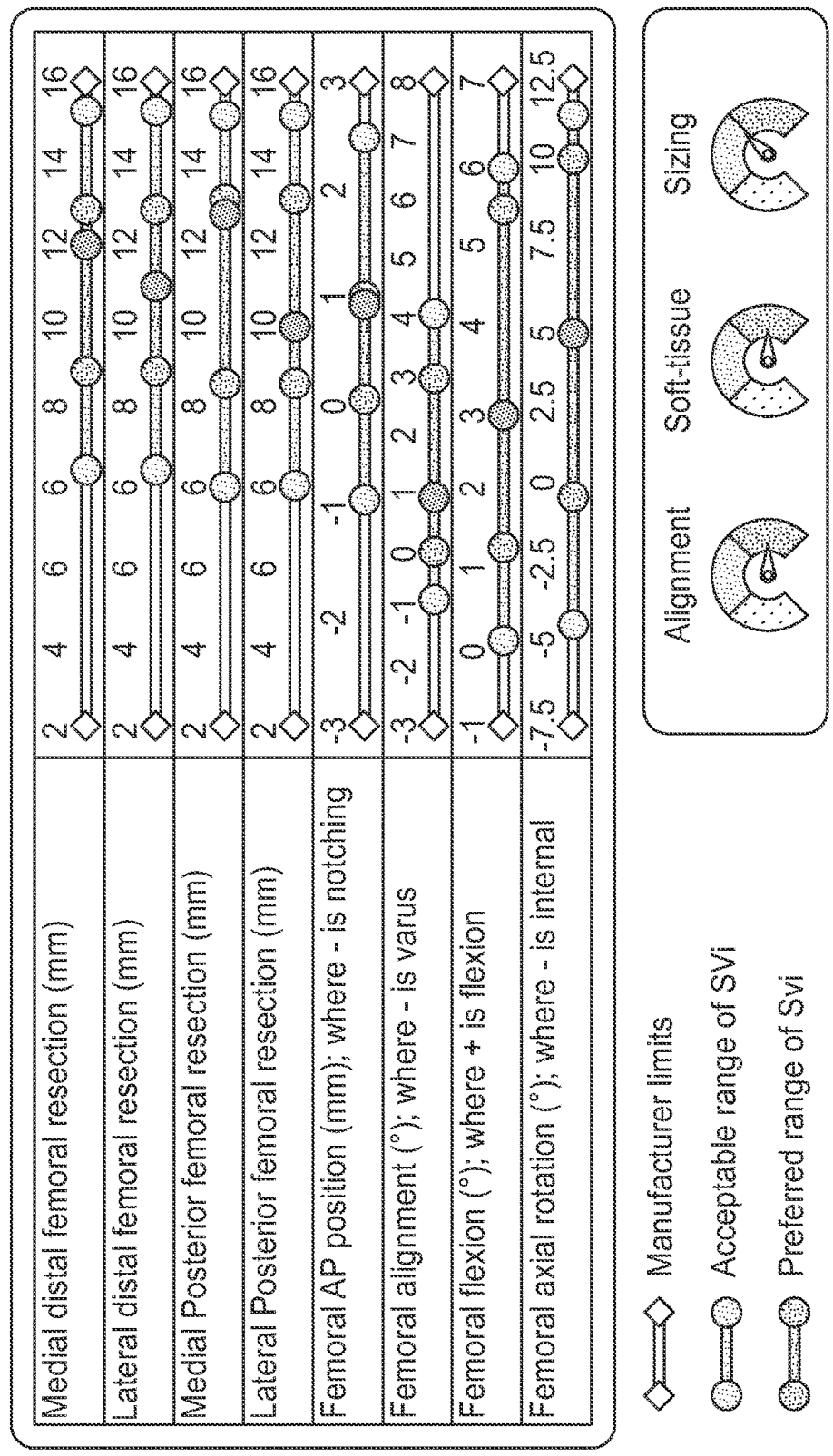
FIG. 33 shows an exemplary snapshot of a graphical user interface with an overview of the surgical variables in accordance with one or more embodiments of the present disclosure.

FIG. 33 shows an exemplary snapshot 2900 of the graphical user interface 61 with an overview of the surgical variables in accordance with one or more embodiments of the present disclosure.

Figure 34:
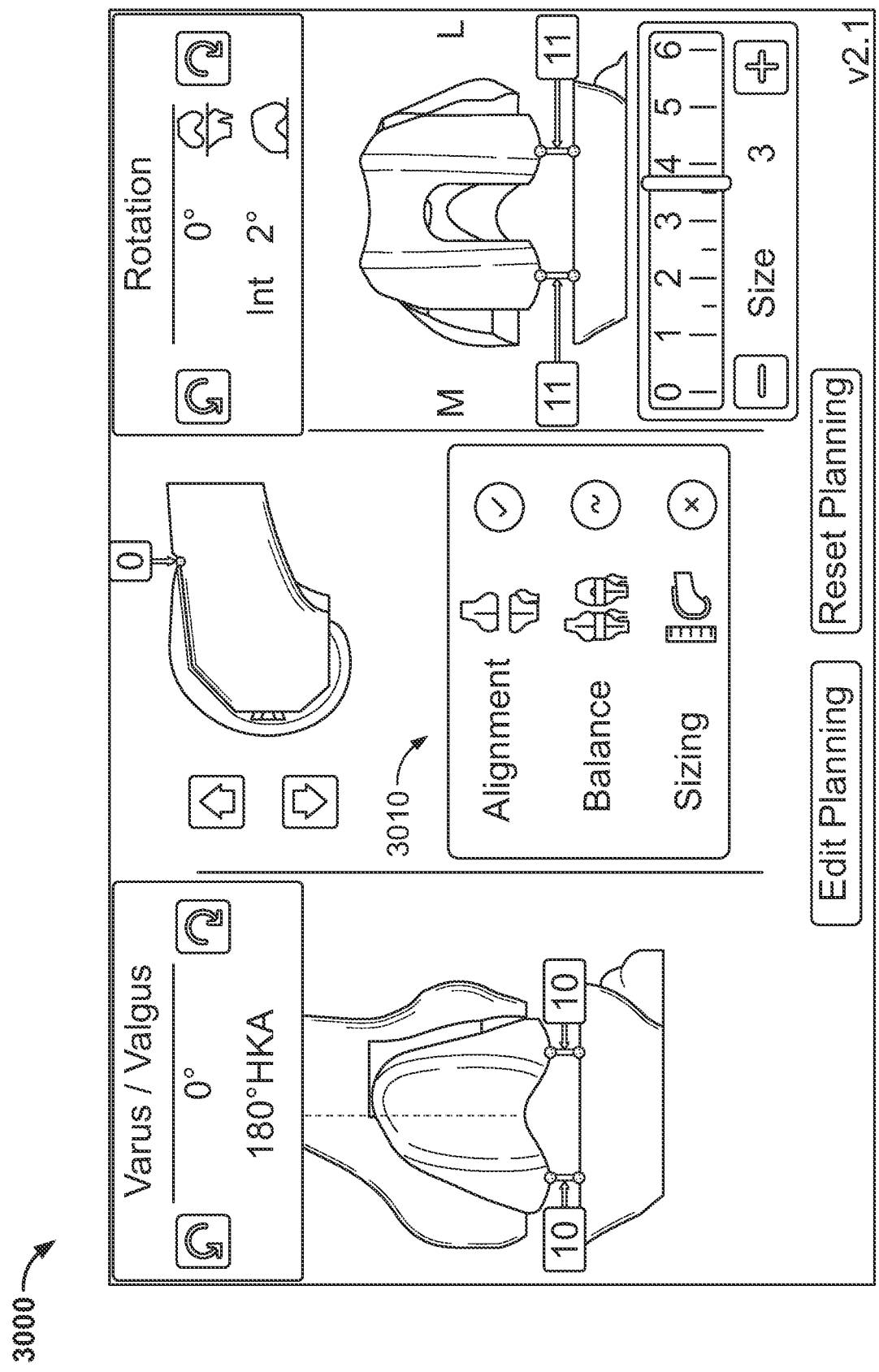
FIG. 34 shows an exemplary snapshot of a graphical user interface with a combination of display layers in accordance with one or more embodiments of the present disclosure.

FIG. 34 shows an exemplary snapshot 3000 of the graphical user interface 61 with a combination of display layers in accordance with one or more embodiments of the present disclosure. The combination of the display layers may include graphical key performance indicators 3010.

There may be occurrences where the suggested surgical plan, even when optimized based on the inputs, may not fulfill the requirements from the surgeon such as cut parameters that would need to be outside the range of acceptable cut parameters, for example.

In some embodiments, the controller 65 may be configured to include parameters of a plurality of implants that the surgeon may use in the surgical planning tool display on the GUI 61. The GUI 61 may offer a kit of implants (e.g., femoral component or tibial insert) for a joint replacement (e.g., knee) available under different articular geometries in terms of form, shape and/or position relative to a reference such as for example, a portion of the implant in contact with bone cut(s), so the surgical plan may be optimized without having to compromise the desired range of cut parameters. The algorithms executed by the processor 70 in the controller 65 may leverage additional inputs (i.e., kit of implants) to formulate both an optimized surgical plan as well as an implant selection from the implant kit.

In some embodiments, the component kit may include, for example, a femoral component and/or a tibial insert that may be available under different articular geometries than the regular and standard implants as an attempt to improve the management of the soft-tissue balance through the arc of motion, most notably in mid-flexion.

In some embodiments, the different articular geometries may relate to a particular portion of the articular surface between 0° and 90° of flexion, preferably between 20° and 70°, and most preferably between 35° and 55° of flexion; where the implant difference may be expressed in terms of curvature, and/or shape, and/or position relative to the bone cut.

In some embodiments, the different articular geometries may be applied to one compartment of the considered implant component. In other embodiments, the different articular geometries may be applied to both compartments of the considered implant component. In yet other embodiments, the different articular geometries may be applied to one compartment of the considered implant component, while different articular geometries may be applied to the other compartment of the considered implant component.

In some embodiments, regular implants may be available under different configurations in terms of regular parameters such as constraint level, size, side, ligament retaining or not, etc. For a given configuration, the implant component kit may offer additional custom components with particular material build-up; where the build-up may be gradual in nature. For example, a build-up at "40° of flexion" may range from 5° of flexion (i.e., start of the transition from regular condylar geometry to build-up) to 75° of flexion (i.e., end of the transition from build-up to regular condylar geometry), but the maximum build-up thickness may be at 40° of flexion. In some embodiments, the thickness of the material build-up may fluctuate depending on the expected level of correction of the laxities 3200, with its local maximum between 1 and 4 mm. In other embodiments, a local minimum may be between 2 and 3 mm. Also, the location of the build-up may fluctuate depending on the indication. In this regard, the local maximum thickness may relate to a particular angle of flexion (e.g., 30° of flexion) and/or to a range of angles of flexion (e.g., from 40° to 60° of flexion).

FIGS. 35A-35C illustrate components of an implant component kit in accordance with one or more embodiments of the present disclosure. Implant component 3100 may include a gradual 1.5 mm build-up on both condyles at 45° of flexion. Implant component 3110 may include a gradual 3 mm build-up on both condyles at 45° of flexion. Implant component 3120 may include a gradual 1.5 mm build-up on one condyle at 45° of flexion.

In some embodiments, the planning page shown on the GUI 61 may display the laxities curves associated with the different implants from the implant kit for a given implant configuration. In such a case, the surgeon 15 may make a choice of the perceived optimal implant.

In some embodiments, the algorithm executed by processor 70 may select the implant from the implant kit resulting in the most preferable planning as based on the surgeon's preference.

FIGS. 36A-36C show an impact on the surgical plan with and without using the implant kit in accordance with one or more embodiments of the present disclosure. FIG. 36A may show the laxity curves 3200 using the standard implant kit. While the cut parameters as well as the position and orientation of the femoral component may be within the preferred range, the laxity curves (i.e., gaps acquired under constant force through arc of motion) show an increased gap around 45 deg of flexion, which may translate into mid-flexion instability In some embodiments, using the implant 3220 as shown in FIG. 36C, FIG. 36B shows an improvement of the laxity curves 3210 using the same cut parameters as well as position and orientation of the femoral component by selecting the implant 3220 from the kit with material build-up around 40 deg of flexion.

Figure 37:
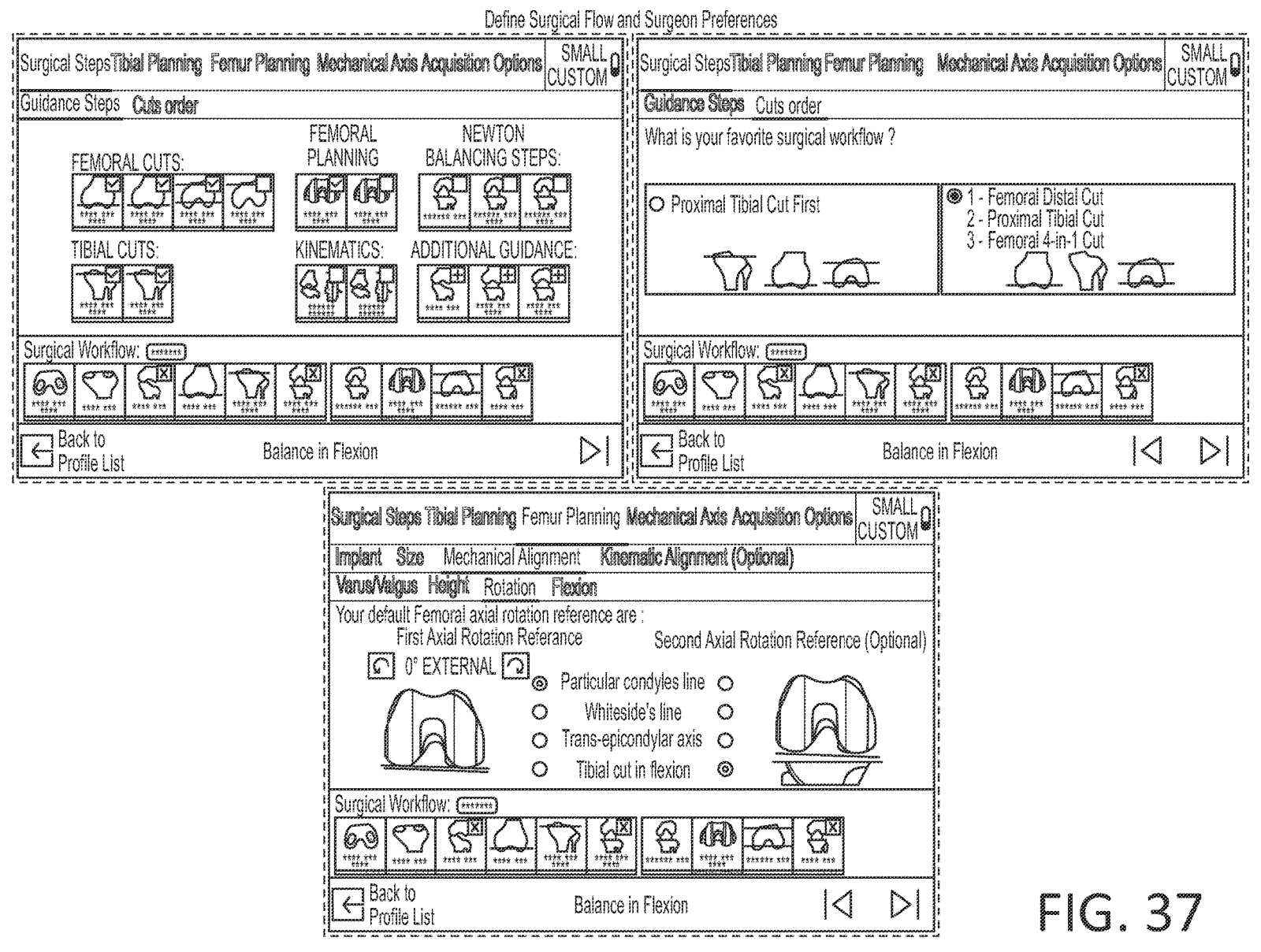
Figure 37:
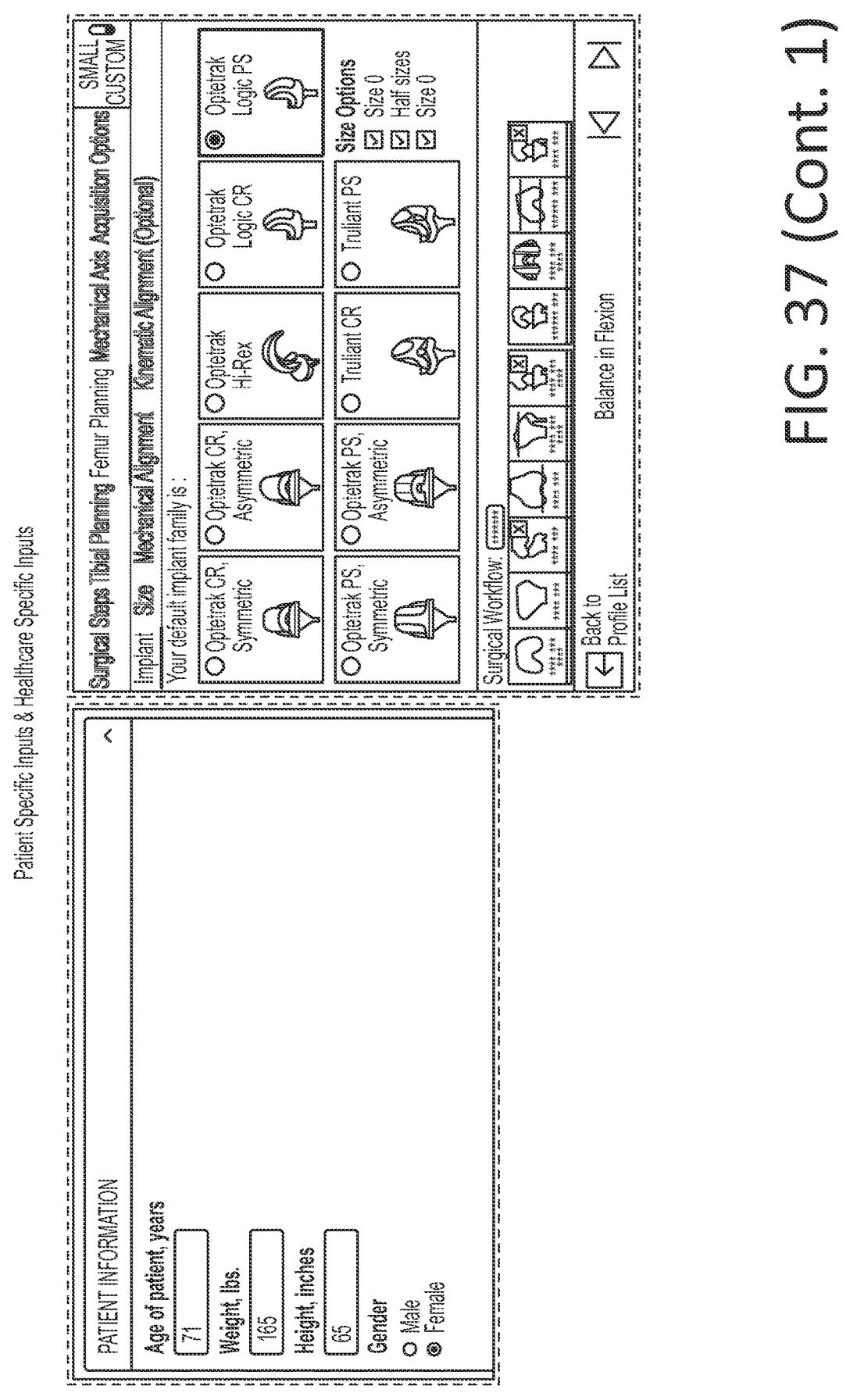
Figure 37:
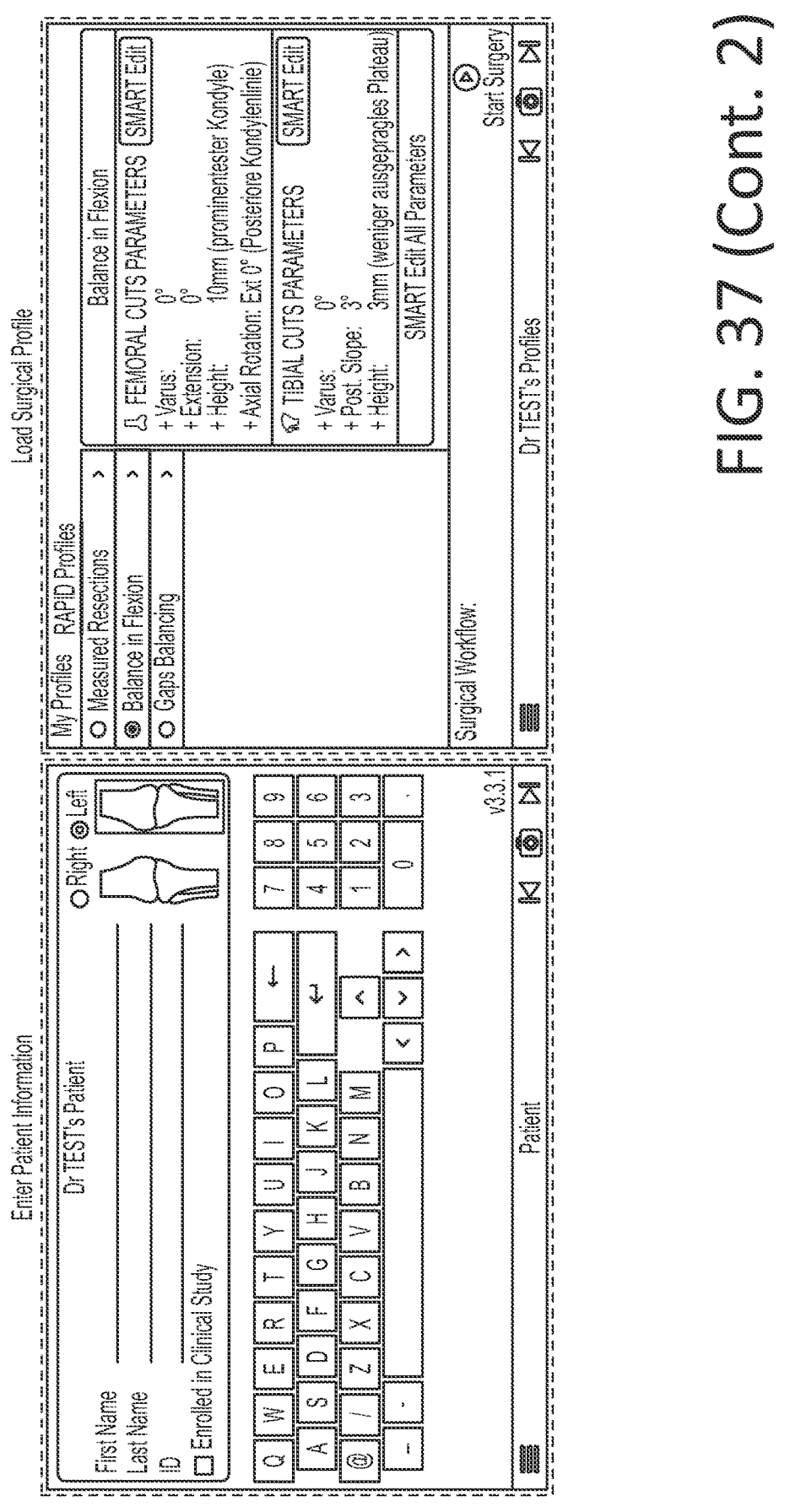

FIG. 37 illustrates a first exemplary top-level view 3300 of an implant planning software tool in accordance with one or more embodiments of the present disclosure. The first exemplary top-level view 3300 may be displayed on a computing device associated with the surgeon 15 either inside and/or outside of the operating room, for example, displayed on the GUI 61 of the display 60 to plan for the joint arthroplasty procedure and to assist the surgeon during the arthroplasty procedure. The first exemplary top-level view 3300 may include clickable pictorial icons such as icons for defining the surgical flow and surgeon preferences, patient specific inputs and healthcare specific inputs, an icon for accessing patient information, an icon to load a surgical profile, an icon for managing intraoperative joint registration data and images, Newton Acquisition, a femoral component location plan, a Newton Trial Acquisition, and an icon to generate a postoperative report.

FIG. 38 illustrates a second exemplary top-level view 3400 of an implant planning software tool in accordance with one or more embodiments of the present disclosure. The second exemplary top-level view 3400 may include a clickable icon-based interface for calling software modules and/or other nested menus. The second exemplary top-level view 3400 may be displayed on a computing device associated with the surgeon 15 either inside and/or outside of the operating room, for example, displayed on the GUI 61 of the display 60 to plan for the joint arthroplasty procedure and to assist the surgeon during arthroplasty procedure. The second exemplary top-level view 3400 may include the patient's name, a patient profiler 3410, a patient history 3415, a joint image library 3420 of the patient, a bone registration and joint movement data 3425 library for the patient, healthcare specific preferences 3430, surgeon-specific preferences 3435, a ligament balancing device library 3450, an implant component kit 3455, a surgical tools library and robotic control information 3460, a menu for setting arthroplasty mode parameters 3465, a general patient database 3470 accessible to the surgeon, an interactive surgical plan generator 3475, a robotic control instructions upload 3480 command to upload software instructions for controlling controllers and/or actuators of a robotic surgical theater, an icon 3485 to synchronize current post-operative patient results to databases (e.g., may be used to train machine learning models), an icon 3490 to upload the interactive surgical plan to the operating theater computer 65 for the surgeon 15 to interact with on GUI 61 during the arthroplasty procedure, and an icon 3495 to access a post-operative patient monitoring of the joint replacement and rehabilitation program of the patient.

At the time of the trial reduction, according to a conventional method, the surgeon may manually apply force to the knee joint (i.e., stress varus/valgus test) to assess the lateral and the medial gaps at the joint line. Based on this subjective examination, important surgical decisions may be made that may influence the overall knee stability such as the tibial insert thickness. Recent studies have concluded that based on inter-observer evaluations, there may exist 1-2 mm of variation in the choice of insert thickness and a standardization of the assessment may be recommended. Also, a trial reduction according to different thicknesses of inserts (e.g., 9 mm, then 10 mm, then 11 mm, finally 10 mm) may be very time consuming.

Therefore, to provide a technical solution to the technical problems posed by these conventional methods, an alternative method may leverage soft-tissue information acquired during the surgery to issue personalized recommendations regarding the selection of the tibial insert component. While the following embodiments described hereinbelow particularly relate to the thickness of the tibial insert, similar approaches may be implemented for other parameters such as the constraint level of the tibial insert.

In some embodiments, soft tissue balancing may play an important role in total knee arthroplasty (TKA) which may affect both short and long term post-operative clinical outcomes. One of the factors that may ensure a successful soft tissue assessment is the thickness of the tibial insert, which is an intraoperative surgical decision that may vary based on surgeon experience and preference. There is a paucity of information for determining the proper tibial insert thickness intraoperatively; thus, a study was made to 1) test the correlation between laxity curves (i.e., compartment-specific joint gaps obtained under distraction force of the joint throughout the arc of motion) and selected tibial insert thickness, and to 2) build surgeon-specific models to predict tibial insert thickness.

In some embodiments, the study cohorts included 273 cases using an instrumented computer-assisted orthopedic surgery (CAOS) system (ExactechGPS, Blue-Ortho, Meylan, FR) with a tibia first technique performed by 24 different surgeons without any exclusions. During trial reduction, a trial femoral component was impacted onto a prepared distal femur and a novel intra-articular tibial distractor was introduced into the joint space, which applied a quasi-constant distraction force once released regardless of the joint gap. Then, the limb was manually manipulated through a full arc of motion and the corresponding joint laxities were recorded by the CAOS system. Medial and lateral (ML) gaps may be measured from 0° to 120° of flexion at 5° or 10° increments. A correlation coefficient between tibial insert thickness and medial/lateral gaps may be calculated at each available flexion on a surgeon-specific basis. For each surgeon, the flexion that was associated with the highest correlation between either the medial or lateral gap and tibial insert thickness may be selected to train the predictive model.

In some embodiments, with regard to predictive recommendation of the tibial insert thickness, data management may include surgeons with more than 5 cases in the database, and medial and lateral gaps at certain degrees of flexion (0°, 5°, 10°, 15°, 20°, 30°, 45°, 60°, 75°, 90°, 105°, and 120°).

In some embodiments, a method for providing a predictive recommendation of the tibial insert thickness may include (1) calculating a correlation coefficient 'r' at each degree of flexion for each surgeon, (2) selecting degree of flexion that gives the highest 'r' for both medial and lateral gaps for each surgeon, and (3) building models using medial and lateral gaps as predictors with tibial insert thickness as the outcome using (but not limited to) the following statistical models: Random forest and ordinal logistic regression model.

In some embodiments, two statistical models used in this study were random forest and ordinal logistic regression model. The study is not limited to these two statistical models. Additional statistical model types may be used. A random forest model may adaptively avoid overfitting and may exhibit better prediction performance as it is subjected less to model assumption requirements according to some studies. On the other hand, an ordinal logistic regression model may be more favorable in situations with small sample sizes. For each surgeon, data may be divided into training and testing datasets with a ratio of 2:1. Predictors of the model may be defined as medial and lateral gaps. Accuracy of models may be evaluated by calculating proportions of exact predictions, predictions within 1 mm, and predictions within 2 mm using testing datasets.

Figure 39:
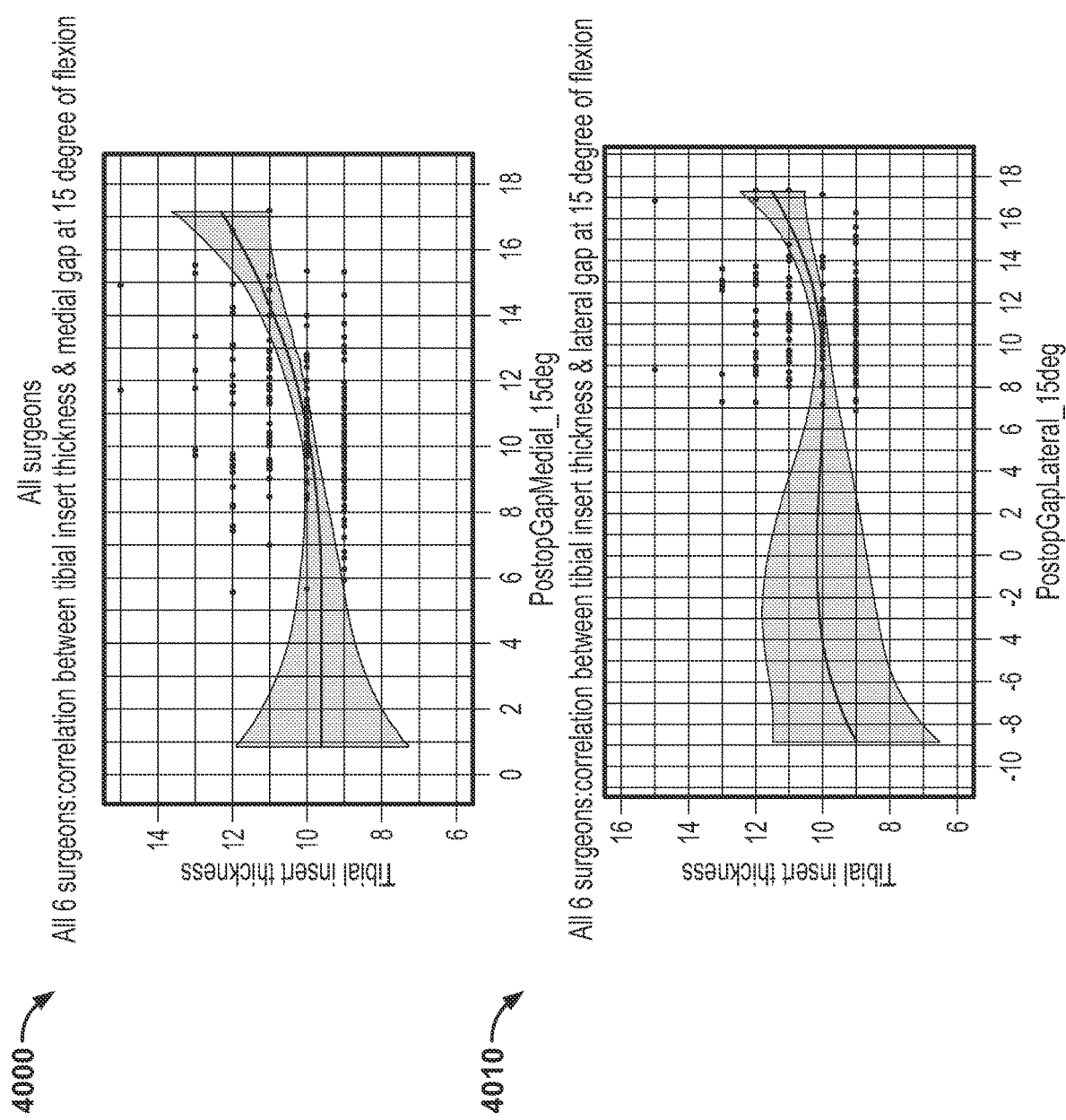
FIG. 39 shows graphs exhibiting correlations between the tibial insert thickness and the medial/lateral gaps at 15 degrees of flexion in accordance with one or more embodiments of the present disclosure

FIG. 39 shows graphs exhibiting correlations between the tibial insert thickness and the medial/lateral gaps at 15 degrees of flexion in accordance with one or more embodiments of the present disclosure. A graph 4000 shows the correlation for all surgeons (e.g., 6 surgeons in this case representing a total of 203 cases) between tibial insert thickness and medial gap at 15 degrees of flexion. A graph 4010 shows the correlation for all surgeons (e.g., 6 surgeons in this case) between tibial insert thickness and lateral gap at 15 degrees of flexion. This graph established the lack of correlation when the surgeons are pooled.

Figure 40:
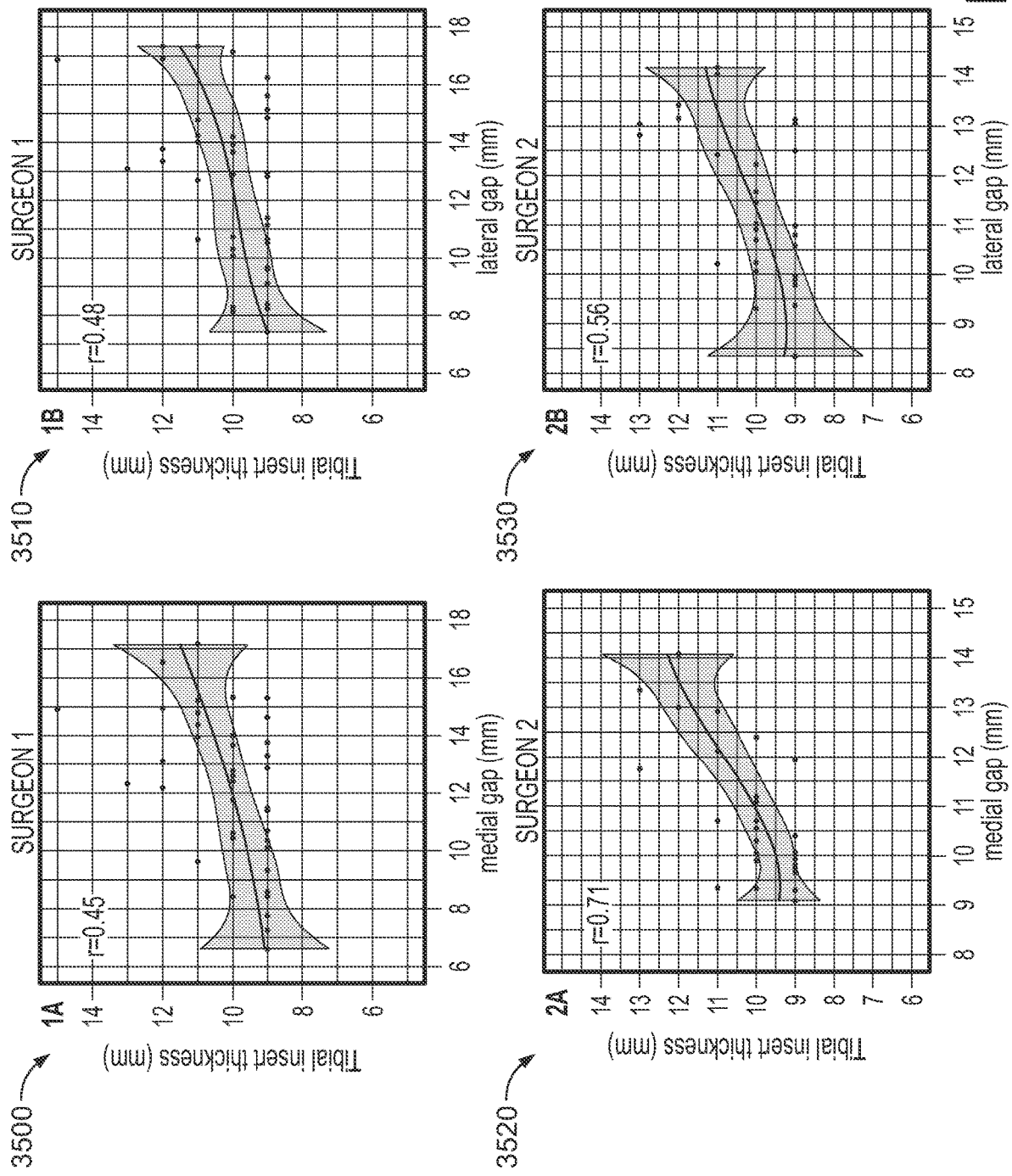
FIG. 40 illustrates four graphs of the tibial insert thickness versus medial and lateral (ML) gaps for two surgeons in accordance with one or more embodiments of the present disclosure.

FIG. 40 illustrates four graphs of the tibial insert thickness versus medial and lateral (ML) gaps for two particular surgeons selected among the 6 surgeons associated with 203 cases in the correlation analysis based on their sample sizes of available tibial insert thickness. The data from the first surgeon (i.e., surgeon 1) may be shown in graphs 3500 and 3510. The data from the second surgeon (i.e., surgeon 2) may be shown in graphs 3520 and 3530.

FIG. 41 shows a table 3600 illustrating a summary of predictive model accuracy on testing datasets for the two surgeons in accordance with one or more embodiments of the present disclosure. The two surgeons showed relatively high correlation between ML gaps and tibial insert thickness at 15° of flexion with correlation coefficients of 0.45/0.48 and 0.71/0.56 as shown in FIG. 40. For surgeon 1, the random forest model exhibited higher exact prediction accuracy of tibial insert thickness than the original logistic regression model (39% vs 31%) while for surgeon 2, the ordinal logistic regression model was 9% more accurate than random forest as shown in the table 3600. Both models exhibited high accuracy in predicting tibial insert thickness within 1 mm and 2 mm difference.

In some embodiments, this study first investigated correlation between the knee joint laxity and tibial insert thickness in TKA with a tibial-first technique. The findings demonstrated that the relationship tended to be surgeon-specific. For example, while these two particular surgeons had the highest correlation at 15 deg of flexion, for other surgeons (among the 6 surgeons), the highest correlation was observed at 105 deg of flexion. Predictive models built with both random forest and ordinal logistic regression methods were shown to be accurate based on surgeons with high correlation between joint gaps and tibial insert thickness. These models may guide surgeons to select the proper thickness of the tibial insert during the surgery, which may not only provide a more efficient way in terms of making surgical decisions, but also may ensure joint stability post-operatively. In addition, the pro-active recommendation of a tibial insert thickness has a potential to streamline the surgical workflow by eliminating the need for sequential trials with different thicknesses and therefore to reduce the overall surgery time. Sample size may be one of the limitations of this study which may impact the model training process and testing results. Other potential predictors of tibial insert thickness may be used to improve the performance of the predictive models.

Figure 42:
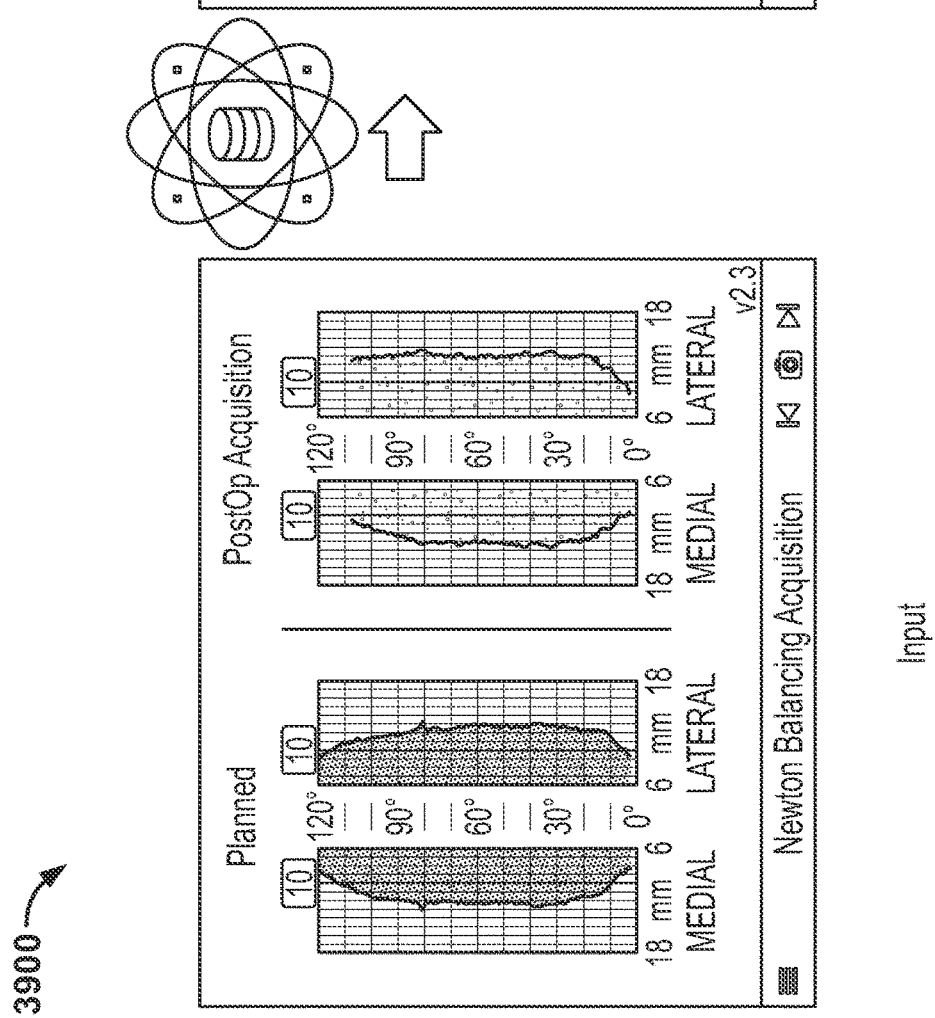
FIG. 42 is a schematic diagram illustrating a machine learning model configured to output a recommended tibial insert thickness in accordance with one or more embodiments of the present disclosure.

FIG. 42 is a schematic diagram 3900 illustrating a machine learning model configured to output a recommended tibial insert thickness in accordance with one or more embodiments of the present disclosure. The predictive model such as the surgical plan generator model 75 which may further use a machine learning model may be configured to (e.g., trained to) recommend an insert thickness based on the acquired post-op laxity curves, so that the user may directly start the trial reduction at this stage.

In some embodiments, with regard to predictive compensation due to changes in the soft tissue envelope, at the time of the acquisition of the joint laxities for the set-up of the planning for the definition of the bone cut parameters, the surrounding soft-tissue envelope may be at an initial condition, which may be different than the final condition after the components or trial components may be placed. A proposed prediction (e.g., using the surgical plan generator model 75 of FIG. 2 and/or any suitable machine learning model 77) of the expected impact of the change of the surrounding soft-tissue envelope condition on the joint gaps may be proactively integrated into the set-up of the planning.

In some embodiments, at the time that the acquisition of the joint laxities may be performed after the proximal tibial cut and may be used for the definition of the femoral cut parameters planning, the posterior capsule may not be accessible and/or aspects of the meniscus horns may still be attached to the tibia and/or to the femur mostly on the lateral side. After preparation of the distal extremity of the femur, the knee joint may be accessible, and then (1) the menisci may be fully removed from the tibia and/or the femur and (2) the posterior capsule may be released. Such subsequent change(s) to the condition of the surrounding soft-tissue envelope may translate into a change of the joint gaps in terms of the opening/dimension as well as the mediolateral distribution. Therefore, the expected change(s) of the joint gaps at the time of the set-up of the planning may be considered.

Figure 43:
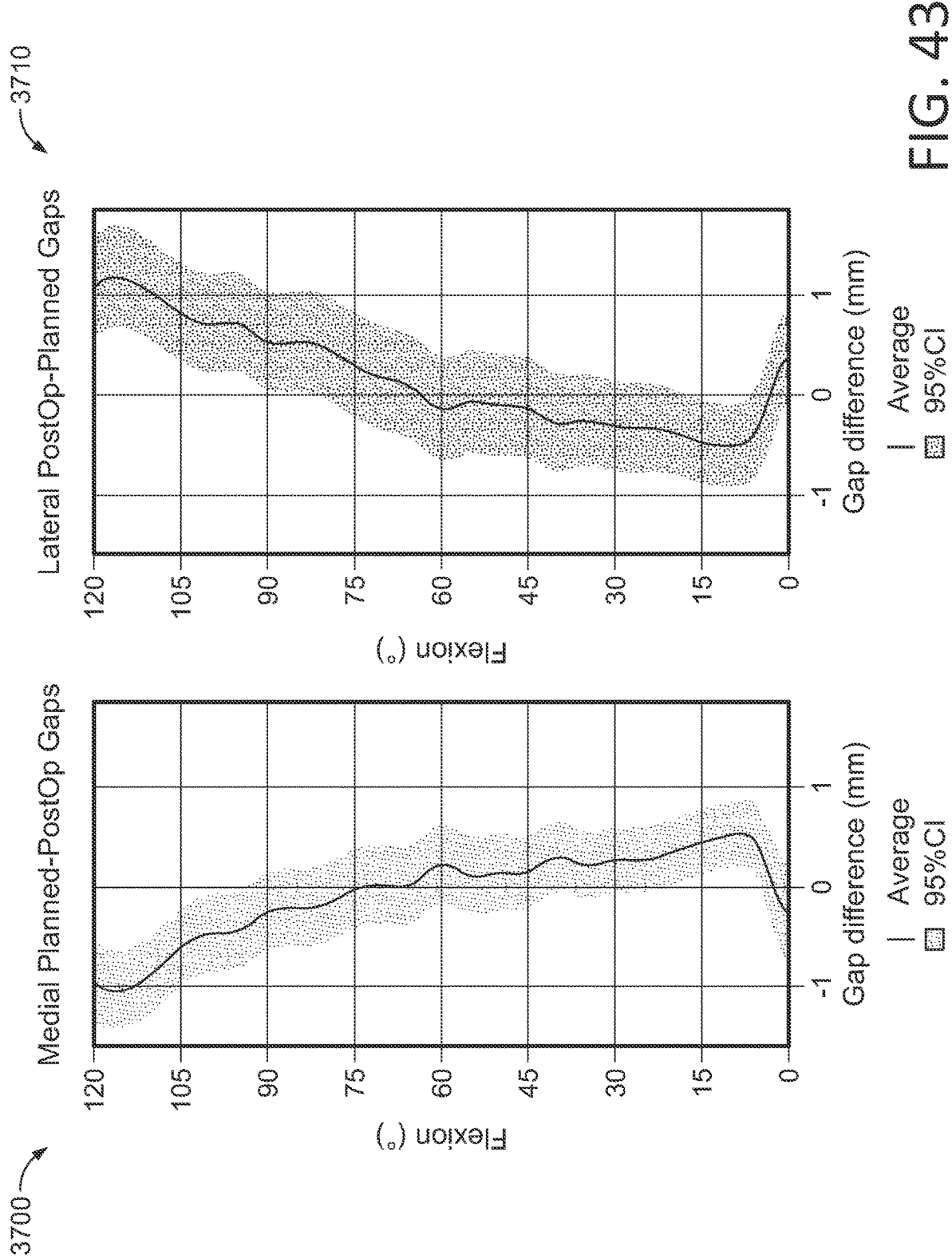
FIG. 43 illustrates a first graph of medial planned-postoperative gaps and a second graph of lateral planned-postoperative gaps in accordance with one or more embodiments of the present disclosure.

FIG. 43 illustrates a first graph 3700 of medial planned-postoperative gaps and a second graph 3710 of lateral planned-postoperative gaps in accordance with one or more embodiments of the present disclosure. A retrospective study based on 136 cases of an evaluation of the gaps at two stages: (1) "Planned": Laxity per the planning and (2) "Post-op": Laxity at the trial reduction stage (after femoral preparation). The first graph 3700 and the second graph 3710 illustrate observed linear opening of the gaps (up to ~1.2 mm) from 60° to ~120° of flexion with a narrow 95% confidence interval (CI) band indicative of high predictability.

Figure 44:
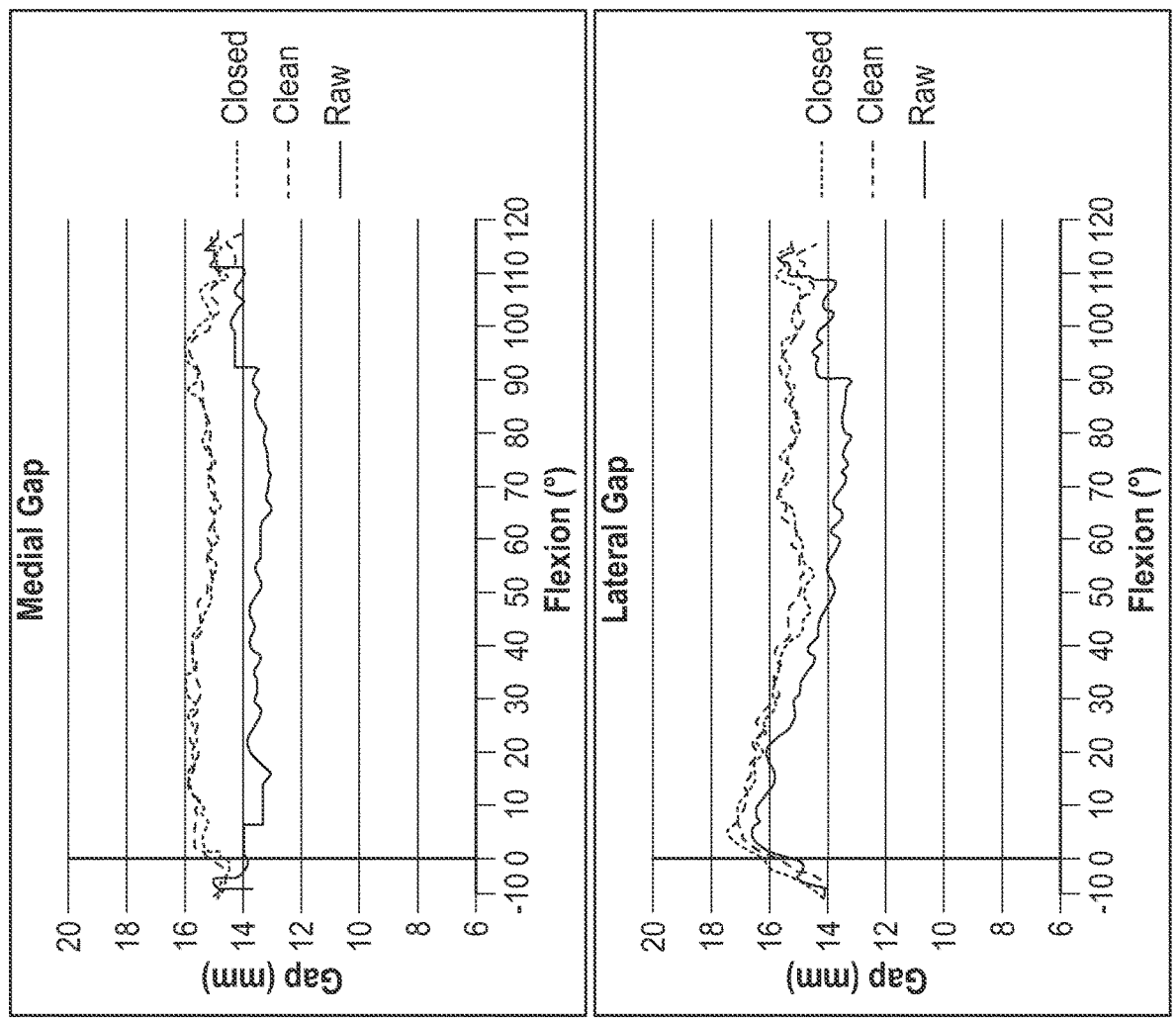
FIG. 44 illustrates a first graph plotting medial gap against flexion angle and a second graph plotting lateral gap against flexion angle in accordance with one or more embodiments of the present disclosure.

FIG. 44 illustrates a first graph 3800 plotting medial gap against flexion angle and a second graph 3810 plotting lateral gap against flexion angle in accordance with one or more embodiments of the present disclosure. The data in the two graphs are based on a cadaveric study of the evaluation of the impact of the meniscus removal on the flexion gap at the time of the 4-in-1 cuts (Inter-observer and intra-observer study). The "Raw" trace is data before the full removal of the menisci, and the "Clean" trace is data after full removal of the menisci. The data confirms an opening of ~1.5 mm of the gaps at 90° of flexion.

In some embodiments, at the time of the definition of the femoral surgical plan, the status of the soft-tissue envelope may be considered in order to predict the impact of the anticipated change into the surgical plan. For example, this may assume that subsequent removal of the meniscus attachments may open the knee joint by ~X mm at 90° of flexion; where X is expected to be between 0.25 mm and 1.75 mm, preferable about 1 mm. This may also assume that the surgeon may expect for the final gaps in flexion to be the same as the gaps in extension (e.g., 10 mm for both). At the time of the femoral planning, the femoral cut parameters may be based on flexion gaps being X mm smaller than the extension gaps as an attempt to consider the impact of the subsequent change(s) to the soft-tissue envelope.

Figure 45:
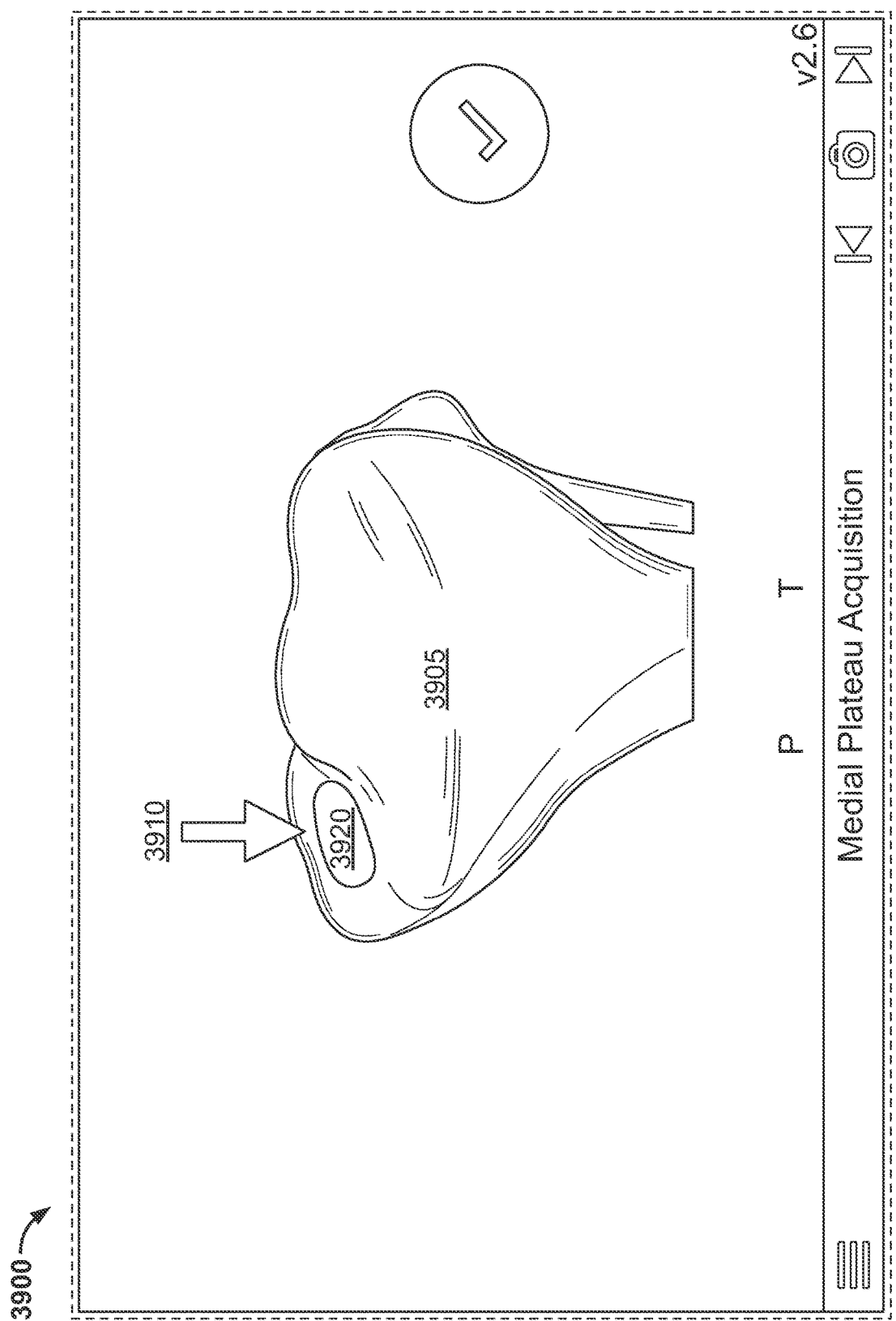
FIG. 45 illustrates a snapshot of a graphic user interface for registration of a first bone member in accordance with one or more embodiments of the present disclosure.

FIG. 45 illustrates a snapshot 3900 of the graphic user interface 61 for registration of a first bone member 3905 in accordance with one or more embodiments of the present disclosure. The GUI 61 may display a portion of the tibia 3905, such as the medial plateau 3920, for example. The user such as a surgeon may use a pointer as an input device 92 to touch the medial plateau 3920 on the display 60 as shown by the arrow 3910. The controller 65 may receive the instruction from the pointer input device 92. The controller 65 may acquire bone registration data for example at the medial plateau 3920, or at any other position on the tibia 3905 when touched by the pointer input device 92.

Figure 46:
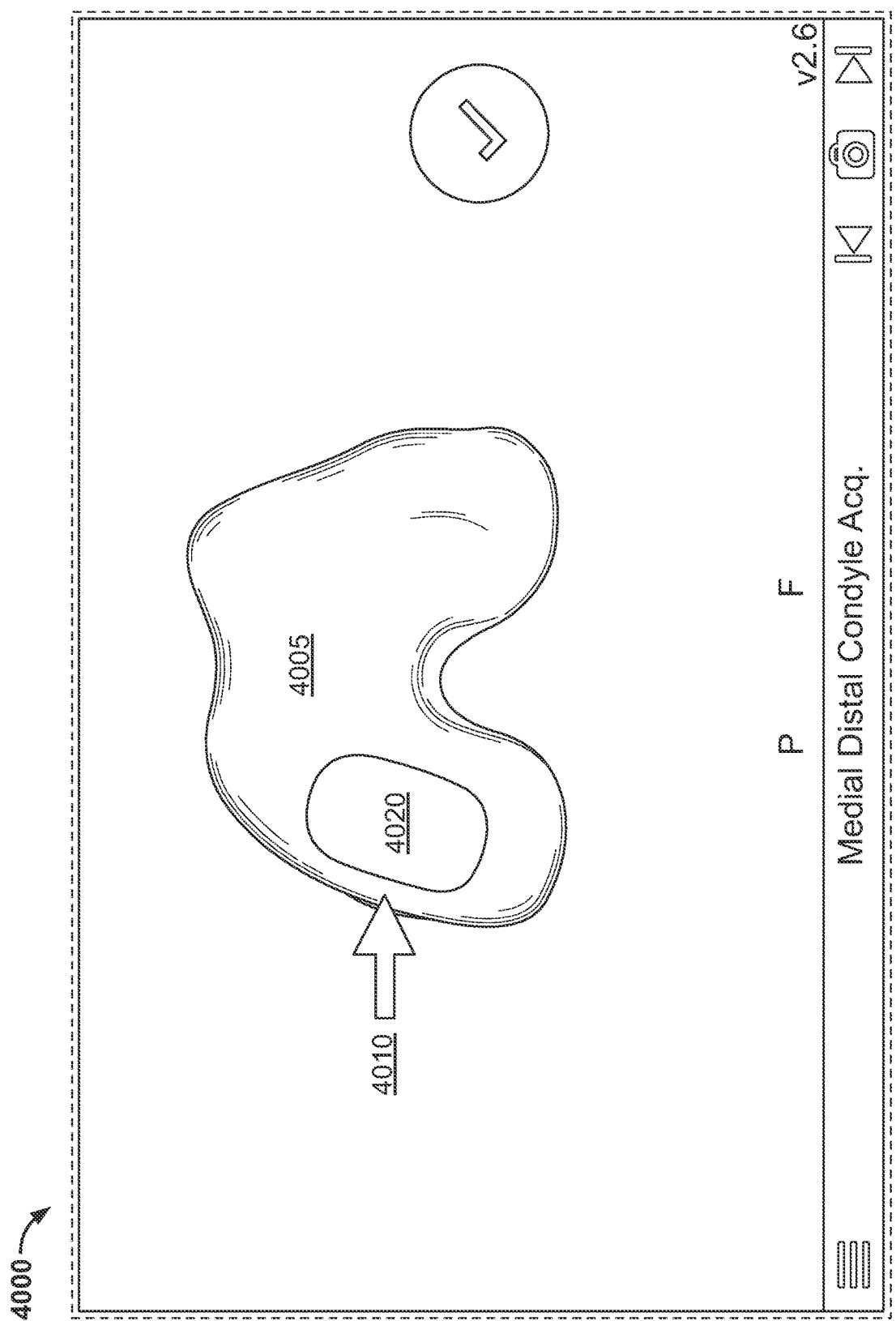
FIG. 46 illustrates a snapshot of graphic user interface for registration of a second bone member in accordance with one or more embodiments of the present disclosure.

FIG. 46 illustrates a snapshot 4000 of the graphic user interface 61 for registration of a second bone member 4005 in accordance with one or more embodiments of the present disclosure. The GUI 61 may display a portion of the femur 4005, such as the medial distal condyle 4020, for example. The user such as a surgeon may use a pointer as an input device 92 to touch the medial distal condyle 4020 on the display 60 as shown by the arrow 3910. The controller 65 may acquire bone registration data for example at the medial distal condyle 4020. The controller 65 may acquire bone registration data, for example, at the medial distal condyle 4020, or at any other position on the femur 4005 when touched by the pointer input device 92.

In some embodiments, the bone registration data may include geometric points defined along a surface of the bone member as shown in FIGS. 45 and 46 which may use medical image data to delineate the bone edge boundaries and other bone features. The bone registration data may be used to model a bone member representation in which the geometric points along the bone edge boundaries and/or other bone features may be defined within a coordinate system. In other embodiments, each bone member representation may be defined in its own unique coordinate system. In yet other embodiments, the first bone member representation may be defined in a single coordinate system.

In some embodiments, using the bone registration data as shown in FIGS. 45 and 46, the controller 65 may use the First/Second Bone member representation modeler 74 to generate a first bone member representation of the first bone member and a second bone member representation of the second bone member using the bone registration data.

Figure 47:
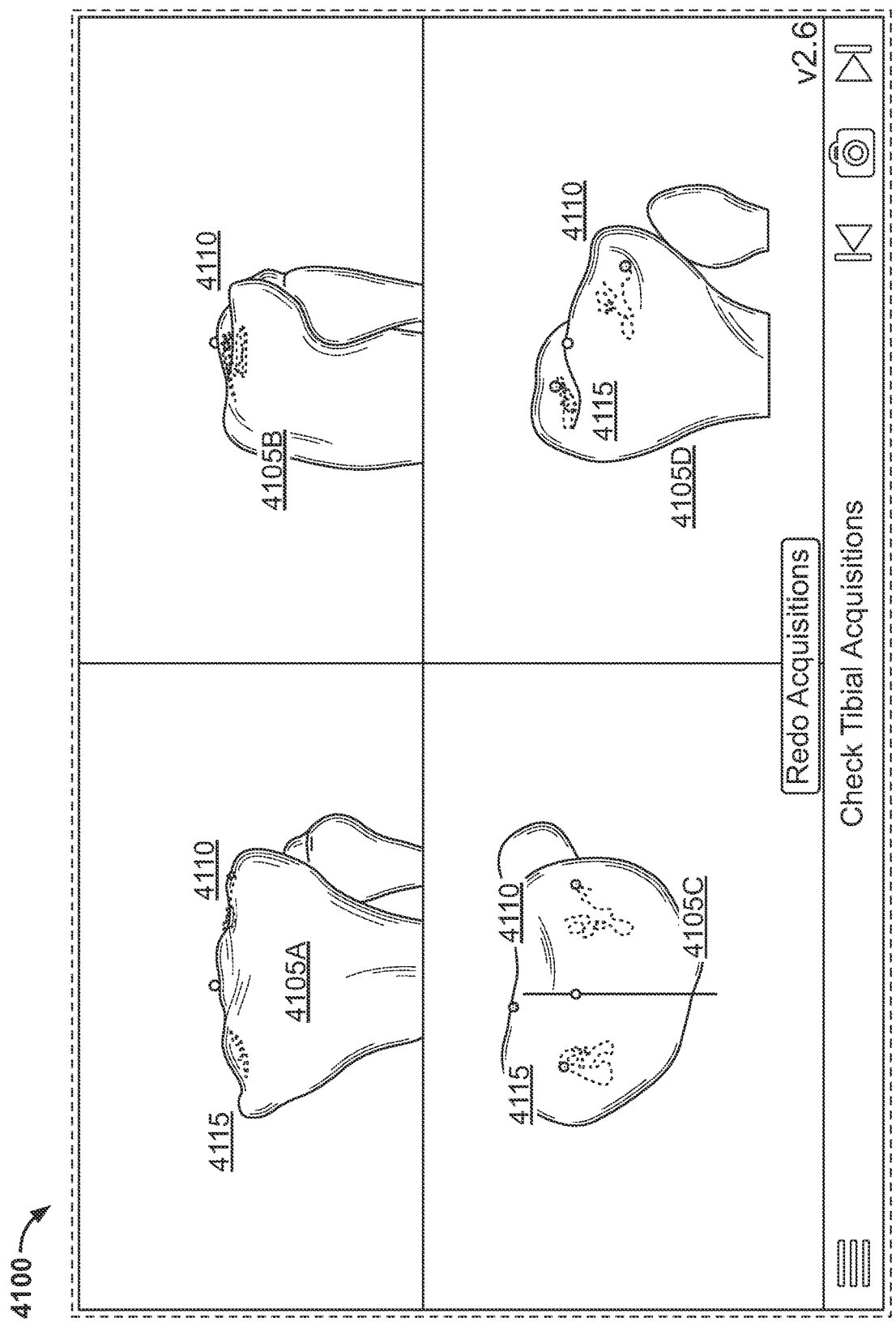
FIG. 47 illustrates a snapshot of a graphic user interface displaying of a first bone member representation in accordance with one or more embodiments of the present disclosure.

FIG. 47 illustrates a snapshot 4100 of the graphic user interface 61 displaying of a first bone member representation in accordance with one or more embodiments of the present disclosure. The first bone representation may include different geometric views of the first bone member (e.g., the tibia) such as 4105A, 4105B, 4105C, and 4105D. A plurality of acquired registration points in the first bone representation may be shown in the medial tibial plateau 4110 and the lateral tibial plateau 4115.

FIG. 48 illustrates a snapshot 4200 of the graphic user interface 61 displaying a second bone member representation in accordance with one or more embodiments of the present disclosure. The second bone representation may include different geometric views of the second bone member (e.g., the femur) such as 4205A, 4205B, 4205C, and 4205D. A plurality of acquired registration points in the second bone representation may be shown in the medial condyle 4220 and the lateral condyle 4210.

In some embodiments, when the movement-related data is acquired during the surgical procedure using the ligament balancing device 800 to apply the distraction force, at this stage in the surgery, one of the bone members such as the tibia may have been cut. For example, in femoral cut planning, the tibia may have been surgically cut and the ligament balancing device 800 may be placed between the cut tibial surface and the femur. Similarly, in other embodiments, the ligament balancing device 800 may be placed in the joint gap between the uncut femur and tibia.

FIG. 49 illustrates a snapshot 4300 of the graphic user interface 61 displaying the acquired movement-related data in accordance with one or more embodiments of the present disclosure. A medial gap 4315 between the femur and tibia may be 16 mm and a lateral gap 4320 of 12 mm.

FIG. 50 is a graph of a laxity curve 4400 showing the measured medial gap and lateral gap over a range of flexion angles in accordance with one or more embodiments of the present disclosure. The laxity curve may be determined from the movement-related data acquired during the arthroplasty surgical procedure.

Figure 51:
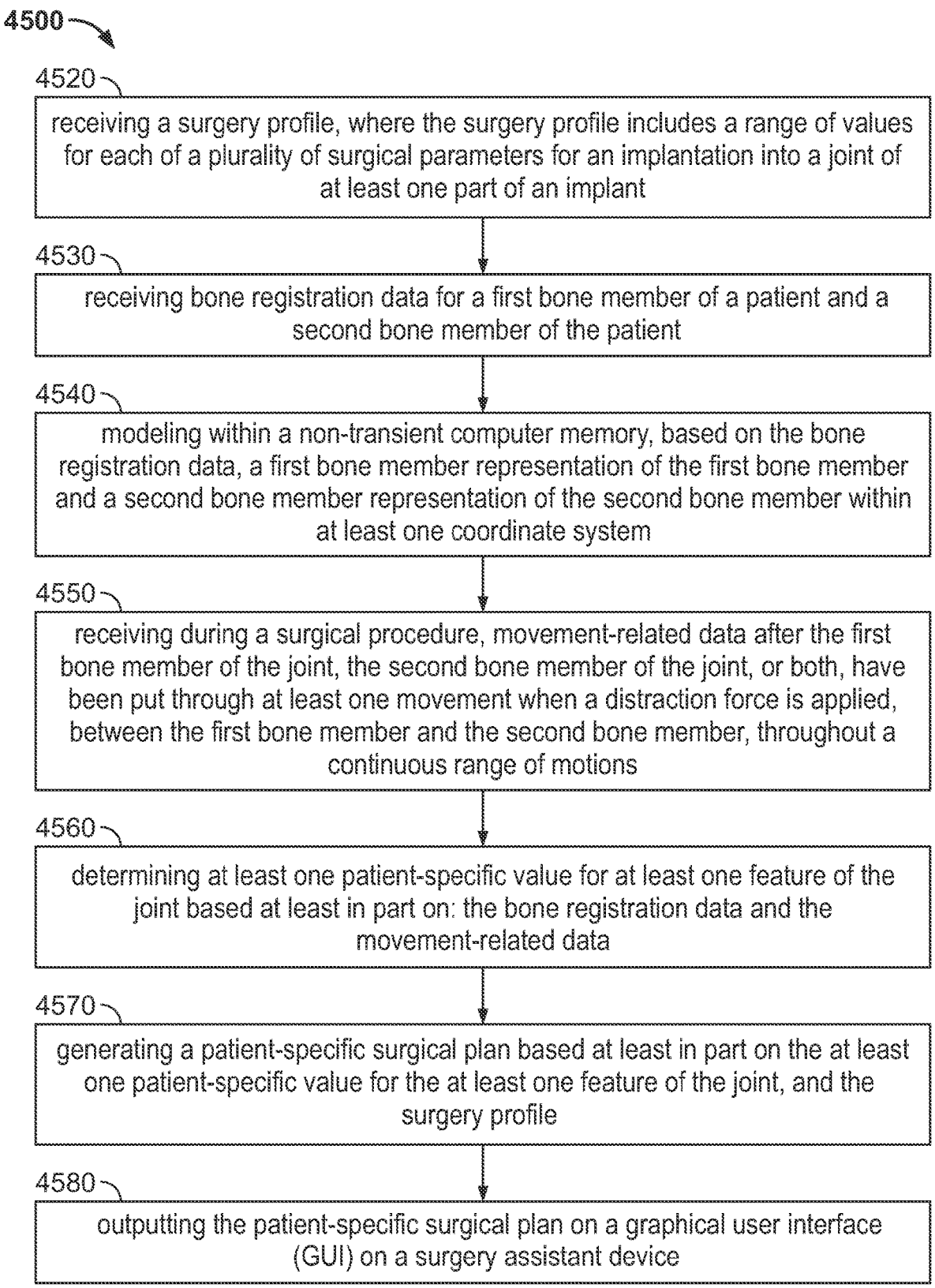
FIG. 51 is a flowchart of a method for using an improved computer-based platform for a personalization of inputs used in a surgical planning setup for a total joint arthroplasty procedure in accordance with one or more embodiments of the present disclosure.

FIG. 51 is a flowchart of a method 4500 for using an improved computer-based platform for a personalization of inputs used in a surgical planning setup for a total joint arthroplasty procedure in accordance with one or more embodiments of the present disclosure. The method 4500 may be performed by the controller 65.

The method 4500 may include receiving 4520 a surgery profile, where the surgery profile includes a range of values for each of a plurality of surgery guidance parameters for an implantation into a joint of at least one part of the implant.

The method 4500 may include receiving 4530 bone registration data for a first bone member of a patient and a second bone member of the patient.

The method 4500 may include modeling 4540, within a non-transient computer memory, based on the bone registration data, a first bone member representation of the first bone member and a second bone member representation of the second bone member within at least one coordinate system.

The method 4500 may include receiving 4550, during a surgical procedure, movement-related data after the first bone member of the joint, the second bone member of the joint, or both, have been put through at least one movement when a distraction force is applied, between the first bone member and the second bone member, throughout a continuous range of motions.

The method 4500 may include determining 4560 at least one patient-specific value for at least one feature of the joint based at least in part on the bone registration data and the movement-related data. The at least one feature of the joint may be at least one laxity curve and the at least one patient-specific value may be a at least one personalized flexion angle (see FIG. 12C).

The method 4500 may include generating 4570 a patient-specific surgical plan based at least in part on the at least one patient-specific value for the at least one feature of the joint, and the surgery profile.

The method 4500 may include outputting 4580 the patient-specific surgical plan on a graphical user interface (GUI) on a surgery assistant device.

Figure 52:
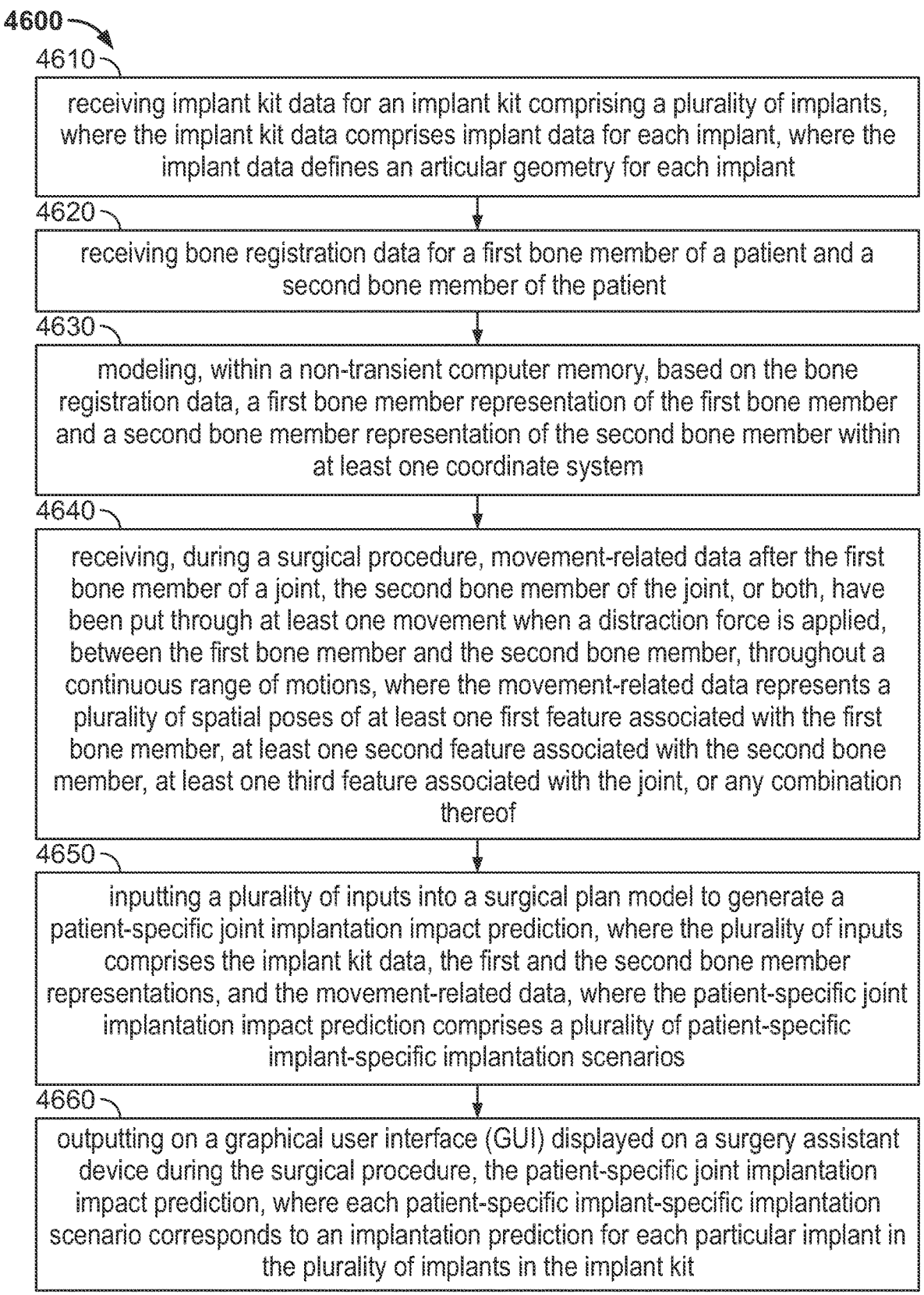
FIG. 52 is a flowchart of a method for using an improved computer-based platform for implant planning during a total joint arthroplasty in accordance with one or more embodiments of the present disclosure.

FIG. 52 is a flowchart of a method 4600 for using an improved computer-based platform for implant planning during a total joint arthroplasty in accordance with one or more embodiments of the present disclosure. The method 4600 may be performed by the controller 65.

The method 4600 may include receiving 4610 implant kit data for an implant kit including a plurality of implants, where the implant kit data includes implant data for each implant, where the implant data defines an articular geometry for each implant. See the Implant component kit 3455 in FIG. 38, and FIGS. 35A-35C.

The method 4600 may include receiving 4620 bone registration data for a first bone member of a patient and a second bone member of the patient.

The method 4600 may include modeling 4630, within a non-transient computer memory, based on the bone registration data, a first bone member representation of the first bone member and a second bone member representation of the second bone member within at least one coordinate system.

The method 4600 may include receiving 4640 during a surgical procedure, movement-related data after the first bone member of a joint, the second bone member of the joint, or both, have been put through at least one movement when a distraction force is applied, between the first bone member and the second bone member, throughout a continuous range of motions, where the movement-related data represents a plurality of spatial poses of at least one first feature associated with the first bone member, at least one second feature associated with the second bone member, at least one third feature associated with the joint, or any combination thereof.

The method 4600 may include inputting 4650 a plurality of inputs into a surgical plan model to generate a patient-specific joint implantation impact prediction, where the plurality of inputs includes the implant kit data, the first and the second bone member representations, and the movement-related data, where the patient-specific joint implantation impact prediction includes a plurality of patient-specific implant-specific implantation scenarios.

The method 4600 may include outputting 4660, on a graphical user interface (GUI) displayed on a surgery assistant device during the surgical procedure, the patient-specific joint implantation impact prediction, where each patient-specific implant-specific implantation scenario corresponds to an implantation prediction for each implant in the plurality of implants in the implant kit. (See FIGS. 36A-36C—predicted laxity curves.)

In some embodiments, the surgical plan generator model 75 may be implemented using a trained machine learning model 77. The machine learning model 77 may be trained using datasets that map a set of input data vectors to a set of output data vectors. The set of input data vectors may include any combination of: the plurality of patient-specific values for the plurality of patient-specific parameters, the plurality of healthcare-specific values for the plurality of healthcare-specific parameters into the surgical plan model, the first range of surgeon-specific surgery guidance values for each of the plurality of surgical parameters, the at least one functional parameter value for the at least one functional parameter representative of the expected functional performance of the joint after the implantation, the first and the second bone member representations, and the movement-related data.

In some embodiments, the set of output data vectors may include surgical parameters of the patient-specific surgeon-specific surgical plan 78 described previously herein and the estimated patient-specific surgeon-specific value for each of the plurality of surgical parameters. Training of the machine learning model using these datasets bundles into the surgical plan generator model 75, the plurality of dependencies between any combination of: the plurality of patient-specific parameters, the plurality of healthcare-specific parameters, the plurality of surgical parameters, the at least one functional parameter representative of the expected functional performance of the joint, and the movement-related data so as to achieve the patient-specific post-surgery desired functional profile.

In some embodiments, the surgical plan generator model 75 may be trained with an input dataset that may include the first range of surgeon-specific surgery guidance values for each of the plurality of surgical parameters, the at least one functional parameter value for the at least one functional parameter representative of the expected functional performance of the joint after the implantation, the first and the second bone member representations, and the movement-related data that may be mapped into an output dataset that may include surgical parameters of the patient-specific surgeon-specific surgical plan 78 described previously herein and the estimated patient-specific surgeon-specific value for each of the plurality of surgical parameters. Training of the machine learning model using these datasets bundles into the surgical plan generator model 75, the plurality of dependencies between any combination of: the first range of surgeon-specific surgery guidance values for each of the plurality of surgical parameters, the at least one functional parameter value (e.g., at least one personalized flexion angle—see FIG. 12C) for the at least one functional parameter (e.g., at least one laxity curve) representative of the expected functional performance of the joint after the implantation, the first and the second bone member representations, and the movement-related data.

In some embodiments, the surgical plan generator model 75 may be trained with an input dataset that may include the first range of surgeon-specific surgery guidance values for each of the plurality of surgical parameters, the at least one functional parameter value for the at least one functional parameter representative of the expected functional performance of the joint after the implantation, the first and the second bone member representations, and the movement-related data that may be mapped into an output dataset that may include surgical parameters of the patient-specific surgeon-specific surgical plan 78 described previously herein and the estimated patient-specific surgeon-specific value for each of the plurality of surgical parameters. Training of the machine learning model using these datasets bundles into the surgical plan generator model 75, the plurality of dependencies between any combination of: the first range of surgeon-specific surgery guidance values for each of the plurality of surgical parameters, the at least one functional parameter value (e.g., at least one personalized flexion angle—see FIG. 12C) for the at least one functional parameter (e.g., at least one laxity curve) representative of the expected functional performance of the joint after the implantation, the first and the second bone member representations, and the movement-related data.

In some embodiments, the surgical plan generator model 75 may be trained with an input dataset that may include the implant kit data for an implant kit including a plurality of implants, the first and the second bone member representations, and the movement-related data that may be mapped into an output dataset that may include a patient-specific joint implantation impact where each patient-specific implant-specific implantation scenario may correspond to an implantation prediction for each implant in the plurality of implants in the implant kit prediction including a plurality of patient-specific implant-specific implantation scenarios. The patient-specific joint implantation impact prediction may include at least one predicted laxity curve for the joint over a range of flexion angles after an implantation of an implant chosen from the implant kit.

In some embodiments, exemplary inventive, specially programmed computing systems/platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiments, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of exemplary inventive computer-based systems/platforms, exemplary inventive computer-based devices, and/or exemplary inventive computer-based components of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of exemplary inventive computer-based systems/platforms, exemplary inventive computer-based devices, and/or exemplary inventive computer-based components of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a social media post, a map, an entire application (e.g., a calculator), etc. In some embodiments, as detailed herein, one or more of exemplary inventive computer-based systems/platforms, exemplary inventive computer-based devices, and/or exemplary inventive computer-based components of the present disclosure may be implemented across one or more of various computer platforms such as, but not limited to: (1) FreeBSD, NetBSD, OpenBSD; (2) Linux; (3) Microsoft Windows; (4) OS X (MacOS); (5) MacOS 11; (6) Solaris; (7) Android; (8) iOS; (9) Embedded Linux; (10) Tizen; (11) WebOS; (12) IBM i; (13) IBM AIX; (14) Binary Runtime Environment for Wireless (BREW); (15) Cocoa (API); (16) Cocoa Touch; (17) Java Platforms; (18) JavaFX; (19) JavaFX Mobile; (20) Microsoft DirectX; (21) .NET Framework; (22) Silverlight; (23) Open Web Platform; (24) Oracle Database; (25) Qt; (26) Eclipse Rich Client Platform; (27) SAP NetWeaver; (28) Smartface; and/or (29) Windows Runtime.

In some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, exemplary inventive computer-based systems/platforms, exemplary inventive computer-based devices, and/or exemplary inventive computer-based components of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, exemplary inventive computer-based systems/platforms, exemplary inventive computer-based devices, and/or exemplary inventive computer-based components of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, and/or objects. For example, such projections may be a visual overlay for a mobile augmented reality (MAR) application.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, the terms "proximity detection," "locating," "location data," "location information," and "location tracking" refer to any form of location tracking technology or locating method that can be used to provide a location of, for example, a particular computing device/system/platform of the present disclosure and/or any associated computing devices, based at least in part on one or more of the following techniques/devices, without limitation: accelerometer(s), gyroscope(s), Global Positioning Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the exemplary inventive computer-based systems/platforms, the exemplary inventive computer-based devices, and/or the exemplary inventive computer-based components of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

In some embodiments, the exemplary inventive computer-based systems/platforms, the exemplary inventive computer-based devices, and/or the exemplary inventive computer-based components of the present disclosure may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:
  i) Define Neural Network architecture/model,
  ii) Transfer the input data to the exemplary neural network model,
  iii) Train the exemplary model incrementally,
  iv) determine the accuracy for a specific number of timesteps,
  v) apply the exemplary trained model to process the newly-received input data,
  vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated.

In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments, a method, may include:
receiving, by at least one controller, during a surgical procedure and prior to modeling a surgical plan for an implantation of at least one part of an implant, bone registration data for a first bone member of a patient and a second bone member of the patient;
modeling, by the at least one controller, within a non-transient computer memory, based on the bone registration data, a first bone member representation of the first bone member and a second bone member representation of the second bone member within at least one coordinate system;
modeling, by the at least one controller, within a non-transient computer memory, a joint representation of a joint based at least in part on the first bone member representation of the first bone member and the second bone member representation of the second bone member;
receiving, by the at least one controller, during the surgical procedure, movement-related data after the first bone member of the joint, the second bone member of the joint, or both, have been put through at least one movement when a distraction force is applied, between the first bone member and the second bone member, throughout a continuous range of motions;
where the movement-related data may represent a plurality of spatial poses of at least one first feature associated with the first bone member, at least one second feature of the second bone member, or both;
modeling, by the at least one controller, based on the movement-related data, a plurality of feature representations of a respective feature within a respective coordinate system of a respective bone member representation of a respective bone member of the joint representation of the joint;
modeling, by the at least one controller, a plurality of spatial relationships between the first bone member representation of the first bone member and the second bone member representation of the second bone member based at least in part on:
i) the plurality of feature representations and
ii) the joint representation of the joint;
determining, by the at least one controller, at least one patient-specific benchmark parameter;
determining, by the at least one controller, a patient specific benchmark value for the at least one patient-specific benchmark parameter based at least in part on the plurality of spatial relationships;
obtaining, by the at least one controller, during the surgical procedure, patient-specific intra-surgical benchmark data at the patient-specific benchmark value for the at least one patient-specific benchmark parameter; and
generating, by the at least one controller, during the surgical procedure and prior to an implantation of at least one part of an implant, based at least in part on the patient-specific intra-surgical benchmark data, the surgical plan for performing at least one additional surgical action for the implantation of the at least one part of an implant.

In some embodiments, the determining of the patient specific benchmark value for the at least one patient-specific benchmark parameter may be based on analysis of curves tracing spatial presence of landmarks at a plurality of angles.

In some embodiments, the determining of the patient specific benchmark value for the at least one patient-specific benchmark parameter may be based on a trained machine learning model.

In some embodiments, the patient-specific benchmark value may be a patient-specific benchmark angle; and the method may further include:
generating, by the at least one controller, at least one patient-specific laxity curve based on the plurality of spatial relationships; and
determining, by the at least one controller, the patient-specific benchmark angle based on each respective slope of each respective portion of a particular pair portions of the patient-specific laxity curve.

In some embodiments, the method may further include
receiving, by the at least one controller, training data comprising a plurality of data series, defining a plurality of training spatial relationships based at least in part on training landmark tracking data and training joint member tracking data for a plurality of joints;
where a particular data series of the plurality of data series may include a particular series of values defining a plurality of gaps between a first joint member and a second joint member at a plurality of angles during the range of motion of a particular joint; and
training, by the at least one controller, a machine learning model based on the training data to obtain the trained machine learning model.

In some embodiments, the patient-specific benchmark value may be a patient-specific benchmark angle; and the method may further include using, by the at least one controller, a trained machine learning model configured to:
determine a leading coefficient for a particular gap of the plurality of gaps;
determine a minimum angle for the particular gap when one of:
(i) the leading coefficient is at a local minimum on a patient-specific laxity curve, or
(ii) the leading coefficient is below a predetermined threshold value; and
define the patient-specific benchmark angle based on the minimum angle.

In some embodiments, the receiving of the movement-related data when the distraction force is applied may include receiving the movement-related data when a ligament balancing device is inserted into the joint to apply the distraction force.

In some embodiments, the method may further include determining, by the at least one controller, a thickness of a patient-specific liner for the joint implant based at least in part on the patient-specific intra-surgical benchmark data.

In some embodiments, the method may further include determining, by the at least one controller, a shape of a patient-specific liner for the joint implant based at least in part on the patient-specific intra-surgical benchmark data.

In some embodiments, the patient-specific benchmark value may be a patient-specific benchmark angle; and the method may further include:
  receiving, by the at least one controller, patient outcome data for a plurality of patients having joint implants;
  receiving, by the at least one controller, surgical plan data for the plurality of patients; and
    where the surgical plan data may include a respective plurality of surgical plans for a respective plurality of joint implant surgeries performed on the plurality of patients;
    where each surgical plan may include the patient-specific intra-surgical benchmark data;
  training, by the at least one controller, a second machine learning model based on the patient outcome data and the surgical plan data to obtain a second trained machine learning model, configured to associate at least one operational capability of a post-surgical joint with the patient-specific benchmark angle.

In some embodiments, the method may further include:
  receiving, by the at least one controller, from the patient, a desired operational capability preference, identifying a desired post-surgical operational capability of the joint; and
  utilizing, by the at least one controller, the second trained machine learning model to determine the patient-specific benchmark angle based at least in part on the desired operational capability preference of the patient.

In some embodiments, where the surgical procedure may be a total knee arthroplasty;
  where the patient-specific benchmark value may be a patient-specific benchmark angle; wherein the joint comprises a lateral gap and a medial gap;
  and the method may further include using, by the at least one controller, a trained machine learning model configured to:
    determine a first leading coefficient for the lateral gap;
    determine a second leading coefficient for the medial gap;
    determine a first minimum angle for the lateral gap when one of:
      (i) the first leading coefficient is at a local minimum on a first patient-specific laxity curve, derived from the plurality of spatial relationships, or
      (ii) the first leading coefficient is below a first predetermined threshold value; determine a second minimum angle for the medial gap when one of:
      (i) the second leading coefficient is at a local minimum on a second patient-specific laxity curve, derived from the plurality of spatial relationships, or
      (ii) the second leading coefficient is below a second predetermined threshold value; and
    determine the patient-specific benchmark angle based on:
      (i) the first minimum angle for the lateral gap, and
      (ii) the second minimum angle for the medial gap.

In some embodiments, where the surgical procedure is a total knee arthroplasty;
  where the patient-specific benchmark value is a patient-specific benchmark angle;
  and the method may further include using, by the at least one controller, a trained machine learning model configured to:
    determine a leading coefficient for at least one gap in the joint;
    determine a minimum angle for the at least one gap when one of:
      (i) the leading coefficient is at a local minimum on a patient-specific laxity curve, or
      (ii) the leading coefficient is below a predetermined threshold value; and
    determine the patient-specific benchmark angle based on the minimum angle for the at least one gap.

In some embodiments, the receiving of the movement-related data may include receiving the movement-related data after the first bone member of the joint, the second bone member of the joint, or both, have been put through the at least one movement when the distraction force is applied with a neutral alignment.

A system may include a memory and at least one controller.

The at least one controller may be configured to execute software code stored in the memory that configures the at least one controller to:
  receive during a surgical procedure and prior to modeling a surgical plan for an implantation of at least one part of an implant, bone registration data for a first bone member of a patient and a second bone member of the patient;
  model within a non-transient computer memory, based on the bone registration data, a first bone member representation of the first bone member and a second bone member representation of the second bone member within at least one coordinate system;
  model within a non-transient computer memory, a joint representation of a joint based at least in part on the first bone member representation of the first bone member and the second bone member representation of the second bone member;
  receive during the surgical procedure, movement-related data after the first bone member of the joint, the second bone member of the joint, or both, have been put through at least one movement when a distraction force is applied, between the first bone member and the second bone member, throughout a continuous range of motions;
    where the movement-related data may represent a plurality of spatial poses of at least one first feature associated with the first bone member, at least one second feature of the second bone member, or both;
  model based on the movement-related data, a plurality of feature representations of a respective feature within a respective coordinate system of a respective bone member representation of a respective bone member of the joint representation of the joint;
  model a plurality of spatial relationships between the first bone member representation of the first bone member and the second bone member representation of the second bone member based at least in part on:
    i) the plurality of feature representations and
    ii) the joint representation of the joint;

determine at least one patient-specific benchmark parameter;

determine a patient specific benchmark value for the at least one patient-specific benchmark parameter based at least in part on the plurality of spatial relationships;

obtain during the surgical procedure, patient-specific intra-surgical benchmark data at the patient-specific benchmark value for the at least one patient-specific benchmark parameter; and generate during the surgical procedure and prior to an implantation of at least one part of an implant, based at least in part on the patient-specific intra-surgical benchmark data, the surgical plan for performing at least one additional surgical action for the implantation of the at least one part of an implant.

In some embodiments, the at least one patient-specific benchmark parameter may be a patient-specific dimension of at least one gap between the first and the second bone members of the joint at a particular angle between the first and the second bone members.

In some embodiments, the at least one controller may be configured to determine the patient specific benchmark value for the at least one patient-specific benchmark parameter is based on analysis of curves tracing spatial presence of landmarks at a plurality of angles.

In some embodiments, the at least one controller may be configured to determine the patient specific benchmark value for the at least one patient-specific benchmark parameter is based on a trained machine learning model.

In some embodiments, the patient-specific benchmark value may be a patient-specific benchmark angle; and where the at least one controller may be configured to:
  generate at least one patient-specific laxity curve based on the plurality of spatial relationships; and
  determine the patient-specific benchmark angle based on each respective slope of each respective portion of a particular pair portions of the patient-specific laxity curve.

In some embodiments, the at least one controller may be further configured to:
  receive training data comprising a plurality of data series, defining a plurality of training spatial relationships based at least in part on training landmark tracking data and training joint member tracking data for a plurality of joints;
    where a particular data series of the plurality of data series may include a particular series of values defining a plurality of gaps between a first joint member and a second joint member at a plurality of angles during the range of motion of a particular joint; and
  train a machine learning model based on the training data to obtain the trained machine learning model.

In some embodiments, the patient-specific benchmark value may be a patient-specific benchmark angle; and where the at least one controller may be further configured to use a trained machine learning model configured to:
  determine a leading coefficient for a particular gap of the plurality of gaps;
  determine a minimum angle for the particular gap when one of:
    (i) the leading coefficient is at a local minimum on a patient-specific laxity curve, or
    (ii) the leading coefficient is below a predetermined threshold value; and
  define the patient-specific benchmark angle based on the minimum angle.

In some embodiments, the system may further include a ligament balancing device; and
  where the at least one controller may be further configured to receive the movement-related data when the distraction force is applied by receiving the movement-related data when the ligament balancing device is inserted into the joint to apply the distraction force.

In some embodiments, the at least one controller may be further configured to determine a thickness of a patient-specific liner for the joint implant based at least in part on the patient-specific intra-surgical benchmark data.

In some embodiments, the at least one controller may be further configured to determine a shape of a patient-specific liner for the joint implant based at least in part on the patient-specific intra-surgical benchmark data.

In some embodiments, the patient-specific benchmark value may be a patient-specific benchmark angle; and where the at least one controller may be further configured to:
  receive patient outcome data for a plurality of patients having joint implants;
  receive surgical plan data for the plurality of patients;
    where the surgical plan data may include a respective plurality surgical plans for a respective plurality of joint implant surgeries performed on the plurality of patients;
    where each surgical plan may include the patient-specific intra-surgical benchmark data; and
  train a second machine learning model based on the patient outcome data and the surgical plan data to obtain a second trained machine learning model, configured to associate at least one operational capability of a post-surgical joint with the patient-specific benchmark angle.

In some embodiments, where the at least one controller may be further configured to:
  receive from the patient, a desired operational capability preference, identifying a desired post-surgical operational capability of the joint; and
  utilize the second trained machine learning model to determine the patient-specific benchmark angle based at least in part on the desired operational capability preference of the patient.

In some embodiments, where the surgical procedure may be a total knee arthroplasty;
  where the patient-specific benchmark value may be a patient-specific benchmark angle; wherein the joint comprises a lateral gap and a medial gap;
  and where the at least one controller may be further configured to use a trained machine learning model configured to:
  determine a first leading coefficient for the lateral gap;
  determine a second leading coefficient for the medial gap;
  determine a first minimum angle for the lateral gap when one of:
    (i) the first leading coefficient is at a local minimum on a first patient-specific laxity curve, derived from the plurality of spatial relationships, or
    (ii) the first leading coefficient is below a first predetermined threshold value;
  determine a second minimum angle for the medial gap when one of:
    (i) the second leading coefficient is at a local minimum on a second patient-specific laxity curve, derived from the plurality of spatial relationships, or
    (ii) the second leading coefficient is below a second predetermined threshold value; and
  determine the patient-specific benchmark angle based on:

(i) the first minimum angle for the lateral gap, and (ii) the second minimum angle for the medial gap.

In some embodiments, where the surgical procedure may be a total knee arthroplasty;

where the patient-specific benchmark value may be a patient-specific benchmark angle;

and where the at least one controller may be further configured to use a trained machine learning model configured to:

determine a leading coefficient for at least one gap in the joint;

determine a minimum angle for the at least one gap when one of:

(i) the leading coefficient is at a local minimum on a patient-specific laxity curve, or (ii) the leading coefficient is below a predetermined threshold value; and determine the patient-specific benchmark angle based on the minimum angle for the at least one gap.

In some embodiments, the at least one controller may be configured to receive the movement-related data after the first bone member of the joint, the second bone member of the joint, or both, have been put through the at least one movement when the distraction force is applied with a neutral alignment.

In some embodiments, a method may include:

receiving, by at least one controller, a surgeon-specific surgery profile;

where the surgeon-specific surgery profile may include a first range of surgeon-specific surgery guidance values for each of a plurality of surgical parameters for an implantation into a joint of at least one part of an implant chosen from a plurality of implants;

receiving, by the at least one controller, a patient-specific post-surgery desired functional profile of the joint after the implantation;

where the patient-specific post-surgery desired functional profile may include at least one functional parameter value for at least one functional parameter representative of an expected functional performance of the joint after the implantation;

receiving, by the at least one controller, bone registration data for a first bone member of a patient and a second bone member of the patient;

modeling, by the at least one controller, within a non-transient computer memory, based on the bone registration data, a first bone member representation of the first bone member and a second bone member representation of the second bone member within at least one coordinate system;

receiving, by the at least one controller, during a surgical procedure, movement-related data after the first bone member of the joint, the second bone member of the joint, or both, have been put through at least one movement when a distraction force is applied, between the first bone member and the second bone member, throughout a continuous range of motions;

where the movement-related data may represent a plurality of spatial poses of at least one first feature associated with the first bone member, at least one second feature associated with the second bone member, at least one third feature associated with the joint, or any combination thereof;

inputting, by the at least one controller, a plurality of inputs into a surgical plan model to generate a patient-specific surgeon-specific surgical plan;

where the patient-specific surgeon-specific surgical plan may include an estimated patient-specific surgeon-specific value for each of the plurality of surgical parameters;

where the plurality of inputs may include:

the first range of surgeon-specific surgery guidance values for each of the plurality of surgical parameters, the at least one functional parameter value for the at least one functional parameter representative of the expected functional performance of the joint after the implantation, the first and the second bone member representations, and the movement-related data;

where the surgical plan model may be designed to achieve the patient-specific post-surgery desired functional profile based at least in part on a plurality of dependencies between:

the plurality of surgical parameters, the at least one functional parameter representative of the expected functional performance of the joint, and the movement-related data; and outputting, by the at least one controller, the patient-specific surgeon-specific surgical plan on a graphical user interface (GUI) on a surgery assistant device to facilitate the implantation.

In some embodiments, the method may include receiving, by the at least one controller, a plurality of implant profiles for the plurality of implants;

where each implant profile may include implant-specific manufacturer limit parameters for each implant.

In some embodiment, the estimated patient-specific surgeon-specific value for each of the plurality of surgical parameters may be within each of the first range of surgeon-specific surgery guidance values for each corresponding surgical parameter in the plurality of surgical parameters.

In some embodiments, the plurality of surgical parameters may include at least one first cut parameter at a particular position, orientation, or both, on the first bone member, at least one second cut parameter at a particular position, orientation, or both, on the second bone member, or any combination thereof.

In some embodiments, the plurality of surgical parameters may include: a medial distal femoral resection, a lateral distal femoral resection, a medial posterior femoral resection, a lateral posterior femoral resection, a femoral antero-posterior (AP) position, a femoral alignment angle, a femoral flexion angle, and a femoral axial rotation angle.

In some embodiments, the at least one functional parameter may include a medial gap in extension, a medial gap in flexion at 90 degrees, a lateral gap in extension, a lateral gap in flexion at 90 degrees, and a laxity tolerance.

In some embodiments, the at least one functional parameter may include at least one joint gap for at least one position within the continuous range of motions.

In some embodiments, the first range of surgeon-specific surgery guidance values for each of the plurality of surgical parameters may include an acceptable range of surgeon-specific surgery guidance values and a preferred range of surgeon-specific surgery guidance values.

In some embodiments, the outputting of the patient-specific surgeon-specific surgical plan on the graphical user interface (GUI) may include outputting on the GUI, a GUI output for each of the plurality of surgical parameters, where the GUI output may include manufacturer limits associated with the implant, the acceptable range of surgeon-specific surgery guidance values, the preferred range of surgeon-specific surgery guidance values, and the estimated patient-specific surgeon-specific value.

In some embodiments, the outputting of the patient-specific surgeon-specific surgical plan on the graphical user interface (GUI) may include outputting on the GUI output, at least one indicator indicating a fulfillment of the expected functional performance of the joint after the implantation for each of: an alignment parameter, a balance parameter, a sizing parameter, or any combination thereof based on the patient-specific surgeon-specific surgical plan.

In some embodiments, the at least one indicator may include an interactive icon, where the outputting of the patient-specific surgeon-specific surgical plan on the graphical user interface (GUI) may include outputting full details of the patient-specific surgeon-specific surgical plan associated with a specific indicator from the at least one indicator for the alignment parameter, the balance parameter, or the sizing parameter, when the surgeon activates the interactive icon associated the specific indicator on the GUI with an input device.

In some embodiments, the outputting of the patient-specific surgeon-specific surgical plan on the graphical user interface (GUI) may include generating a plurality of interactive GUI interface elements that are programmed to allow a user to adjust the estimated patient-specific surgeon-specific value for at least one surgical parameter from the plurality of surgical parameters displayed on the GUI.

In some embodiments, the method may further include receiving, by the at least one controller, an input from any of the plurality of interactive GUI interface elements to a respective surgical parameter of the plurality of surgical parameters; and
updating, by the at least one controller, based on the surgical plan model and the input, at least one other interactive GUI interface element corresponding to the estimated patient-specific surgeon-specific value for at least one other surgical parameter from the plurality of surgical parameters.

In some embodiments, the method may further include inputting, by the at least one controller, the movement-related data into the surgical plan model that is further configured to generate a laxity curve of the joint of the patient.

In some embodiments, the method may include receiving, by the at least one controller, a patient-specific profile;
wherein the patient-specific profile comprises a plurality of patient-specific values for a plurality of patient-specific parameters;
receiving, by the at least one controller, a healthcare-specific profile;
wherein the healthcare-specific profile comprises a plurality of healthcare-specific values for a plurality of healthcare-specific parameters;
wherein the inputting of the plurality of inputs into the surgical plan model comprises inputting the plurality of patient-specific values for the plurality of patient-specific parameters and the plurality of healthcare-specific values for the plurality of healthcare-specific parameters into the surgical plan model; and
wherein the surgical plan model is designed to achieve the patient-specific post-surgery desired functional profile based at least in part on the plurality of dependencies between:
the plurality of patient-specific parameters,
the plurality of healthcare-specific parameters,
the plurality of surgical parameters,
the at least one functional parameter representative of the expected functional performance of the joint, and
the movement-related data.

In some embodiments, the joint may be a knee joint; and where the surgical procedure may be a total knee arthroplasty surgical procedure.

In some embodiments, the plurality of surgery guidance parameters may include: a medial distal femoral resection, a lateral distal femoral resection, a medial posterior femoral resection, a lateral posterior femoral resection, a femoral anteroposterior (AP) position, a femoral alignment angle, a femoral flexion angle, a femoral axial rotation angle, or any combination thereof.

In some embodiments, the at least one feature may include a medial gap in extension, a medial gap in flexion at 90 degrees, a lateral gap in extension, a lateral gap in flexion at 90 degrees, and a laxity tolerance.

In some embodiments, the joint may be a knee joint, and where the surgical procedure may be a medial partial knee arthroplasty surgical procedure.

In some embodiments, the plurality of surgical parameters may include: a medial distal femoral resection, a medial posterior femoral resection, a femoral anteroposterior (AP) position, a femoral alignment angle, a femoral flexion angle, a femoral axial rotation angle, or any combination thereof.

In some embodiments, the at least one functional parameter may include a medial gap in extension, a medial gap in flexion at 90 degrees, and a laxity tolerance.

In some embodiments, the joint is a knee joint; and where the surgical procedure may be a lateral partial knee arthroplasty surgical procedure.

In some embodiments, the plurality of surgical parameters may include: a lateral distal femoral resection, a lateral posterior femoral resection, a femoral anteroposterior (AP) position, a femoral alignment angle, a femoral flexion angle, a femoral axial rotation angle, or any combination thereof.

In some embodiments, the at least one functional parameter may include a lateral gap in extension, a lateral gap in flexion at 90 degrees, and a laxity tolerance.

In some embodiments, the joint may be a shoulder joint; and where the surgical procedure may be a shoulder arthroplasty surgical procedure.

In some embodiments, the plurality of surgical parameters may include: a version of a glenoid resection, an inclination of the glenoid resection, a position of the glenoid resection, a depth of the glenoid resection, or any combination thereof.

In some embodiments, the at least one functional parameter may include a shoulder joint gap in adduction, a shoulder joint gap in abduction, and a laxity tolerance.

In some embodiments, the joint may be an ankle joint and where the surgical procedure may be a total ankle arthroplasty surgical procedure.

In some embodiments, the plurality of surgical parameters may include: a medial proximal talar resection, a lateral proximal talar resection, a talar anteroposterior (AP) position, a talar alignment angle, a talar flexion angle, a talar axial rotation angle, or any combination thereof.

In some embodiments, the at least one functional parameter may include a medial gap in plantarflexion, a medial gap in dorsiflexion, a lateral gap in plantarflexion, a lateral gap in dorsiflexion at 90 degrees, and a laxity tolerance.

In some embodiments, a system may include a memory and at least one controller that is configured to execute computer code stored in the memory that causes the at least one controller to:
receive a surgeon-specific surgery profile;

where the surgeon-specific surgery profile may include a first range of surgeon-specific surgery guidance values for each of a plurality of surgical parameters for an implantation into a joint of at least one part of an implant chosen from a plurality of implants;

receive a patient-specific post-surgery desired functional profile of the joint after the implantation;
where the patient-specific post-surgery desired functional profile may include at least one functional parameter value for at least one functional parameter representative of an expected functional performance of the joint after the implantation;

receive bone registration data for a first bone member of a patient and a second bone member of the patient;

model within a non-transient computer memory, based on the bone registration data, a first bone member representation of the first bone member and a second bone member representation of the second bone member within at least one coordinate system;

receive, during a surgical procedure, movement-related data after the first bone member of the joint, the second bone member of the joint, or both, have been put through at least one movement when a distraction force is applied, between the first bone member and the second bone member, throughout a continuous range of motions;
where the movement-related data may represent a plurality of spatial poses of at least one first feature associated with the first bone member, at least one second feature associated with the second bone member, at least one third feature associated with the joint, or any combination thereof;

input a plurality of inputs into a surgical plan model to generate a patient-specific surgeon-specific surgical plan;
where the patient-specific surgeon-specific surgical plan may include an estimated patient-specific surgeon-specific value for each of the plurality of surgical parameters;
where the plurality of inputs may include:
the first range of surgeon-specific surgery guidance values for each of the plurality of surgical parameters,
the at least one functional parameter value for the at least one functional parameter representative of the expected functional performance of the joint after the implantation,
the first and the second bone member representations, and
the movement-related data;
where the surgical plan model may be designed to achieve the patient-specific post-surgery desired functional profile based at least in part on a plurality of dependencies between:
the plurality of surgical parameters,
the at least one functional parameter representative of the expected functional performance of the joint, and
the movement-related data;

output the patient-specific surgeon-specific surgical plan on a graphical user interface (GUI) on a surgery assistant device to facilitate the implantation.

In some embodiments, the at least one controller may be further configured to receive a plurality of implant profiles for the plurality of implants, where each implant profile may include implant-specific manufacturer limit parameters for each implant.

In some embodiments, the estimated patient-specific surgeon-specific value for each of the plurality of surgical parameters may be within each of the first range of surgeon-specific surgery guidance values for each corresponding surgical parameter in the plurality of surgical parameters.

In some embodiments, the plurality of surgical parameters may include: a medial distal femoral resection, a lateral distal femoral resection, a medial posterior femoral resection, a lateral posterior femoral resection, a femoral anteroposterior (AP) position, a femoral alignment angle, a femoral flexion angle, and a femoral axial rotation angle.

In some embodiments, the plurality of surgical parameters comprises at least one first cut parameter at a particular position, orientation, or both, on the first bone member, at least one second cut parameter at a particular position, orientation, or both, on the second bone member, or any combination thereof.

In some embodiments, the at least one functional parameter may include at least one joint gap value for at least one position within the continuous range of motions.

In some embodiments, the at least one functional parameter comprises a medial gap in extension, a medial gap in flexion at 90 degrees, a lateral gap in extension, a lateral gap in flexion at 90 degrees, and a laxity tolerance.

In some embodiments, the first range of surgeon-specific surgery guidance values for each of the plurality of surgical parameters may include an acceptable range of surgeon-specific surgery guidance values and a preferred range of surgeon-specific surgery guidance values.

In some embodiments, the at least one controller may be configured to output the patient-specific surgeon-specific surgical plan on the graphical user interface (GUI) by outputting on the GUI, a GUI output for each of the plurality of surgical parameters;
where the GUI output may include manufacturer limits associated with the implant, the acceptable range of surgeon-specific surgery guidance values, the preferred range of surgeon-specific surgery guidance values, and the estimated patient-specific surgeon-specific value.

In some embodiments, the at least one controller may be configured to output the patient-specific surgeon-specific surgical plan on the graphical user interface (GUI) by outputting on the GUI output, at least one indicator indicating a fulfillment of the expected functional performance of the joint after the implantation for each of: an alignment parameter, a balance parameter, a sizing parameter, or any combination thereof based on the patient-specific surgeon-specific surgical plan.

In some embodiments, the at least one indicator may include an interactive icon, where the the at least one controller is configured to output the patient-specific surgeon-specific surgical plan on the graphical user interface (GUI) by outputting full details of the patient-specific surgeon-specific surgical plan associated with a specific indicator from the at least one indicator for the alignment parameter, the balance parameter, or the sizing parameter, when the surgeon activates the interactive icon associated the specific indicator on the GUI with an input device.

In some embodiments, the at least one controller may be configured to output the patient-specific surgeon-specific surgical plan on the graphical user interface (GUI) by generating a plurality of interactive GUI interface elements that are programmed to allow a user to adjust the estimated patient-specific surgeon-specific value for at least one surgical parameter from the plurality of surgical parameters displayed on the GUI.

In some embodiments, the at least one controller may be further configured to receive an input from any of the plurality of interactive GUI interface elements to a respective surgical parameter of the plurality of surgical parameters; and where the at least one controller may be further configured to update, based on the surgical plan model and the input, at least one other interactive GUI interface element corresponding to the estimated patient-specific surgeon-specific value for at least one other surgical parameter from the plurality of surgical parameters.

In some embodiments, the at least one controller may be further configured to input the movement-related data into the surgical plan model that is further configured to generate a laxity curve of the joint of the patient.

In some embodiments, the at least one controller may be further configured to receive a patient-specific profile, where the patient-specific profile may include a plurality of patient-specific values for a plurality of patient-specific parameters; where the at least one controller is further configured to receive a healthcare-specific profile, where the healthcare-specific profile may include a plurality of healthcare-specific values for a plurality of healthcare-specific parameters, where the at least one controller is further configured to input of the plurality of inputs into the surgical plan model by inputting the plurality of patient-specific values for the plurality of patient-specific parameters and the plurality of healthcare-specific values for the plurality of healthcare-specific parameters into the surgical plan model, and where the surgical plan model is designed to achieve the patient-specific post-surgery desired functional profile based at least in part on the plurality of dependencies between:
- the plurality of patient-specific parameters,
- the plurality of healthcare-specific parameters,
- the plurality of surgical parameters,
- the at least one functional parameter representative of the expected functional performance of the joint, and
- the movement-related data In some embodiments, a method may include:
- receiving, by at least one controller, a surgery profile;
  - where the surgery profile may include a range of values for each of a plurality of surgical parameters for an implantation into a joint of at least one part of an implant;
- receiving, by the at least one controller, bone registration data for a first bone member of a patient and a second bone member of the patient;
- modeling, by the at least one controller, within a non-transient computer memory, based on the bone registration data, a first bone member representation of the first bone member and a second bone member representation of the second bone member within at least one coordinate system;
- receiving, by the at least one controller, during a surgical procedure, movement-related data after the first bone member of the joint, the second bone member of the joint, or both, have been put through at least one movement when a distraction force is applied, between the first bone member and the second bone member, throughout a continuous range of motions;
- determining, by the at least one controller, at least one patient-specific value for at least one feature of the joint based at least in part on:
  - the bone registration data and
  - the movement-related data;
- generating, by the at least one controller, a patient-specific surgical plan based at least in part on:
  - the at least one patient-specific value for the at least one feature of the joint, and
  - the surgery profile; and
- outputting, by the at least one controller, the patient-specific surgical plan on a graphical user interface (GUI) on a surgery assistant device.

In some embodiments, the method may include receiving, by the at least one controller, at least one implant profile for the implant.

In some embodiments, the plurality of surgery guidance parameters may include: a medial distal femoral resection, a lateral distal femoral resection, a medial posterior femoral resection, a lateral posterior femoral resection, a femoral anteroposterior (AP) position, a femoral alignment angle, a femoral flexion angle, and a femoral axial rotation angle.

In some embodiments, the plurality of surgical parameters comprises at least one cut parameter at a particular position, orientation or both on the first bone member, at least one cut parameter at a particular position, orientation or both on the second bone member, or any combination thereof.

In some embodiments, the at least one feature may include a medial gap in extension, a medial gap in flexion at 90 degrees, a lateral gap in extension, a lateral gap in flexion at 90 degrees, and a laxity tolerance.

In some embodiments, the at least one feature may include at least one joint gap value for at least one position within the continuous range of motions.

In some embodiments, the at least one feature of the joint may include a laxity curve of a joint gap;
  where the at least one patient-specific value may include a personalized flexion angle; and
  where the determining of the at least one patient-specific value for the laxity curve of the joint may include determining the personalized flexion angle based on the laxity curve of the joint.

In some embodiments, the outputting of the patient-specific surgical plan on the graphical user interface (GUI) may include outputting on the GUI, the laxity curve with the personalized flexion angle.

In some embodiments, a system may include a memory and at least one controller that may be configured to execute computer code stored in the memory that causes the at least one controller to:
- receive a surgery profile;
  - where the surgery profile may include a range of values for each of a plurality of surgical parameters for an implantation into a joint of at least one part of an implant;
- receive bone registration data for a first bone member of a patient and a second bone member of the patient;
- model within a non-transient computer memory, based on the bone registration data, a first bone member representation of the first bone member and a second bone member representation of the second bone member within at least one coordinate system;
- receive, during a surgical procedure, movement-related data after the first bone member of the joint, the second bone member of the joint, or both, have been put through at least one movement when a distraction force is applied, between the first bone member and the second bone member, throughout a continuous range of motions;
- determine at least one patient-specific value for at least one feature of the joint based at least in part on:
  - the bone registration data and
  - the movement-related data;

generate a patient-specific surgical plan based at least in part on:
    the at least one patient-specific value for the at least one feature of the joint, and
    the surgery profile; and
output the patient-specific surgical plan on a graphical user interface (GUI) on a surgery assistant device.

In some embodiments, the at least one controller may be configured to receive at least one implant profile for the implant.

In some embodiments, the plurality of surgery guidance parameters may include: a medial distal femoral resection, a lateral distal femoral resection, a medial posterior femoral resection, a lateral posterior femoral resection, a femoral anteroposterior (AP) position, a femoral alignment angle, a femoral flexion angle, and a femoral axial rotation angle.

In some embodiments, the plurality of surgical parameters comprises at least first one cut parameter at a particular position, orientation, or both, on the first bone member, at least second one cut parameter at a particular position, orientation, or both, on the second bone member, or any combination thereof.

In some embodiments, the at least one feature may include a medial gap in extension, a medial gap in flexion at 90 degrees, a lateral gap in extension, a lateral gap in flexion at 90 degrees, and a laxity tolerance.

In some embodiments, the at least one feature may include at least one joint gap value for at least one position within the continuous range of motions.

In some embodiments, the at least one feature of the joint may include at least one laxity curve of a joint gap;
    where the at least one patient-specific value may include at least one personalized flexion angle; and
    where the at least one controller may be configured to determine the at least one patient-specific value for the at least one laxity curve of the joint by determining the at least one personalized flexion angle based on the at least one laxity curve of the joint.

In some embodiments, the at least one controller may be configured to output the patient-specific surgical plan on the graphical user interface (GUI) by outputting on the GUI, the at least one laxity curve with the at least one personalized flexion angle.

In some embodiments, a method may include:
receiving, by at least one controller, implant kit data for an implant kit including a plurality of implants;
    where the implant kit data may include implant data for each implant;
    where the implant data may define an articular geometry for each implant;
receiving, by the at least one controller, bone registration data for a first bone member of a patient and a second bone member of the patient;
modeling, by the at least one controller, within a non-transient computer memory, based on the bone registration data, a first bone member representation of the first bone member and a second bone member representation of the second bone member within at least one coordinate system;
receiving, by the at least one controller, during a surgical procedure, movement-related data after the first bone member of a joint, the second bone member of the joint, or both, have been put through at least one movement when a distraction force is applied, between the first bone member and the second bone member, throughout a continuous range of motions;
    where the movement-related data may represent a plurality of spatial poses of at least one first feature associated with the first bone member, at least one second feature associated with the second bone member, at least one third feature associated with the joint, or any combination thereof;
inputting, by the at least one controller, a plurality of inputs into a surgical plan model to generate a patient-specific joint implantation impact prediction;
    where the plurality of inputs may include:
        the implant kit data,
        the first and the second bone member representations, and
        the movement-related data;
    where the patient-specific joint implantation impact prediction may include a plurality of patient-specific implant-specific implantation scenarios; and
outputting, by the at least one controller, on a graphical user interface (GUI) displayed on a surgery assistant device during the surgical procedure, the patient-specific joint implantation impact prediction;
    where each patient-specific implant-specific implantation scenario may correspond to an implantation prediction for each implant in the plurality of implants in the implant kit.

In some embodiments, the outputting of the patient-specific joint implantation impact prediction may include outputting at least one predicted laxity curve for the joint after an implantation of an implant chosen from the implant kit. (See FIGS. 36A-36C—predicted laxity curves.)

In some embodiments, the outputting of the at least one predicted laxity curve for the joint after the implantation may include outputting at least one laxity curve over a range of flexion angles.

In some embodiments, the method may include further comprising receiving, by the at least one controller, the implant data for at least two implants from the plurality of implants chosen by a user from the implant kit; and
    where the outputting of the plurality of patient-specific implant-specific implantation scenarios may include outputting a comparison of a predicted laxity curve for the joint between each of at least two implants after implantation into the joint.

In some embodiments, a first implant from the at least two implants may include a standard implant from the implant kit;
    where a second implant from the at least two implants may include an implant having a modified articular geometry to improve a soft-tissue balance in a joint relative to the articular geometry of the standard implant; and
    where the outputting of the comparison may include outputting a first predicted laxity curve for the first implant and a second predicted laxity curve for the second implant;
    where the second predicted laxity curve may show an improvement using the second implant due to the modified articular geometry relative to the first predicted laxity curve with the standard implant. (See FIGS. 36A-36C—laxity curves for implants with modified articular geometries).

In some embodiments, a system may include:
an implant kit including a plurality of implants;
    where implant kit data may include implant data for each implant;
    where the implant data may define an articular geometry for each implant;

a memory; and at least one controller that may be configured to execute computer code stored in the memory that causes the at least one controller to:

receive the implant kit data;

receive bone registration data for a first bone member of a patient and a second bone member of the patient;

model, within a non-transient computer memory, based on the bone registration data, a first bone member representation of the first bone member and a second bone member representation of the second bone member within at least one coordinate system;

receive during a surgical procedure, movement-related data after the first bone member of a joint, the second bone member of the joint, or both, have been put through at least one movement when a distraction force is applied, between the first bone member and the second bone member, throughout a continuous range of motions;

where the movement-related data may represent a plurality of spatial poses of at least one first feature associated with the first bone member, at least one second feature associated with the second bone member, at least one third feature associated with the joint, or any combination thereof;

input a plurality of inputs into a surgical plan model to generate a patient-specific joint implantation impact prediction;

where the plurality of inputs may include:
the implant kit data,
the first and the second bone member representations, and
the movement-related data;

where the patient-specific joint implantation impact prediction may include a plurality of patient-specific implant-specific implantation scenarios; and output on a graphical user interface (GUI) displayed on a surgery assistant device during the surgical procedure, the patient-specific joint implantation impact prediction;

where each patient-specific implant-specific implantation scenario may correspond to an implantation prediction for each implant in the plurality of implants in the implant kit.

In some embodiments, the at least one controller may be configured to output the patient-specific joint implantation impact prediction by outputting a predicted laxity curve for the joint after an implantation of an implant chosen from the implant kit.

In some embodiments, the at least one controller may be configured to output the at least one predicted laxity curve for the joint after the implantation by outputting at least one laxity curve over a range of flexion angle.

In some embodiments, the at least one controller may be further configured to receive the implant data for at least two implants from the plurality of implants chosen by a user from the implant kit; and where the at least one controller may be configured to output the plurality of patient-specific implant-specific implantation scenarios by outputting a comparison of a predicted laxity curve for the joint between each of at least two implants after implantation into the joint.

In some embodiments, a first implant from the at least two implants may include a standard implant from the implant kit;

where a second implant from the at least two implants may include an implant having a modified articular geometry to improve a soft-tissue balance in a joint relative to the articular geometry of the standard implant; and where the at least one controller may be configured to output the comparison by outputting a first predicted laxity curve for the first implant and a second predicted laxity curve for the second implant;

where the second predicted laxity curve may show an improvement using the second implant due to the modified articular geometry relative to the first predicted laxity curve with the standard implant.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the inventive systems/platforms, and the inventive devices described herein can be utilized in any combination with each other. Further still, the various steps may be carried out in any desired order (and any desired steps may be added and/or any desired steps may be eliminated).

The invention claimed is:

1. A method, comprising:

obtaining a patient-specific post-surgery desired functional profile of a joint of a patient after a surgical procedure of an implantation of an implant;

wherein the joint comprises a first bone member and a second bone member;

wherein the patient-specific post-surgery desired functional profile comprises at least one functional parameter value for at least one functional parameter representative of an expected functional performance of the joint after the implantation;

obtaining a surgeon-specific surgery profile of a surgeon;

wherein the surgeon-specific surgery profile comprises a plurality of ranges of surgeon-specific surgery guidance values for each of a plurality of surgical parameters for the implantation of at least one part of the implant chosen from a plurality of implants;

wherein the plurality of surgical parameters comprises:
at least one resection associated with at least one of the first bone member or the second bone member,
at least one position of at least one of the first bone member or the second bone member within the joint,
an alignment angle of at least one of the first bone member or the second bone member,
a flexion angle of at least one of the first bone member or the second bone member, or
an axial rotation angle of at least one of the first bone member or the second bone member;

wherein the plurality of ranges of the surgeon-specific surgery guidance values comprises:
a first range of surgeon-specific surgery guidance values for the at least one resection associated with at least one of the first bone member or the second bone member,
a second range of surgeon-specific surgery guidance values for the at least one position of at least one part of at least one of the first bone member or the second bone member within the joint,
a third range of surgeon-specific surgery guidance values for the alignment angle of at least one of the first bone member or the second bone member,
a fourth range of surgeon-specific surgery guidance values for the flexion angle of at least one of the first bone member or the second bone member, or
a fifth range of surgeon-specific surgery guidance values for the axial rotation angle of at least one of the first bone member or the second bone member;
wherein the plurality of ranges of the surgeon-specific surgery guidance values for each of the plurality of surgical parameters comprises an acceptable range in each of the plurality of ranges of the surgeon-specific surgery guidance values;
cutting the first bone member during the surgical procedure;
placing a distractor between the first bone member and the second bone member to apply, during at least one movement, a distraction force between the first bone member and the second bone member;
obtaining bone registration data for the first bone member of the patient and the second bone member of the patient;
obtaining, based on the bone registration data, a first bone member representation of the first bone member and a second bone member representation of the second bone member within at least one coordinate system;
obtaining, during the surgical procedure, patient-specific movement-related data after the first bone member of the joint, the second bone member of the joint, or both, have been put through the at least one movement when the distraction force is applied, between the first bone member and the second bone member, throughout a continuous range of motions;
wherein the patient-specific movement-related data represents a plurality of spatial poses of at least one first feature associated with the first bone member, at least one second feature associated with the second bone member, at least one third feature associated with the joint, or any combination thereof;
obtaining, from the patient-specific movement-related data, a personalized flexion angle of the joint;
obtaining a patient-specific surgeon-specific surgical plan based on a plurality of inputs into a surgical plan model;
wherein the patient-specific surgeon-specific surgical plan comprises an estimated patient-specific surgeon-specific value for each of the plurality of surgical parameters;
wherein the plurality of inputs comprises:
the plurality of ranges of the surgeon-specific surgery guidance values for each of the plurality of surgical parameters,
the at least one functional parameter value for the at least one functional parameter representative of the expected functional performance of the joint after the implantation,
the first and the second bone member representations,
the personalized flexion angle of the joint, and
the patient-specific movement-related data;
wherein the surgical plan model is designed to:
achieve the patient-specific post-surgery desired functional profile based at least in part on a plurality of dependencies between:
the plurality of surgical parameters,
the at least one functional parameter representative of the expected functional performance of the joint,
the personalized flexion angle of the joint, and
the patient-specific movement-related data, and
determine the estimated patient-specific surgeon-specific value for each of the plurality of surgical parameters in a compensated set of surgical cut parameters from the plurality of surgical parameters, compensated by the personalized flexion angle of the joint, to consider during the surgical procedure;
obtaining the estimated patient-specific surgeon-specific value for each of the plurality of surgical parameters in the compensated set of surgical cut parameters of the patient-specific surgeon-specific surgical plan from at least one interactive graphical user interface (GUI) on a surgery assistant device; and
cutting the second bone member at the joint based on the estimated patient-specific surgeon-specific values in the compensated set of surgical cut parameters of the patient-specific surgeon-specific surgical plan, compensated by the personalized flexion angle of the joint, to consider during the surgical procedure.

2. The method according to claim 1, wherein the estimated patient-specific surgeon-specific value for each of the plurality of surgical parameters is within each of the plurality of ranges of the surgeon-specific surgery guidance values for each corresponding surgical parameter in the plurality of surgical parameters.

3. The method according to claim 1, wherein the plurality of surgical parameters comprises at least one first cut parameter at a particular position, orientation, or both, on the first bone member, at least one second cut parameter at a particular position, orientation, or both, on the second bone member, or any combination thereof.

4. The method according to claim 1, wherein the plurality of ranges of the surgeon-specific surgery guidance values for each of the plurality of surgical parameters comprises a preferred range in each of the plurality of ranges of the surgeon-specific surgery guidance values.

5. The method according to claim 1, wherein the obtaining from the at least one interactive GUI, a GUI output for each of the plurality of surgical parameters;
wherein the GUI output comprises manufacturer limits associated with the implant, the acceptable range in each of the plurality of ranges of the surgeon-specific surgery guidance values, a preferred range in each of the plurality of ranges of the surgeon-specific surgery guidance values, and the estimated patient-specific surgeon-specific value.

6. The method according to claim 1, further comprising:
obtaining a patient-specific profile;
wherein the patient-specific profile comprises a plurality of patient-specific values for a plurality of patient-specific parameters;
obtaining a healthcare-specific profile;
wherein the healthcare-specific profile comprises a plurality of healthcare-specific values for a plurality of healthcare-specific parameters;
wherein the obtaining of the patient-specific surgeon-specific surgical plan is based on an inputting of the plurality of patient-specific values for the plurality of patient-specific parameters and the plurality of healthcare-specific values for the plurality of healthcare-specific parameters into the surgical plan model; and wherein the surgical plan model is further designed to achieve the patient-specific post-surgery desired functional profile based at least in part on the plurality of dependencies between:

the plurality of patient-specific parameters,
the plurality of healthcare-specific parameters,
the plurality of surgical parameters,
the at least one functional parameter representative of the expected functional performance of the joint,
the personalized flexion angle of the joint, and
the patient-specific movement-related data.

7. The method according to claim 1, wherein the joint is a knee joint; and wherein the at least one functional parameter comprises a medial gap in extension, a medial gap in flexion at 90 degrees, a lateral gap in extension, a lateral gap in flexion at 90 degrees, a gap tolerance, or any combination thereof.

8. The method according to claim 1, wherein the obtaining of the patient-specific post-surgery desired functional profile of the joint comprises obtaining the patient-specific post-surgery desired functional profile of the joint based on a patient-specific post-operative desired lifestyle constraint.

9. The method according to claim 8, wherein the patient-specific post-operative desired lifestyle constraint is selected from the group consisting of: a desired participation in a particular sport, a desired comfort level, a desired range of motion, and a desired longevity.

10. The method according to claim 1, wherein the joint is a knee joint.

11. The method according to claim 10, wherein the compensated set of surgical cut parameters from the plurality of surgical parameters comprises:

a medial distal femoral resection,
a lateral distal femoral resection,
a medial posterior femoral resection,
a lateral posterior femoral resection,
a femoral anteroposterior (AP) position,
a femoral alignment angle,
a femoral flexion angle, and
a femoral axial rotation angle.

12. The method according to claim 1, wherein the at least one interactive GUI comprises a plurality of interactive GUI interface elements that are programmed to allow an adjustment of the estimated patient-specific surgeon-specific value for at least one surgical parameter from the plurality of surgical parameters displayed on the at least one interactive GUI.

13. The method according to claim 12, further comprising:

adjusting any of the plurality of interactive GUI interface elements to change at least one displayed patient-specific surgeon-specific value for the at least one surgical parameter of the plurality of surgical parameters;

obtaining, based on the surgical plan model and the adjusting, the estimated patient-specific surgeon-specific value for each of the plurality of surgical parameters in response to the change in the at least one displayed patient-specific surgeon-specific value for the at least one surgical parameter; and obtaining on the at least one interactive GUI, a real-time update of each of the plurality of interactive GUI interface elements corresponding to the estimated patient-specific surgeon-specific value for each of the plurality of surgical parameters in response to the adjusting.

\* \* \* \* \*